United States Patent
Ghannoum et al.

(10) Patent No.: US 10,426,761 B2
(45) Date of Patent: *Oct. 1, 2019

(54) METHOD FOR TREATMENT OF DISEASE CAUSED OR AGGRAVATED BY MICROORGANISMS OR RELIEVING SYMPTOMS THEREOF

(71) Applicant: ARMS Pharmaceutical LLC, Cleveland, OH (US)

(72) Inventors: Afif Mahmoud Ghannoum, Shaker Heights, OH (US); Brian Vincent Sokol, Vermilion, OH (US)

(73) Assignee: ARMS Pharmaceutical, LLC, Cleveland, OH (US)

( * ) Notice: Subject to any disclaimer, the term of this patent is extended or adjusted under 35 U.S.C. 154(b) by 47 days.

This patent is subject to a terminal disclaimer.

(21) Appl. No.: 14/063,185

(22) Filed: Oct. 25, 2013

(65) Prior Publication Data

US 2014/0051731 A1 Feb. 20, 2014

Related U.S. Application Data

(63) Continuation-in-part of application No. 14/014,448, filed on Aug. 30, 2013, which is a continuation of application No. 13/448,926, filed on Apr. 17, 2012, now Pat. No. 8,535,646.

(60) Provisional application No. 61/477,147, filed on Apr. 19, 2011, provisional application No. 61/829,608, filed on May 31, 2013, provisional application No. 61/859,960, filed on Jul. 30, 2013, provisional application No. 61/749,195, filed on Jan. 4, 2013.

(51) Int. Cl.

| | | |
|---|---|---|
| *A01N 43/40* | (2006.01) | |
| *A61K 9/00* | (2006.01) | |
| *A61K 9/08* | (2006.01) | |
| *A61K 31/4425* | (2006.01) | |
| *A61K 45/06* | (2006.01) | |
| *A61K 31/155* | (2006.01) | |
| *A61K 47/10* | (2017.01) | |
| *A61K 47/36* | (2006.01) | |

(52) U.S. Cl.
CPC .......... *A61K 31/4425* (2013.01); *A61K 9/006* (2013.01); *A61K 31/155* (2013.01); *A61K 45/06* (2013.01); *A61K 47/10* (2013.01); *A61K 47/36* (2013.01); *Y02A 50/463* (2018.01); *Y02A 50/465* (2018.01); *Y02A 50/473* (2018.01); *Y02A 50/481* (2018.01)

(58) Field of Classification Search
CPC combination set(s) only.
See application file for complete search history.

(56) References Cited

U.S. PATENT DOCUMENTS

| | | |
|---|---|---|
| 3,865,472 A | 2/1975 | Hobart et al. |
| 3,993,777 A | 11/1976 | Caughman et al. |
| 4,292,299 A | 9/1981 | Suzuki et al. |
| 4,590,067 A | 5/1986 | Meisner |
| 4,657,758 A | 4/1987 | Goldemberg et al. |
| 5,095,106 A | 3/1992 | Gaffar et al. |
| 5,124,359 A | 6/1992 | Wachman et al. |
| 5,401,723 A | 3/1995 | Gaffar et al. |
| 5,422,098 A | 6/1995 | Rolla et al. |
| 5,733,540 A | 3/1998 | Lee |
| 5,776,479 A | 7/1998 | Pallos et al. |
| 6,368,576 B1 | 4/2002 | Jensen et al. |
| 6,663,902 B1 | 12/2003 | Hei et al. |
| 6,666,902 B1 | 12/2003 | Kimura et al. |
| 6,682,722 B2 | 1/2004 | Majeti et al. |
| 6,713,049 B1 | 3/2004 | White, Jr. et al. |
| 6,749,869 B1 | 6/2004 | Richter et al. |
| 6,977,082 B2 | 12/2005 | Seitz, Jr. et al. |
| 2002/0156130 A1 | 10/2002 | Melman |

(Continued)

FOREIGN PATENT DOCUMENTS

| | | |
|---|---|---|
| CN | 101868145 A | 10/2010 |
| DE | 19529862 A1 | 2/1997 |

(Continued)

OTHER PUBLICATIONS

Baharlou, Simin, "International Preliminary Report on Patentability for PCT Patent Application No. PCT/US2013/066863", dated Jul. 7, 2015, 11 pages.

(Continued)

*Primary Examiner* — Lezah Roberts

(74) *Attorney, Agent, or Firm* — Medley, Behrens & Lewis, LLC

(57) ABSTRACT

A method for treating a disease or for treating a symptom of a disease, or a combination of both, the disease being caused or aggravated by microorganisms includes: treating the disease, treating the symptom of the disease, or reducing the duration of the disease, or a combination of both by administering a barrier-forming composition in a therapeutically effective amount to a surface, the surface comprising a mammal mucosa, the mammal being infected with the disease or experiencing symptoms of the disease caused or aggravated by the microorganisms. The barrier-forming composition includes an antimicrobial. Upon administering the composition, the method includes forming a barrier coating on the surface that is active to kill or neutralize microorganisms encountered by the barrier coating. A composition with an agent active for relieving symptoms of a disease is also included.

30 Claims, 35 Drawing Sheets

(56) References Cited

U.S. PATENT DOCUMENTS

| | | | |
|---|---|---|---|
| 2002/0168334 A1* | 11/2002 | Jacob | A61K 9/006 424/78.31 |
| 2003/0206874 A1* | 11/2003 | Doyle | A61K 8/19 424/49 |
| 2003/0232074 A1 | 12/2003 | Lipford et al. | |
| 2004/0009245 A1 | 1/2004 | Vail, III et al. | |
| 2004/0102429 A1 | 5/2004 | Modak et al. | |
| 2004/0126334 A1 | 7/2004 | White, Jr. et al. | |
| 2005/0025833 A1 | 2/2005 | Aschkenasy et al. | |
| 2005/0058673 A1* | 3/2005 | Scholz | A61K 9/0014 424/401 |
| 2005/0163727 A1* | 7/2005 | Doyle | A61K 8/347 424/48 |
| 2005/0169852 A1 | 8/2005 | Roberge et al. | |
| 2005/0182021 A1 | 8/2005 | Nichols et al. | |
| 2006/0063712 A1* | 3/2006 | Chiueh | A23L 1/3002 424/195.17 |
| 2006/0166943 A1 | 7/2006 | Van Roey et al. | |
| 2006/0251684 A1 | 7/2006 | Van Roey et al. | |
| 2007/0037723 A1 | 2/2007 | McDonnell et al. | |
| 2007/0166244 A1 | 7/2007 | Ghosh et al. | |
| 2007/0281999 A1 | 12/2007 | Fox et al. | |
| 2008/0064711 A1 | 3/2008 | Friedman | |
| 2008/0206155 A1 | 8/2008 | Tamarkin et al. | |
| 2008/0255498 A1 | 10/2008 | Houle | |
| 2008/0287538 A1* | 11/2008 | Scholz | A61L 2/18 514/552 |
| 2008/0317703 A1 | 12/2008 | Kawa et al. | |
| 2009/0081294 A1 | 3/2009 | Gin et al. | |
| 2009/0149429 A1 | 6/2009 | Arranz Plaza et al. | |
| 2009/0226541 A1 | 9/2009 | Scholz et al. | |
| 2009/0238777 A1 | 9/2009 | Joziak et al. | |
| 2009/0251684 A1 | 10/2009 | Arai et al. | |
| 2010/0055152 A1 | 3/2010 | Wahi | |
| 2012/0270909 A1 | 10/2012 | Sokol et al. | |
| 2013/0039959 A1 | 2/2013 | Sokol et al. | |
| 2013/0123308 A1 | 5/2013 | Ghannoum et al. | |
| 2013/0123309 A1 | 5/2013 | Ghannoum et al. | |
| 2013/0272971 A1 | 10/2013 | Pimenta et al. | |
| 2014/0005236 A1 | 1/2014 | Sokol et al. | |
| 2014/0051732 A1 | 2/2014 | Ghannoum et al. | |
| 2015/0031729 A1 | 1/2015 | Ghannoum et al. | |
| 2015/0306042 A1 | 10/2015 | Ghannoum et al. | |

FOREIGN PATENT DOCUMENTS

| | | |
|---|---|---|
| EP | 351301 A2 | 1/1990 |
| EP | 376363 A1 | 7/1990 |
| EP | 0736250 A1 | 10/1996 |
| EP | 1930012 A1 | 6/2008 |
| EP | 2100590 A1 | 9/2009 |
| EP | 2119426 A1 | 11/2009 |
| EP | 2193777 A1 | 6/2010 |
| EP | 2226069 A1 | 9/2010 |
| EP | 2298418 A1 | 3/2011 |
| EP | 2377577 A1 | 10/2011 |
| JP | S61501390 A | 7/1986 |
| JP | 2000516300 A | 12/2000 |
| JP | 2001517683 A | 10/2001 |
| JP | 2003511474 A | 3/2003 |
| JP | 2007515204 A | 6/2007 |
| JP | 2008507583 A | 3/2008 |
| JP | 2008533051 A | 8/2008 |
| JP | 2008535918 A | 9/2008 |
| JP | 2009523782 A | 6/2009 |
| JP | 2014518555 A | 7/2014 |
| JP | 2016504381 A | 2/2016 |
| RU | 2302865 C2 | 7/2007 |
| RU | 2325899 C2 | 6/2008 |
| RU | 2379025 C2 | 1/2010 |
| WO | 1999059410 A1 | 11/1999 |
| WO | 2000027191 A1 | 5/2000 |
| WO | 2004045572 A1 | 6/2004 |
| WO | 2007001606 A2 | 1/2007 |
| WO | 2007016067 A2 | 2/2007 |
| WO | 2008026310 A1 | 3/2008 |
| WO | 2009067605 A2 | 5/2009 |
| WO | 2009117644 A1 | 9/2009 |
| WO | 2011038446 A1 | 4/2011 |
| WO | 2012087325 A1 | 6/2012 |
| WO | 2012145307 A1 | 10/2012 |
| WO | 2013158165 A1 | 10/2013 |
| WO | 2014074331 A1 | 5/2014 |
| WO | 2014107221 A1 | 7/2014 |
| WO | 2014107572 A1 | 7/2014 |

OTHER PUBLICATIONS

Baharlou, Simin, "International Preliminary Report on Patentability for PCT Patent Application No. PCT/US2014/010174", dated Jul. 7, 2015, 6 pages.

Becamel, Philippe, "International Preliminary Report on Patentability for PCT Patent Application No. PCT/US2012/033921", dated Oct. 22, 2013, 7 pages.

Chinese State Intellectual Property Office, "First Office Action for Chinese Patent Application No. 201280030293.7", dated Mar. 12, 2015, 17 pages.

Chinese State Intellectual Property Office, "Second Office Action for Chinese Patent Application No. 201280030293.7", dated Dec. 4, 2015, 6 pages.

Commissioner of Patents, "Direction to Request Examination for Australian Patent Application No. 2012245665", dated Sep. 15, 2015, 1 page.

Dental Hygiene, 2010, vol. 30, No. 6, p. 566-570.

Department of Health and Human Services (Food and Drug Administration) (1994) Oral Health Care Products for Over-the-Counter Human Use; Tentative Final Monograph for Oral Antiseptic Drug Products.

Dutikova, Y., "International Search Report for PCT Patent Application No. PCT/US2013/066863", dated Jan. 30, 2014, 8 pages.

Dutikova, Y., "Written Opinion for PCT Patent Application No. PCT/US2013/066863", dated Jan. 30, 2014, 10 pages.

Savchenko, K., "International Search Report for PCT/US2014/010174", dated Apr. 29, 2014, 3 pages.

Holloman, Nannette, "Advisory Action for U.S. Appl. No. 13/448,957", dated Aug. 15, 2014, 3 pages.

Holloman, Nannette, "Final Office Action for U.S. Appl. No. 13/448,957", dated Jun. 6, 2014, 11 pages.

Holloman, Nannette, "Non-Final Office Action for U.S. Appl. No. 13/448,957", dated Nov. 18, 2013, 8 pages.

Holloman, Nannette, "Non-Final Office Action for U.S. Appl. No. 13/448,957", dated Oct. 10, 2014, 11 pages.

Japanese Patent Office, "Office Action for Japanese Patent Application No. 2014-506480", dated Dec. 8, 2015, 6 pages.

Johannes, Laura, "Keeping Cold and Flu Germs Out" Wall Street Journal (online) (Dec. 6, 2011) (retrieved on May 4, 2012 from http://online.wsj.com/article/SB10001424052970204903804577080410897264148.html?mod=WSJ_article_comments#articleTabs%3Darticle ).

Lambert Pharmacal Co, "So many times in a day in Danger" Life magazine, Dec. 1927, (3 pages).

Linder, Nora, "International Preliminary Report on Patentability for PCT Patent Application No. PCT/US2013/066929", dated May 12, 2015, 11 pages.

Maremonti, Michele, "Supplementary Partial European Search Report for European Patent Application No. 13777625.8", dated Nov. 6, 2015, 5 pages.

Maslova, E., International Search Report and Written Opinion for PCT Patent Application No. PCT/US2013/020254, dated May 16, 2013, 18 pages.

Nakamura, Yukari, "International Preliminary Report on Patentability for PCT Patent Application No. PCT/US2013/020254", dated Oct. 21, 2014, 11 pages.

Nozin.com, Research page (retrieved on May 4, 2012, http://nozin.com/aboutnozin.html#research).

O'Shea, Chloe, First Examination Report for New Zeland Patent Application No. 616044, dated Jul. 16, 2014, 3 pages.

(56) References Cited

OTHER PUBLICATIONS

Piteen, Frank-Albert et al., "Efficacy of Cetylpyridinium Chloride Used as Oropharyngeal Antiseptic" Arzneim.-Forsch/Drug Res. 51 (II), 588-595 (2001).
Savchenko, K., "Written Opinion for PCT/US2014/010174", dated Apr. 29, 2014, 5 pages.
Prokusheva, M., "International Search Report for PCT Patent Application No. PCT/US2012/033921", dated Sep. 6, 2012, 4 pages.
Prokusheva, M., "Written Opinion of the International Searching Authority for PCT Patent Application No. PCT/US2012/033921", dated Sep. 6, 2012, 6 pages.
"Communication Pursuant to Rules 161(2) and 162 EPC for European Patent Application No. 13777625.8", dated Dec. 5, 2014, 3 pages.
"Communication Pursuant to Rules 161(2) and 162 EPC for European Patent Application No. 13870018.2", dated Aug. 13, 2015, 2 pages.
"Communication Pursuant to Rules 161(2) and 162 EPC for European Patent Application No. 14735099.5", dated Aug. 14, 2015, 2 pages.
"Communication Pursuant to Rules 70(2) and 70a(2) EPC for European Patent Application No. 12774888.7", dated Sep. 25, 2014, 1 page.
Roberts, Lezah, Final Office Action for U.S. Appl. No. 13/448,926, dated May 3, 2013, 26 pages.
Roberts, Lezah, "Final Office Action for U.S. Appl. No. 13/655,365", dated Mar. 3, 2015, 10 pages.
Roberts, Lezah, "Final Office Action for U.S. Appl. No. 13/734,363", dated Nov. 8, 2013, 10 pages.
Roberts, Lezah, "Final Office Action for U.S. Appl. No. 13/734,470", dated Jan. 6, 2014, 23 pages.
Roberts, Lezah, "Final Office Action for U.S. Appl. No. 13/734,470", dated Mar. 17, 2015, 11 pages.
Roberts, Lezah, "Final Office Action for U.S. Appl. No. 14/014,448", dated Oct. 24, 2014, 20 pages.
Roberts, Lezah, "Non-Final Office Action for U.S. Appl. No. 13/448,926", dated Nov. 27, 2012, 14 pages.
Roberts, Lezah, "Non-Final Office Action for U.S. Appl. No. 13/655,365", dated Mar. 21, 2014, 13 pages.
Roberts, Lezah, "Non-Final Office Action for U.S. Appl. No. 13/734,363", dated Apr. 26, 2013, 19 pages.
Roberts, Lezah, "Non-Final Office Action for U.S. Appl. No. 13/734,470", dated Mar. 21, 2013, 20 pages.
Roberts, Lezah, "Non-Final Office Action for U.S. Appl. No. 14/014,448", dated Jan. 16, 2014, 20 pages.
Roberts, Lezah, "Non-Final Office Action for U.S. Appl. No. 14/014,448", dated Oct. 26, 2015, 10 pages.
Roberts, Lezah, "Restriction Requirement for U.S. Appl. No. 14/063,974", dated Apr. 9, 2015, 9 pages.
Roberts, Lezah, "Restriction Requirement for U.S. Appl. No. 13/448,926", dated Aug. 6, 2012, 7 pages.
Roberts, Lezah, "Restriction Requirement for U.S. Appl. No. 14/512,825", dated Oct. 7, 2015, 9 pages.
Shestak, A., "International Search Report for PCT Patent Application No. PCT/US2013/066929", dated Feb. 6, 2014, 8 pages.
Shestak, A., Written Opinon for PCT Patent Application No. PCT/US2013/066929, dated Feb. 6, 2014, 10 pages.
US Department of Health and Human Services, Periodontal (Gum) Disease: Causes, Symptoms and Treatments, Jan. 2006, pp. 1-16.
Vukovic, L. Basic Health Publications: User's Guide to Echinacea and Other Cold & Flu Fighters, p. 7 (2004).
Balakrishnan, et al., "Dental Caries is a Preventable Infectious Disease", Australian Dental Journal, vol. 45, No. 4, Dec. 2000, pp. 235-245.
Database Medline [Online] US National Library of Medicine (NLM), Bethesda, MD, US; May 2005 (May 2005), Caufield Page W et al: "Dental Caries: An Infectious and Transmissible Disease.", Database Accession No. NLM17036539; & Compendium of Continuing Education in Dentistry (Jamesburg, N.J.: 1995) May 2005, vol. 26, No. 5 Suppl 1, May 2005 (May 2005), pp. 10-16, ISSN:1548-8578.
Giro, Annalisa, "Communication pursuant to Article 94(3) EPC for European Patent Application No. 12774888.7", dated Feb. 17, 2016, 8 pages.
"Communication Pursuant to Rules 70(2) and 70a(2) EPC for European Patent Application No. 13777625.8", dated Mar. 18, 2016, 1 page.
Roberts, Lezah, "Non-Final Office Action for U.S. Appl. No. 14/512,825", dated Mar. 11, 2016, 9 pages.
Shterengarts, Samantha L., "Restriction Requirement for U.S. Appl. No. 14/758,902", dated Apr. 8, 2016, 8 pages.
Giro, Annalisa, "European Search Report for European Patent Application No. 12774888.7", dated Sep. 8, 2014, 8 pages.
Holloman, Nannette, "Notice of Allowance and Fees Due for U.S. Appl. No. 13/448,957", dated Jan. 21, 2015, 5 pages.
Roberts, Lezah, "Notice of Allowance and Fees Due for U.S. Appl. No. 13/448,926", dated Aug. 6, 2013, 13 pages.
Roberts, Lezah, "Restriction Requirement for U.S. Appl. No. 13/655,365", dated Sep. 16, 2013, 9 pages.
Australian Patent Office, "Examination Report for Australian Patent Application No. 2012245665", dated May 16, 2017, 4 pages.
Australian Patent Office, "Notice of Acceptance for Australian Patent Application No. 2012245665", dated Jun. 6, 2017, 3 pages.
Cattell, James, "Extended European Search Report for European Patent Application No. 13870018.2", dated Jun. 8, 2016, 4 pages.
Cattell, James, "Extended European Search Report for European Patent Application No. 14735099.5", dated Jul. 8, 2016, 4 pages.
Chinese State Intellectual Property Office, "Third Office Action for Chinese Patent Application No. 201280030293.7", dated Aug. 12, 2016, 24 pages.
Chinese State Intellectual Property Office, "Fourth Office Action for Chinese Patent Application No. 201280030293.7", dated Apr. 27, 2017, 18 pages.
European Patent Office, "Decision on the Request for Further Processing Under Rule 135(3) EPC for European Patent Application No. 13870018.2", dated May 4, 2017, 1 page.
Shterengarts, Samantha L., "Non-Final Office Action for U.S. Appl. No. 14/758,902", dated Sep. 29, 2016, 6 pages.
IP Australia, "Patent Examination Report No. 1 for Australian Patent Application No. 2012245665", dated Jun. 7, 2016, 6 pages.
Japanese Patent Office, "Office Action for Japanese Patent Application No. 2014-506480", dated Aug. 16, 2016, 8 pages.
Japanese Patent Office, "Office Action for Japanese Patent Application No. 2015-506981", dated Aug. 16, 2016, 7 pages.
Mexican Patent Office, "Office Action for Mexican Patent Application No. MX/a/2013/012151", dated Apr. 19, 2017, 6 pages.
"Communication Pursuant to Rules 70(2) and 70a(2) EPC for European Patent Application No. 13870018.2", dated Jun. 24, 2016, 1 page.
"Communication Pursuant to Rules 70(2) and 70a(2) EPC for European Patent Application No. 14735099.5", dated Jul. 26, 2016, 1 page.
Roberts, Lezah, Advisory Action for U.S. Appl. No. 14/014,448, dated Jun. 5, 2017, 3 pages.
Roberts, Lezah, Advisory Action for U.S. Appl. No. 14/014,448, dated Dec. 21, 2016, 3 pages.
Roberts, Lezah, "Final Office Action for U.S. Appl. No. 14/014,448", dated Jul. 15, 2016, 18 pages.
Roberts, Lezah, "Final Office Action for U.S. Appl. No. 14/512,825", dated Dec. 30, 2016, 8 pages.
Boukarim, et al., "Preservatives in Liquid Pharmaceutical Preparations", In the Journal of Applied Research, vol. 9, Issue 1, and 2, 2009, 4 pages.
Cattell, James, "Communication Pursuant to Article 94(3) EPC for European Patent Application No. 13870018.2", dated Feb. 26, 2018, 4 pages.
Chinese State Intellectual Property Office, "Fifth Office Action for Chinese Patent Application No. 201280030293.7", dated Nov. 16, 2017, 21 pages.
Japanese Patent Office, "Office Action for Japanese Patent Application No. 2015-551671", dated Sep. 26, 2017, 5 pages.
Japanese Patent Office, "Office Action for Japanese Patent Application No. 2016-243184", dated Sep. 12, 2017, 9 pages.

(56) References Cited

OTHER PUBLICATIONS

Japanese Patent Office, "Office Action for Japanese Patent Application No. 2016-243184", dated Jan. 30, 2018, 5 pages.
Mexican Patent Office, "Office Action for Mexican Patent Application No. MX/a/2013/012151", dated Oct. 2, 2017, 4 pages.
Roberts, Lezah, Examiner's Answer to Appeal Brief for U.S. Appl. No. 14/014,448, dated Nov. 1, 2017, 36 pages.
Chinese State Intellectual Property Office, "Sixth Office Action for Chinese Patent Application No. 201280030293.7", dated Jul. 10, 2018, 7 pages.
Eisler, Dana, "Office Action for Canadian Patent Application No. 2,832,854", dated Apr. 12, 2018, 4 pages.
Giro, Annalisa, "Communication pursuant to Article 94(3) EPC for European Patent Application No. 12774888.7", dated May 2, 2018, 8 pages.
Intellectual Property India, "First Examination Report for Indian Patent Application No. 8925/DELNP/2013", dated Jun. 15, 2018, 6 pages.
Japanese Patent Office, "Office Action for Japanese Patent Application No. 2015-551671", dated Jun. 26, 2018, 6 pages.

\* cited by examiner

METHOD FOR TREATMENT OF DISEASE CAUSED OR AGGRAVATED BY MICROORGANISMS OR RELIEVING SYMPTOMS THEREOF

CROSS-REFERENCE TO RELATED APPLICATIONS

This application is a continuation-in-part of U.S. application Ser. No. 14/014,448, filed on Aug. 30, 2013, entitled, "Method of Inhibiting Harmful Microorganisms and Barrier-Forming Composition Therefor;" which in turn, is a continuation of U.S. application Ser. No. 13/448,926, filed on Apr. 17, 2012 (now issued as U.S. Pat. No. 8,535,646) entitled, "Method of Inhibiting Harmful Microorganisms and Barrier-Forming Composition Therefor;" which, in turn, claims the benefit of priority to U.S. provisional application No. 61/477,147, filed on Apr. 19, 2011, entitled "Compositions, Methods of Use, and Methods of Making Barrier Products." The present application also claims the benefit of priority to U.S. provisional application No. 61/829,608, filed on May 31, 2013, entitled "Method for Reducing Microbial Load for Treatment of Disease Caused or Aggravated by Microorganisms or Relieving Symptoms Thereof." The present application also claims the benefit of priority to U.S. provisional application No. 61/859,960, filed on Jul. 30, 2013, entitled "Method for Reducing Duration and Severity of Symptoms of Communicable Disease." The present application also claims the benefit of priority to U.S. provisional application No. 61/749,195, filed on Jan. 4, 2013, entitled "Barrier-Forming Composition with Active Agents and Method." All of these prior applications are incorporated herein by reference for all purposes.

FIELD

This disclosure relates to barrier-forming compositions and methods for treating mucosal surfaces to treat or relieve symptoms of diseases caused or aggravated by microorganisms.

BACKGROUND

There is a longstanding need for compositions and other treatments that will effectively treat infectious diseases. This is especially true for viruses, such as the cold and flu virus. In addition, there is concern that conventional antibiotics are losing their effectiveness due to bacteria mutation and evolution. These are special concerns for individuals with elevated risks to infection, such as individuals who are immunocompromised.

Upper respiratory infections (URIs) can be caused by influenza and multiple non-influenza viruses. In a small minority (<10%) of instances URIs are caused by bacteria. URIs also may be associated with significant morbidity and mortality (especially for influenza infections). In that regard, almost 20 influenza-associated deaths are reported per 100,000 people in the U.S., with 31 million hospital visits and >200,000 hospitalizations annually. Infections associated with non-influenza viruses are known to cause 20 million lost work and school days annually. The economic burden due to URIs ranges between $40 and $87 billion. While some prevention options (e.g. influenza vaccine, antiviral medications) do exist for the control of influenza, their efficacy and availability is limited and there may also be significant side effects.

While many solutions are designed to treat symptoms of infectious disease, many only mask the symptom by inducing an alternate effect—they do not directly aid in the body recovering from the infection more quickly, nor do they actually kill germs. Some homeopathic, herbal remedies, and vitamin treatments are alleged to boost the body's ability to fight germs; however, these have speculative and unproven results. Few, if any, actually kill germs. In addition, many compositions only affect one group of harmful microorganisms (bacteria, viruses, and fungi) leaving other groups unaffected. In the case of antibiotics, fungal microorganisms may even be caused to proliferate.

SUMMARY

In an embodiment, a method for treating a disease or for treating a symptom of a disease, or a combination of the above, the disease being caused or aggravated by microorganisms includes: treating the disease, treating the symptom of the disease, or reducing the duration of the disease, or a combination of the above by administering a barrier-forming composition in a therapeutically effective amount to a surface, the surface comprising a mammal mucosa, the mammal being infected with the disease or experiencing symptoms of the disease caused or aggravated by the microorganisms. The barrier-forming composition includes an antimicrobial. Upon administering the composition, the method includes forming a barrier coating on the surface that is active to kill or neutralize microorganisms encountered by the barrier coating.

In an embodiment, a composition includes an aqueous solution that meets the following requirements:
about $0.0001\% \leq C \leq$ about 0.4%;
about $0.07\% \leq H \leq$ about 70%; and
$0.0005\% < A$
or
about $0\% \leq C \leq$ about 0.4%;
about $55\% \leq H \leq$ about 70%; and
$0.0005\% < A$
wherein all percentages are by weight of the total composition;
wherein C is a carbohydrate gum; H is a humectant; and A is the antimicrobial agent. The composition also includes a second active agent that is active for relieving symptoms of communicable disease.

In an embodiment, a method for treating a disease or for treating a symptom of a disease, or a combination of both, the disease being caused or aggravated by microorganisms, includes: treating the disease, treating the symptom of the disease, or a combination of both, by administering a barrier-forming composition in a therapeutically effective amount to a surface, the surface comprising a mammal mucosa, the mammal being infected with the disease caused or aggravated by the microorganisms. The barrier-forming composition includes an antimicrobial agent that acts by binding to a cell membrane of the microorganisms and disrupting the cell membrane, thereby causing cell death. The method includes effectively reducing the duration, frequency, or severity of the disease, or effectively reducing the duration, frequency, or severity of one or more symptoms of the disease; and safe and free of harmful side effects.

The articles "a" and "the," as used herein, mean "one or more" unless the context clearly indicates to the contrary.

The terms "item" and "apparatus" are used synonymously herein.

The term "treat" or "treating" as used herein means reducing or relieving symptoms or reducing the duration of an illness.

The term "or," as used herein, is not an exclusive or, unless the context clearly indicates to the contrary.

The use of the term "individual" or "mammal" herein, means a human or animal commonly defined as a mammal.

The term "lesion" is used herein interchangeably with the term "disruption."

The terms "block" or "blocking" as used herein, include blocking passage by trapping.

BRIEF DESCRIPTION OF THE DRAWINGS

FIG. 1 is a depiction of a proposed mechanism of antimicrobial activity in an embodiment of the barrier-forming composition.

DETAILED DESCRIPTION

Figure 2:
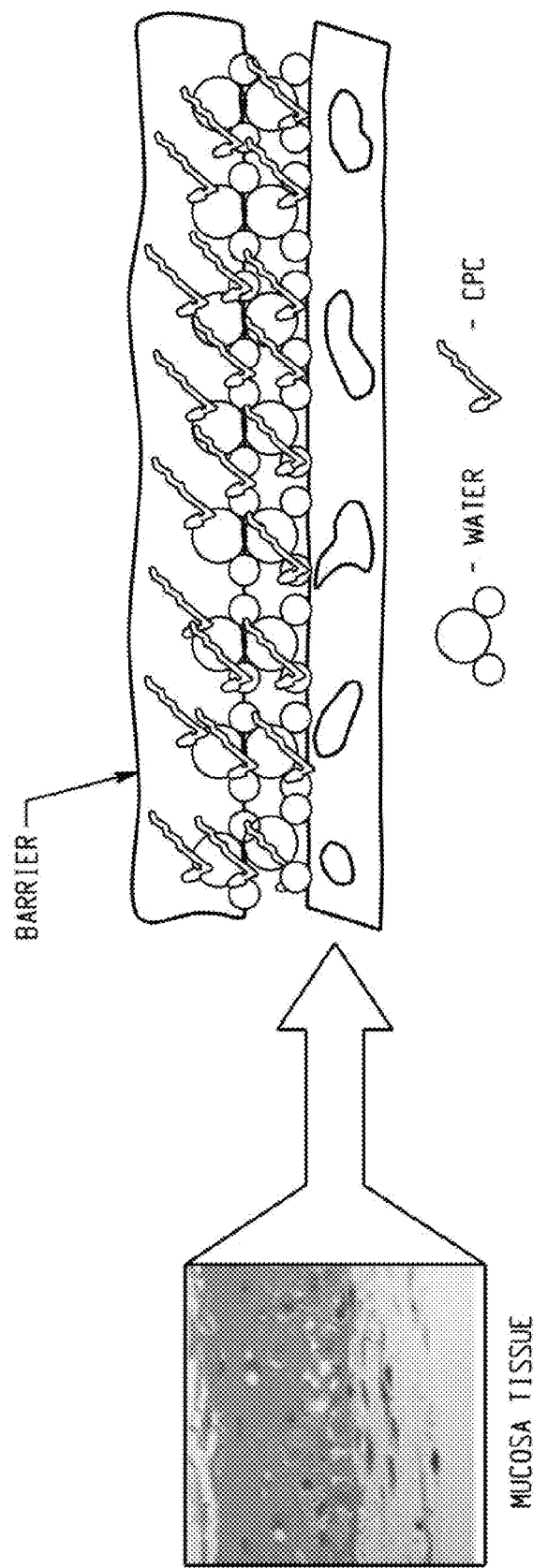
FIG. 2 is a schematic showing the formation of a barrier on a mucosal surface, as described in Example 2.

This application discloses a stable barrier-forming composition for reducing microbial load in individuals (mammals), that is effective for preventing disease and/or treating a pre-existing disease or reducing duration, frequency, or severity of symptoms of disease. In an embodiment, the barrier-forming composition is non-toxic to mammals and safe in a therapeutically effective amount. The term "safe," in this context, includes not damaging to normal skin or mucosal cells or wounds, or causing a reduction in wound healing rate. Furthermore, the composition is free of harmful side effects.

The barrier-forming composition forms a barrier coating that inhibits the passage of active pathogenic microbes through to the other side. The barrier-forming composition includes an antimicrobial component to inhibit microbial growth and kill already present microorganisms through static or cidal activity for an extended period of time. In an embodiment, the antimicrobial acts by binding to cell membranes of the microorganisms and disrupting them, thereby causing cell death. The combined barrier coating and antimicrobial synergistically act to trap and kill or neutralize microorganisms already present on the treated surface and/or to trap and kill or neutralize microorganisms that are subsequently deposited on top of the barrier, i.e., the exposed surface of the barrier coating, after the administering of the barrier forming composition is performed. The composition provides a long-lasting antimicrobial functionality that is significantly more powerful than just an antimicrobial alone.

Without being bound by theory, it is believed that the barrier-forming composition acts to relieve symptoms and/or treat diseases or symptoms of diseases caused or aggravated by microorganisms that a mammal has already contracted, by reducing the microbial load in the heavily germ loaded areas of the oral and pharyngeal mucosa, other mucosa, or open lesions. In doing so, the body is able to focus its natural defenses on fighting the disease that has already infected the individual. The effectiveness of the composition for this purpose may be evidenced by reduced symptoms of the disease (frequency, severity, and/or duration), and reduced duration and/or severity of the infection. In essence, by killing accessible germs on the oral and pharyngeal mucosa, the composition acts as an aid to the body's resources for fighting infectious disease, and allows the body to focus its resources on the harmful microorganisms that have disseminated throughout the body and are not easily accessible to man-made antimicrobials.

In an embodiment, the composition's activity is distinguished from compositions that only act by inducing a counteracting effect in the body to obscure or cover up a symptom—for example, cold and flu treatments that have activity to block or numb pain, reduce fever by inhibiting cyclooxygenase (COX), or by blocking the effect of histamines. None of such treatments are known to effectively kill germs to treat symptoms, nor do they treat the underlying disease. Antibiotics and antivirals are not mucosal treatment, not barrier forming compositions, and are not broad spectrum antimicrobials that are able to kill both viruses, bacteria, and fungi.

The composition disclosed herein has been shown to be extremely effective at killing a broad spectrum of germs (bacteria, viruses, and fungi) for an extended period of time. Without being bound by theory, the mechanism of action of the barrier-forming composition is based on a synergistic dual-action mechanism, in which germs are trapped in the formed barrier coating, and subsequently killed by the antimicrobial active ingredient. In an embodiment, the barrier-forming composition is not hydrophilic, which, without being bound by theory, is theorized to enhance its sustained effectiveness.

As shown in the Examples below, the properties of the barrier-forming composition and its effectiveness to kill a wide variety of communicable diseases and reduce microbial load were assessed using at least ten different approaches based on: (1) an in vitro anti-microbial susceptibility testing; (2) an in vitro time kill assay; (3) an in vitro biofilm model; (4) an in vitro filter insert-based model, (5) an in vivo-like engineered human oral mucosa (EHOM) model; (6) electron microscopy evaluation; (7) hydrophobicity assay; (8) physico-chemical compatibility assays; (9) cell culture-based model using monolayer of human cell lines; and (10) human clinical trials.

In an embodiment of a method for treating a disease, for treating a symptom of a disease, or for reducing the duration or severity of the disease, or a combination of the above, the disease being caused or aggravated by microorganisms, the barrier-forming composition is administered in a therapeutically effective amount to a surface, the surface comprising an oral, nasal, or pharyngeal mucosa or a skin lesion of an individual. The barrier-forming composition, once administered, forms a barrier coating on the surface that is active to trap and kill or trap and neutralize microorganisms encountered by the barrier coating for a duration of at least about one hour, thereby effectively reducing the microbial load on the surface and allowing the body to focus its inherent germ fighting resources where needed elsewhere.

Diseases that may be treated by this method include those that mammalian bodies are able to combat through inherent immune system responses. This includes, for example, influenza, rhinovirus, bacterial upper/lower respiratory tract infections, community acquired *Streptococcus* infections, community acquired *Staphylococcus* infections, as well as hospital acquired infections of these diseases, and ventilator associated pneumonia. In an embodiment, the disease is a systemic disease caused by a microorganism that is communicable.

In an embodiment, a dosage regiment for the method of treatment or reduction of symptoms, includes administering the barrier-forming composition in a therapeutically effective amount in a series of doses, such as, for example, about every 1 to 12 hours, about every 2 to 8 hours, or about every 4 to 6 hours. In another embodiment, the therapeutically effective amount of the barrier-forming composition is administered every about two to about twelve hours to the surface, such as every about three to about eight hours, or every about four to about six hours. Administering "every about two to about twelve hours" means one therapeutically effective dose being administered and then a second dose being administered about two hours later up to about twelve hours later, and additional doses, if taken, being administered in subsequent about two hour to about twelve hour increments.

In an embodiment, the barrier forming composition is administered in a therapeutically effective amount three times or more in a 24 hour period for two 24 hour periods or more, such as, for example, four to twelve times, or six to ten times for six days to ten days, or seven to thirty days. In another embodiment, the method of treatment or relief of symptoms can be continued, until no symptoms of the disease are experienced, or until the mammal is determined to be free of the disease by other medical procedures or methods. In an embodiment, the three or more doses may be taken only during daylight hours or an individual's waking hours, such as, for example, 6 AM to 6 PM, or 9 PM to 5 PM. In an embodiment, an individual may follow such a dosage regimen to provide protection during the entirety of their hours where an elevated risk condition presents itself, such as in workplace or another public gathering place where a higher germ load is expected.

In an embodiment, the first dosage may be taken in response to the mammal experiencing symptoms of the disease. For example, the mammal has been experiencing symptoms for up to about 48 hours prior to the first iteration of the administering step of the method, such as about 1 to about 36 hours, about 3 to about 24 hours, or about 6 to about 12 hours.

The symptoms may include, for example, at least one of the following: runny nose, nausea, cough, headache, sneezing, sinus pressure, aches and pains, watery eyes, sore throat, sinus congestion, chills, vomiting, malaise, fatigue, rhinorrhea, and fever. Such symptoms may be used to determine when to begin the treatment regimen, and may be the symptoms that are reduced in duration, severity, or frequency after beginning the treatment regiment. In an embodiment, improvement in symptoms may begin about 1 hour to about two days after the first treatment is administered, such as about 0.5 days to about 1.5 days, or about 8 hours to about 24 hours. Improvement in symptoms may begin after 1 initial dose to 9 doses, such as 2 doses to 6 doses, or 3 doses to 6 doses. In an embodiment cough and sore throat symptoms have a reduced duration, or severity, and/or their frequency is reduced.

In an embodiment, the mammal follows a sustained dosage regimen, for example, by administering the composition three times a day, for about one to about 90 days, or about two to about 75 days, or about one week to about ten weeks, or about 22 days to about seven weeks, or longer than about 90 days, of taking the composition in 3 doses a day. In this embodiment, further improvements in microbial load reduction, duration, frequency, and severity of symptoms, and reduction in severity or duration of disease or prevention of disease, may be realized. In addition, secondary infections may be prevented. Furthermore, the disease preventing effect may be extended even after the dosing regimen ends. For example, the protection from disease may extend up to about 3 weeks after the dosing regimen ended, such as about 2 weeks or 1 week after the dosing regimen ended.

The dosage regimen may be different for persons having different elevated risk conditions. For example, individuals already suffering with a disease, and that also have an elevated risk of infection or complications from infection, such as immunocompromised patients, may administer the barrier-forming composition proactively throughout the day, everyday, and especially when in contaminated environments or upon observing a contamination event. Individuals already suffering with a disease and also having an elevated exposure risk, or an otherwise short-term elevated risk condition, such as someone having surgery, may, for example, administer the barrier-forming composition before or during exposure to high germ risk (contaminated) environments, like hospitals.

As shown in the Examples below, such a dosage regimen has been shown to substantially reduce microbial load in human clinical trials. In vivo testing has shown that about 80% of humans following the continued dosage method show a decrease of about 50% or greater of microbial load in the oral cavity over five days of treatment.

In an embodiment, the composition is administered to prevent disease caused by microorganisms, such as airborne germs, including, for example, microorganisms that cause upper respiratory infections, cold viruses, or influenza viruses, among others listed herein. As shown in the Examples below, an embodiment of the composition is effective in 80% of humans to show a decrease of about 50% or greater of microbial load in the oral cavity on the sixth day of three times daily administering of the composition. In an embodiment the composition is also effective to reduce a microbial load by 65% to 88% in the oral cavity after the administering step.

The clinical trial of Example 256 further supports the microbial load reduction data, and shows that by following the daily administration regimen, the risk of becoming sick with a disease is greatly reduced.

For example, by taking an embodiment of the composition, for example, for the extended dosage regimen mentioned above, the mammal has increased protection, i.e. is prevented to a degree from getting infected and becoming sick with a disease caused by infectious microorganisms. In an embodiment, the risk of infection with a disease went down by up to about 60% versus placebo by following the dosage regimen, for example a reduction in the frequency of infection from a disease, including reinfection by the same disease or additional diseases was about 55% to about 25%, or about 50% to about 1% versus placebo.

The clinical trial data in Example 256 not only provides data supporting effectiveness of the composition to substantially reduce the chances of getting sick (i.e. prevention of disease), but also to reduce the duration, frequency, and severity of symptoms of diseases, specifically upper respiratory diseases. In addition, a person who is already sick and being treated for symptom reduction may also benefit from the prevention aspect of the composition to avoid becoming ill with a second disease, particularly when the immune system is already strained in combatting the pre-existing illness.

The mucosa that is treated with the composition, may, for example, be a mucosal surface in the oral cavity, the nasal cavity, throat, or the pharyngeal cavity, such as, the nasopharynx (epipharynx), the oropharynx (mesopharynx), or the laryngopharynx (hypopharynx). Beneficial results may also be gained by treating mucosa in other orifices of a mammal, including, but not limited to the ear canal and nasal passages.

In an embodiment, the barrier-forming composition is administered to a skin or mucosal lesion. Subsequent dosages may be applied in accordance with dosage intervals discussed above. In an embodiment, the dosing regimen to the skin or mucosal lesion is ended when the lesion has healed, i.e. when it is covered with new skin or mucosal tissue or when the disease is cured or no symptoms are experienced.

In an embodiment of the method, the step of administering the barrier-forming composition occurs in response to one of the following conditions: (a) being diagnosed with a disease caused or aggravated by microorganisms, (b) feeling symptoms of the disease, or (c) after (a) and (b) and also shortly before or during an encounter with a contaminated environment or contamination event where exposure to a higher microbial load is present. In some situations, the minimum dosing interval may not be followed, such as persons in advanced stages of cancer or AIDs, or an individual that is in critical or a life-threatening condition. In an embodiment, the mammal being treated has been experiencing symptoms from about 1 to about 48 hours prior to the administering step, such as about 2 hours to about 36 hours, or after about 24 hours of first experiencing symptoms from the disease. In another embodiment, the mammal may have been experiencing symptoms for a long term prior to the administration of the composition, including more than a week, or more than a month.

A contaminated environment includes the environments discussed below as presenting an elevated risk of exposure to a higher microbial load.

A contamination event includes events such as an individual sneezing, coughing, or vomiting, or more generally where bodily fluids or matter have been deposited. In an embodiment, the contamination event is in the vicinity of the individual to trigger the administering response. The vicinity of the individual may be defined as being in the same room, vehicle, or within about 10 yards of the individual.

The barrier-forming composition is particularly useful for individuals that have an elevated risk condition. For example, an elevated risk of being exposed to harmful viral, bacterial, or fungal microorganisms; a condition causing an elevated risk of infection from viral, bacterial, or fungal microorganisms; or an elevated risk of serious complications resulting from an infection caused by viral, bacterial, or fungal microorganisms. For example, the method and composition described herein may be particularly useful when a human, or more generally, a mammal, has a disrupted skin or mucosa or has a condition resulting in an immunocompromised state or is otherwise at a greater risk for infection. Such persons may benefit from administration of the barrier-forming composition in repeated doses for ongoing reduction in overall microbial load, prevention of disease, and reduction in duration or severity of disease, or reduction in duration, frequency, or severity of symptoms. In an embodiment, the administration may be in response to identification of a contaminated environment or observation of a contamination event.

Various conditions that cause an elevated risk of infection from viral, bacterial, or fungal microorganisms include, but are not limited to: having an immune system that has been impaired by disease or medical treatment, being the recipient of a transplant, such as an organ transplant, a skin graft, or a bone marrow transplant, having undergone surgery within 30 days, undergoing ventilator treatments, having HIV, AIDS, cystic fibrosis, cancer, COPD, or diabetes, having lesions on the skin or mucosa, or having a condition that causes lesions on the skin or mucosa.

In addition, certain medical conditions are known to cause an increased incidence of skin or mucosal lesions. For example, sexually transmitted diseases, including but not limited to HIV and AIDS, cancer, psoriasis, acne, diabetes, and lupus.

The elevated risk condition may be due to an elevated risk of serious complications resulting from an infection caused by viral, bacterial, or fungal microorganisms. The elevated risk may, for example, be due to, but not limited to, one or more of the following conditions: being immunocompromised in general, undergoing chronic steroid treatment, being under 19 and undergoing long-term aspirin treatment, being morbidly obese, being pregnant, being 65 years of age or older, children younger than two years of age, HIV, AIDS, cancer, metabolic disorder, mitochondrial disorder, liver disorder, kidney disorder, asthma, blood disorders, endocrine disorders, heart disease, chronic lung disease, cerebral palsy, epilepsy, stroke, muscular dystrophy, and spinal cord injury.

In another elevated risk condition, the individual has an elevated risk of exposure to harmful microorganisms for prolonged periods of time, such as every day for a period of time, or at least four or five days a week. In this elevated risk category, the individual does not necessarily have any elevated risk to getting infected once exposed to harmful microorganism or to having complications once infected, but instead has a higher risk of exposure to harmful microorganisms and/or a higher microbial load. In an example, the risk of exposure is elevated due to the individual living or working on an airplane, train, bus, ship, boat, in a school, a library, a dormitory, a hotel, an apartment building, a courthouse, a correctional facility, an airport, a restaurant, a movie theater, a theater, a mall, a retail establishment, a special event arena, a special event stadium, a religious gathering place, a nursing home, hospital, other health-care facility, an office, or day-care facility.

The contaminated environment may include, for example, a public transportation vehicle, a public gathering place, and a room or vehicle containing a mammal known or expected to be ill, or a close proximity to a mammal known or expected to be ill. More information on environments commonly recognized as contaminated environments, such as an airplane, a nursery, and a health center, is disclosed in Yang, et al., "Concentrations and Size Distributions of Airborne Influenza A Viruses Measured Indoors at a Health Centre, a Day-Care Centre, and on Aeroplanes," J.R. Soc. Interface (Feb. 7, 2011), which is incorporated herein by reference.

More specifically, in an embodiment, the public transportation vehicle may be, for example, an airplane, a bus, or a taxi. A public gathering place may be, for example, a doctor's office, a hospital, a school, a nursery, a church, a hotel, or a restaurant. The close proximity to a mammal known or expected to be ill may be, for example, within a one foot radius, or in the same motor vehicle with the mammal. A publicly used airplane may be mentioned as a common and particularly noteworthy example of an environment that many would identify as being a contaminated environment. As such persons that work on airlines or travel on public airplanes very frequently, e.g. two or three times per week may be considered to have the elevated risk condition due to increased exposure to microrganisms.

In an embodiment, the elevated risk may be due to participation in activity related treatments, such as, for example, ventilator use (which would include medical devices related to the ventilator and contacting the patient). In an embodiment the contaminated item is a medical apparatus, or a dental apparatus. Having exposure to of a medical or dental device such as a ventilator may be considered as both an elevated risk of exposure and an elevated risk of infection. A nosocomial infection wherein an individual is already in an immunocompromised state and also is present in a hospital or other health-care facility environment may also be considered as an elevated risk of exposure and either one or both of an elevated risk of infection and an elevated risk of serious complication.

In vitro testing demonstrates that embodiments of the barrier-forming composition prevent all active bacteria from reaching the other side of the barrier for long periods, including about two hours or more, about six hours or more, about sixteen hours or more, and about twenty-four hours or more. In vitro testing shows that in viruses exposed to embodiments of the barrier-forming composition, growth may be inhibited for about two or more days (such as influenza), up to about nine days, (such as HIV), after which the viral count is still below the MIC for extended periods, such as about two or three additional days Inhibitory activity against influenza virus was observed for up to 48 hours.

The barrier-forming composition exhibited the activity to reduce the microbial load of humans in clinical trials. For example, a surprisingly effective reduction in microbial load of more than about 25% to about 99% from about one to about six hours after the administering step was demonstrated, such as about 33% to about 95%, or about 50% to about 90%. In embodiments, the microbial load may be reduced by more than about 10%, by more than about 25%, or by more than about 70% from about one to about six hours after the administering step. Furthermore, these ranges of reduction in microbial load are sustainable for long periods of time with the disclosed dosing regimen.

Figure 1:
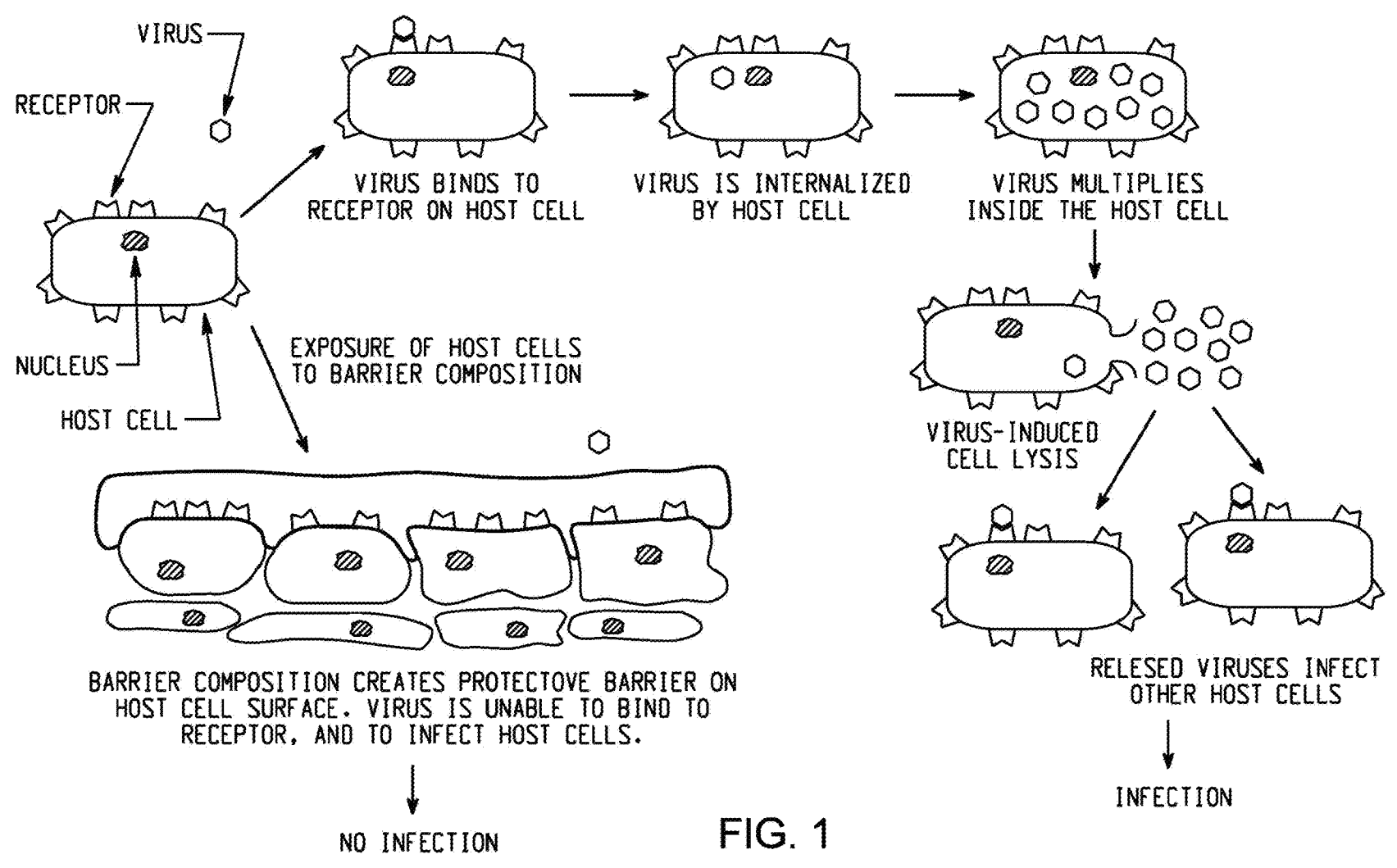

In an embodiment that illustrates a proposed mechanism of the barrier-forming composition in such a case, shown in FIG. 1, the barrier-forming composition provides anti-viral activity. When a virus comes into contact with a cell, it will bind to receptors on the host cell. Over time, 5 to 6 hours, or so, the virus is internalized by the host cell, the virus multiplies inside the host cell, and it induces cell lysis causing additional virus particles to infect other host cells.

In contrast, in a cell treated with the barrier-forming composition, a protective barrier is on the surface of the host cell. The barrier, which is thick enough to cover the cell and any receptors on the cell, prevents the virus particle from binding to the cell receptors. Thus, infection and lysis is also prevented. The barrier-forming composition retains the barrier for a long duration, such as a duration of about 1 hour of more, a duration of about 2 hours or more, a duration of about 6 hours or more, a duration of about 16 hours or more, a duration of about 16 hours to about 24 hours, or a duration of about 24 hours or more, thereby protecting host cells and preventing infection. The cidal or static antimicrobial activity is also retained for a long duration, such as about 2 hours or more, about 6 hours or more, about 16 hours or more, about 24 hours or more, or about 48 hours or more, thereby killing microorganisms and reducing microbial load These durations are applicable for viruses, bacteria, and fungi. By preventing contact with cell receptors by live harmful microorganisms, it is theorized that the body's inherent infection fighting mechanisms are freed up to concentrate on already existing infection in the body.

Harmful microorganisms are those known to cause or aggravate disease such as, for example, communicable diseases caused by microorganisms, such as *Candida* species (e.g. *C. albicans, C. glabrata, C. krusei, C. tropicalis*), *Staphylococcus* species (including methicillin-resistant *S. aureus*, MRSA), *Streptococcus* species (e.g. *S. sanguis, S. oxalis, S. mitis, S. salivarius, S. gordonii, S. pneumoniae*), *Acinetobacter baumannii, Aggregatibacter actinomycetemcomitans, Fusobacterium nucleatum*, and other microorganisms such as microorganisms that cause upper respiratory infections, microorganisms that cause lower respiratory infections, and common cold (rhinovirus) and influenza viruses and *Pneumonia, P. gingivalis, Y. enterocolitica, Acinetobacter bumanii, Aggregatibacter actinomycetemcomitans, Clostridium difficile, Bordetella pertussis, Burkholderia, Aspergillus fumigatus, Penicillium* spp, *Cladosporium, Klebsiella pneumoniae, Salmonella choleraesuis, Escherichia coli* (0157:H7), *Trichophyton mentagrophytes, Rhinovirus* Type 39, Respiratory Syncytial Virus, Poliovirus Type 1, Rotavirus Wa, Influenza A Virus, Herpes Simplex Virus Types 1 & 2, and Hepatitis A Virus. In an embodiment, the barrier-forming composition and method of treatment described herein may be useful, for example, for treatment of sexually transmitted diseases such as, for example, infections caused by human immunodeficiency virus (HIV), Herpes simplex, or human papilloma virus (HPV).

The barrier-forming composition has shown effectiveness against microorganisms with a diameter of, for example, about 30 nm or greater, such as about 100 nm (HIV, spherical), about 100 to about 300 nm (influenza, spherical and elongated forms), about 120 nm to about 260 nm (EBV spherical/disk forms), and about 30 nm (rhinovirus, spherical). Thus, the barrier composition should also be effective against other microorganisms with diameters of about 30 nm, or greater than about 30 nm.

The barrier-forming composition has even shown powerful and surprising activity inhibiting biofilms, which can be very difficult to eradicate. In an embodiment, the method comprises administering the barrier-forming composition to a formed biofilm on a mucosa or lesion.

The microorganisms may be air-borne microorganisms. In an embodiment, the microorganisms are those that cause communicable diseases. In an embodiment, the microorganisms do not include those that cause allergic reactions or dental problems, such as, for example, cavities (caries), gingivitis, or seasonal allergies. Similarly, in an embodiment, the method of treatment does not solely or additionally treat dental problems or allergic reactions, such as, for example, cavities (caries), gingivitis, or seasonal allergies.

In another embodiment, however, microorganisms, such as fungi that may generally be classified as allergens, other allergens, and airborne irritants to the mucosa, are also blocked by the barrier and the method.

A therapeutically effective amount of the barrier composition includes an amount that is enough to coat the targeted mucosa or lesion with the barrier-forming composition to form a barrier coating that will result in a barrier layer forming on the mucosa or lesion. For example, about 100 microliters to about 10 ml, such as, for example, about 1 ml to about 8 ml, or about 2 ml to about 5 ml for a mouthwash formulation, or about 0.125 ml to about 2 ml, such as about 0.5 ml to about 1 ml for a spray formulation. The dosage amount may also be expressed in terms of a volume per square cm, such as, for example, from about 0.5 to about 50 µl/cm$^2$, such as, about 5 to about 40 µl/cm$^2$, or about 10 to about 25 µl/cm$^2$ for a mouthwash formulation; or for a spray formulation, for example, about 0.625 to about 10 µl/cm$^2$, such as, about 2.5 to about 5 µl/cm$^2$. Other delivery mediums, such as dissolvable strips, may have dosages derived from these ranges given the adjustments for concentrations and other factors known to those of skill in the art. In addition, the average thickness of the film formed on the mucosa from the barrier-forming composition may range, for example, from about 0.001 to about 0.2 mm, such as about 0.01 mm to about 0.1, or about 0.08 to about 0.15 mm. For example, for a given human or animal, the therapeutically effective amount can be determined based on the age or weight or size of the mammal to be treated, and the dosage may be those listed above. For non-human mammals, in particular, the dosage amount may be adjusted according to the per square cm values given above and the approximate surface area of the mucosal surface or body cavity to be treated.

Other delivery mediums, such as a liquid filled lozenge, wiping the composition directly on the mucosa, spoon or cup liquids to be swallowed, may have dosages derived from these ranges given the adjustments for concentrations and other factors known to those of skill in the art.

The average thickness of the film or coating formed on the mucosa or mucosal or skin lesion surface from the barrier-forming composition may range, for example, from about 0.001 to about 0.2 mm, such as about 0.01 mm to about 0.1, or about 0.08 to about 0.15 mm.

A mechanical pump spray or an aerosolized spray device may be used. In the aerosolized embodiment, the barrier-forming composition may be mixed with common propellant agents, such as $CO_2$, nitrogen, and hydrocarbons. A bag-on-valve embodiment may also be used; however, the composition is stable enough so as not to require a separation of the propellant agent and the composition components.

An applicator, including but not limited to, a roll-on applicator, may be used with a dosage derived from the stated ranges given the adjustments for concentrations and other factors known to those of skill in the art.

A wipe, bandage or other applied material that is pre-treated with the barrier technology may be used, which is then applied directly to the affected area, including disrupted mucosa. These may have dosages derived from the stated ranges given the adjustments for concentrations and other factors known to those of skill in the art.

In an embodiment, the barrier-forming composition comprises a carbohydrate gum (C), a humectant (H), and an antimicrobial agent (A), and the barrier-forming composition meets the following requirements:
about 0.0001%≤C≤about 0.4%;
about 0.07%≤H≤about 70%; and
0.0005%<A
or
about 0%≤C≤about 0.4%;
about 55%≤H≤about 70%; and
0.0005%<A All percentages are by weight of the total composition. The ranges in this embodiment reflect the demonstrated effectiveness of the germ killing power of the barrier-forming composition at very low dilutions against many microorganisms reported in MIC experiments in Table V below. After effective application, the barrier layer has antimicrobial cidal or static activity.

In another embodiment the barrier-forming composition meets the following requirements:
about 0.01%≤C≤about 0.4%;
about 4.5%≤H≤about 65%; and
0.0005%<A
or
about 0%≤C≤about 0.4%;
about 55%≤H≤about 65%; and
0.0005%<A All percentages are by weight of the total composition.

In another embodiment, the humectant of the barrier-forming composition meets the following requirements: about 0.07%≤H<1%. This low-humectant embodiment reduces the stickiness of the composition.

In an embodiment, the barrier-forming composition includes glycerin or one or more similar humectant substances. In an embodiment, the concentration of the humectant may range from about 0.07% to about 10% of the entire composition (by weight), such as about 3% to about 8%, 0.35% to less than 1%, or about 0.1% to less than 0.5%. In another embodiment, the humectant may range from about 2% to about 70% weight percent of the entire composition, such as, for example, about 4.5% to about 65%, about 7% to about 35%, or about 15% to about 45%. Humectants similar to glycerin may be classified generally as polyols. The humectants may be, for example, glycerin, sorbitol, xylitol, propylene glycol, polyethylene glycol, and mixtures thereof. In an embodiment, glycerin may be used at high concentrations such as about 55% to about 65% in the absence of a gum.

In an embodiment, the composition also includes a gum. The gum may be, for example, a polysaccharide, xanthan gum, gum Arabic, or guar gum. Such gums may be generally classified as carbohydrate gums that have an overall negative charge. In another embodiment, the gum may be, for example, xanthan gum, guar gum, gum Arabic, tragacanth, gum karaya, locust bean gum, carob gum, and pectin. These gums may also be generally classified as carbohydrate gums that have an overall negative charge. In an embodiment, the gum may be present in a weight percentage of the total composition ranging from about 0.0001% to about 0.4%, such as about 0.0005 to about 0.25%. In another embodiment, the gum may be present in a weight percentage of the total composition ranging from about 0.01% to about 0.4%, such as for example, about 0.25% to about 0.35%, about 0.05% to about 0.25%, or about 0.4%.

In an embodiment, the barrier composition comprises a humectant, an antimicrobial, and optionally a gum, wherein the gum, if present, is present in an amount of about 0.0001% to about 0.4% by weight of the total barrier-forming composition.

In an embodiment, an antimicrobial agent is present in the composition. For example, the composition may include one or more anti-viral agents, or antifungals or antibacterials or a combination thereof. In addition, the effect of such antimicrobials includes static and/or cidal activity.

The antimicrobial agent may include, but is not limited to cationic antimicrobial agents and pharmaceutically acceptable salts thereof, including, for example, monoquaternary ammonium compounds (QAC, cetrimide, benzalkonium chloride, cetalkonium chloride, cetylpyridinium chloride, myristalkonium chloride, Polycide), biquaternaries and bis-biguanides (Chlorhexidine, Barquat, hibitane), and biguanides, polymeric biguanides, polyhexamethylene biguanides, Vantocil, Cosmocil, diamidines, halogen-releasing agents including chlorine- and iodine-based compounds, silver and antimicrobial compounds of silver, peracetic acid (PAA), silver sulfadiazine, phenols, bisphenols, hydrogen peroxide, hexachloroprene, halophenols, including but not limited to chloroxylenol (4-chloro-3,5-dimethylphenol; p-chloro-m-xylenol).

In addition, the antimicrobial may also be or include: antibacterial agents, both cidal and static, and different classes, for example tetracycline, chloramphenicol, fusidic acid, fluoroquinolone, macrolide antibacterial agents, oxazolidinones, quinolone- and naphthyridone-carboxylic acid, citral, trimethoprim and sulfamethoxazole (singly and combined), aminoglycoside, polymyxin, penicillins and their derivatives. In addition, the antimicrobial may also include, for example: antifungal agents in the following classes: azoles, polyenes, echinocandins, and pyrimidines. Combinations of any of the foregoing antimicrobial agents are also contemplated. Many of the foregoing are cationic species or their pharmaceutically acceptable salts, and in an embodiment, cationic antimicrobials are utilized in the composition. In an embodiment the composition is exclusive of agents that release gas fumes, such as, for example, chlorine dioxide, or chlorine dioxide producing reactants.

In an embodiment, the antimicrobial is a broad-spectrum antimicrobial. In an embodiment, the antimicrobial is soluble in aqueous solution. In an embodiment, the antimicrobial activity is achieved through binding to the cell membrane of the pathogen (bacteria, virus, and fungi), disrupting it and leading to loss of important cellular material, cell collapse, and death. In an embodiment, the antimicrobial does not function through selective cell receptor mimicking, such as in anti-adherence compositions. In an embodiment, the antimicrobial does not function through nanoemulsion activity. In an embodiment, the composition is not an emulsion.

In an embodiment, the barrier-forming composition does not induce mutations or the development of resistance by microbes. This is because of the mechanism of action against the microorganisms by the barrier and the selected antimicrobial.

The antimicrobial may be present, for example, in an amount ranging from about 0.0005% to 5% by weight of the total composition, such as, for example, about 0.0025% to about 1%, about 0.005 to about 0.006%, or about 0.0006% to about 0.003%. In another embodiment, the antimicrobial may be present, for example, in an amount ranging from about 0.05% to about 0.1% by weight of the total composition, such as, for example, about 0.05% to about 0.06% or about 0.06% to about 0.1%. In an embodiment, the antimicrobial is about 5% or less, or about 3% or less, or about 1.5% or less, such as when the antimicrobial used does not cause solubility problems at higher concentrations.

In embodiments, the composition may further include other components, such as, for example, copovidone and other lubricating agents, parabens such as methyl paraben or propylparaben, scenting agents, preservatives, such as sodium benzoate, buffering agents, such as monosodium and disodium phosphate, sweeteners, hydrogenated castor oil with ethylene oxide, and carboxymethylcellulose. These components may, for example, be included in amounts ranging from about 0.01% to about 5% by weight of the total composition, such as, for example, about 0.1% to about 2%. In another embodiment, the components are included, for example, in amounts of about 0.0001% to about 0.05%. Buffering agents (such as monosodium or disodium phosphate) may also be used.

In an embodiment, the composition may include additional active agents for treating diseases or relieving or treating symptoms of diseases, such as upper respiratory disease symptoms, so long as such agents do not conflict with the efficacy of the antimicrobial agent. In an embodiment, active agents that may be used in the barrier forming composition are those that have a delayed- or sustained-release property, or otherwise have improved effectiveness the longer they are present on the body surface. Example active agents include antacids, vitamins, nutraceuticals, silver, anti-oxidants, cold and flu symptom medicaments, immunostimulators, or combinations of the above.

In an embodiment with an antacid active agent in addition to the antimicrobial, the barrier-forming composition is used for treatment of acid reflux or an excess of acid which may be caused or related to various diseases. Example antacid active agents include calcium and magnesium carbonate, magnesium and aluminum hydroxide, sodium carbonate and bicarbonate, and $C_7H_5BiO_4$, and mixtures thereof.

In an embodiment with a nutraceutical active agent in addition to the antimicrobial, the barrier-forming composition is used for treatment of various conditions. Example nutraceuticals include resveratrol from red grape products, flavonoids inside citrus, tea, wine, and dark chocolate, anthocyanins found in berries, soluble dietary fiber products, such as psyllium seed husk, broccoli (sulforaphane), fiddleheads (*Matteuccia Struthiopteus*), soy or clover (isoflavonoids), alpha-linolenic acid from flax or chia seeds, Omega 3 fatty acids in fish oil, botanical and herbal extracts such as ginseng, and garlic oil.

In an embodiment with an antioxidant active agent in addition to the antimicrobial, the barrier-forming composition is used for treatment or reduction of symptoms of various diseases. Example anti-oxidants include thiols, carotene, ubiquinol, ascorbic acid, or polyphenols and may be either hydrophobic or hydrophilic.

In an embodiment cold and flu medicaments are active agents in the barrier-forming composition in addition to the antimicrobial, and the composition is used for treatment of cold and flu symptoms. Example medicaments include decongestants, anti-diarreahals, anti-nausea, and antihistamines, further details of which are listed herein separately.

In an embodiment with an immunostimulant active agent in addition to the antimicrobial, the barrier-forming composition is used for stimulating the body's immune system in addition to reducing the microbial load, thereby reducing the duration of the disease and/or relieving the symptoms. Example immunostimulants include specific, and non-specific immunostimulants, endogenous immunostimulants, deoxycholic acid, a stimulator of macrophages, synthetic immunostimulants, macrokine, imiquimod, resiquimod, and granulocyte macrophage colony-stimulating factor.

In an embodiment with an anti-diarrheal active agent in addition to the antimicrobial, the barrier-forming composition is used for treating diarrhea and diseases related to or causing diarrhea. Example anti-diarrheal active agents include, for example, anti-inflammatory solutions like bismuth subsalicylate, bulking agents like methylcellulose, guar gum or plant fiber (bran, sterculia, isabgol, absorbents such as methyl cellulose, opioids, and loperamide hydrochloride.

In an embodiment with an antiemetic active agent in addition to the antimicrobial, the barrier-forming composition is used for treating nausea and diseases causing or related to nausea. Example anti-nauseant active agents include, for example, olanzapine, 5-HT3 receptor antagonists, dopamine antagonists, dolasetron, NK1 receptor antagonist, aprepitant, H1 histamine receptor antagonists, cyclizine, diphenhydramine, cannabinoids, *cannabis*, dronabinol, benzodiazepines, midazolam, lorazepam, anticholinergics, hyoscine, steroids, dexamethasone.

In an embodiment with an analgesic active agent in addition to the antimicrobial agent, the barrier-forming composition is used for reducing pain in the oral or pharyngeal region caused by or related to an infectious disease, such as, for example, strep throat. Example analgesics include: propionic acid derivatives, naproxen, ibuprofen, acetic acid derivatives, indomethacin, etodolac, enolic acid derivatives, fenamic acid derivatives, Cox-2 derivatives, acetaminophen, sulphonanilides, diclofenac, capsaicin, NSAIDs, ibuprofen, trolamine salicylate or methyl salicylate, MENTHACIN and ZOSTRIX.

In an embodiment with a decongestant active agent in addition to the antimicrobial agent, the barrier-forming composition is used for relief of excess mucous and disease causing or related to congestion. Example decongestants include: pseudoephedrine, phenylephrine, ephedrine, levo-methamphetamine, naphazoline, oxymetazoline, phenylpropanolamine, propylhexedrine, synephrine, and tetrahydrozoline.

In an embodiment with a cough suppressant agent in addition to the antimicrobial agent, the barrier-forming composition is used for relief of coughing and diseases causing by or related to coughing. Example cough suppressants include: antitussives, dextromethorphan, codeine, noscapine, bromhexine, acetylcysteine, expectorants, mucolytics, and honey.

In an embodiment with an expectorant agent in addition to the antimicrobial agent, the barrier-forming composition is used for relief of mucous in the upper respiratory system and diseases that cause or are related to the same. The composition may be applied, for example, to the nasal, oral, or pharyngeal mucosa. The composition can be sprayed, rolled, or otherwise dispersed onto the mucosa. Example expectorants include: acetylcysteine, ambroxol, and guinefesin.

In an embodiment with an anti-histamine agent in addition to the antimicrobial agent, the barrier-forming composition is used for relief of mucous in the upper respiratory system and diseases that cause or are related to the same. The composition may be applied, for example, to the nasal, oral, or pharyngeal mucosa, or in another embodiment in the eyes or ears. The composition can be sprayed, rolled, dropped, or otherwise dispersed onto the mucosa. Example anti-histamines include: azelastine, hydroxyzine, desloratadine, cyproheptadine, emadastine, levocabastine, carbinoxamine, levocetirizine, fexofenadine, diphenhydramine, brompheniramine, loratadine, clemastine, chlorpheniramine, and certirizine.

Purified water and/or alcohol may be used as the diluent component of the composition. In an embodiment, the barrier-forming composition is a free-flowing liquid suitable for spraying. This is in contrast to a paste or toothpaste composition, which is typically not free-flowing and not suitable for spraying. In addition, in an embodiment, the barrier-forming composition is free of abrasives that are commonly used in toothpaste compositions.

In an embodiment, the composition consists essentially of only the gum, the humectant, and the antimicrobial, such as, including only preservatives, scenting agents, or other agents, that do not affect the barrier or antimicrobial activity of the composition. "Consists essentially of" or "consisting essentially of" as used herein has the meaning that is typically applied, that is, it means, the specified materials and those that do not materially affect the basic and novel characteristic(s) of the composition.

In an embodiment, the composition is exclusive of agents for acting against the teeth and/or gums, including, for example, abrasives (such as those used in toothpastes) teeth whitening or desensitizing agents. In an embodiment, the composition is exclusive of cellooligosaccharides. In an embodiment, the antimicrobial agent is exclusive of lipids such as fatty acid ethers or esters of polyhydric alcohols or alkoxylated derivatives thereof. In an embodiment, the composition is exclusive of one or more of time-release agents, allergy-relief compounds, azelastine, silicon based oils, essential oils, polyvinyl pyrrolidone, polyvinyl alcohol, and potassium nitrate. In an embodiment, the composition is free of volatile organic compounds, including for example, volatile alcohols. In an embodiment, the composition is free of surfactant or foaming agent. For the avoidance of doubt, none of the above should be construed to mean that all embodiments are exclusive of these compounds.

In an embodiment, a method for making a barrier-forming composition includes mixing and heating the carbohydrate gum, humectant, and antimicrobial agents. In an embodiment, heating is replaced with extended mixing times. Other components may also be mixed in a single or multiple mixing steps. All components of the barrier-forming composition may be mixed at one time to produce a composition with a stable shelf life, such as, for example, being stable for over about 6 months, such as stable for about 1 year to about 3 years, or about 1.3 to about 2 years. This is in contrast to compositions that have active components that must be added separately a short time prior to use, or those that will separate out of solution. Thus, in an embodiment, the barrier-forming composition is a stable one-part composition that does not require mixing with a second composition to activate it for use. In an embodiment, the barrier-forming composition is in a single phase and is not an emulsion.

In an embodiment, the composition is liquid and is non-foaming.

As mentioned above, in an embodiment, the composition is suitable for spraying, and thus also has a viscosity that is suitable for spraying. In an embodiment, the composition has a viscosity of less than 500 cps such as, for example, about 490 cps to about 10 cps, or about 400 cps to about 15 cps. In another embodiment, the composition has a viscosity of about 16 to about 20 cps, such as, for example, about 17 to about 19 cps.

In an embodiment, the composition is substantially free-flowing and substantially free of clumps. In an embodiment, substantially free-flowing and substantially free of clumps is judged by passing the composition through a 140 U.S. mesh (0.10 mm pore size), and 95 to 100% of the composition, such as 96% to 99.9% passes through, after 30 seconds.

In an embodiment, the composition is non-toxic to humans, wherein at least a portion of the composition may be ingested and is safe and non-toxic for human consumption, such as, for example, about 1 mL per day to about 30 mLs per day, such as about 2 mLs per day to about 8 mLs per day, or about 2.5 mLs to about 7.5 mLs. The composition is also non-flammable.

Without being bound by theory, the barrier-forming composition is not hydrophilic which allows the barrier-forming composition to have a greater affinity to adhere to and cover certain surfaces. Furthermore, in an embodiment, the antimicrobial being embedded in the non-hydrophilic composition will allow for sustained antimicrobial activity on treated surfaces. In an embodiment the barrier-forming composition is amphiphilic or has amphiphilic components.

One measure of hydrophilicity is the Rf (relative front) value, determined by chromatography in water. In an embodiment, the composition has an Rf value in water of 0 to about 0.25, such as about 0.0001 to about 0.15, or about 0.03 to about 0.1.

In an embodiment, the composition has a pH of about 4 to about 8, such as about 5 to about 7, or about 6 to about 7.5. In another embodiment the composition has a pH of greater than 5.5 to about 8, wherein antimicrobials such as cetylpyridinium chloride are most effective.

In general, the dual-action mechanism of providing a barrier from microorganisms and an antimicrobial agent provides a long-lasting effect, characterized by both in vitro, simulated in vivo, and in vivo examples below. In in vivo examples, the barrier-forming composition was shown to have antimicrobial effect (cidal or static) for at least 6 hours. The barrier property itself was tested in simulated in vivo tests (on artificial human mucosa EHOMs), which indicated the barrier itself had a significantly extended duration past 6 hours, such as greater than about 8 hours, about 6 to about 16 hours, and about 24 hours, or more. In addition, in vitro tests indicate the antimicrobial effect had a significantly extended duration past about 2 hours, past about 6 hours, and depending on the microorganism tested, greater than about 8 hours, about 6 to about 16 hours, and about 24 hours, or more.

Post antimicrobial effect (PAE) is defined as suppression of microbial growth that persists after limited exposure to an antimicrobial agent. Having a longer PAE is considered advantageous for antimicrobial agents as it allows for persistent inhibition of microbial growth, and may affect dosing regimens as agents with long PAEs may need less frequent administration than those with short PAEs.

In embodiments of the method and composition disclosed herein the PAE of the composition when applied to a mucosa has a PAE that persists for about 6 hours or more, such as about 6 hours to about 16 hours, or about 16 hours to about 24 hours.

As the Examples below show, the barrier-forming composition has been shown to block (by trapping) the passage of a wide variety of representative fungi, bacteria and viruses and also kill a broad spectrum of microorganisms (viruses, bacteria, and fungi). Because viruses are amongst the smallest infectious microorganisms, and because the barrier-forming composition forms a mechanical barrier blocking viruses, it is expected that the barrier-forming composition would be an effective treatment not only for viruses but also for larger microorganisms, including a wide range of bacteria and fungi.

Several experiments were performed to assess the safety of the composition on mammals and the ability of the spray formulation to form a protective barrier on an Engineered Human Oral Mucosa (EHOM) model. The experimental evidence showed that the composition formed a barrier over tissues, which prevents microorganisms from penetrating into the tissues.

The clinical trial examples, show reduction in microbial load, prevention of disease, and reduction in symptom duration, severity, and frequency vs. placebo.

EXAMPLES

Example 1

Human Gingival Epithelial Cell and Fibroblast Cultures

Normal human gingival cells (epithelial cells and fibroblasts) were obtained from ScienCell Research Laboratories (Carlsbad, Calif., USA). The fibroblasts were cultured in Dulbecco's modified Eagle's medium (DME, Invitrogen Life Technologies, Burlington, ON, Canada) supplemented with fetal bovine serum (FBS, Gibco, Burlington, ON, Canada) to a final concentration of 10%. The epithelial cells were cultured in Dulbecco's modified Eagle's (DME)—Ham's F12 (3:1) (DMEH) with 5 µg/mL of human transferrin, 2 nM 3,3',5' of tri-iodo-L-thyronine. 0.4 µg/mL of hydrocortisone, 10 ng/mL of epidermal growth factor, penicillin and streptomycin, and 10% FBS (final concentration). The medium was changed once a day for epithelial cells and three times a week for fibroblasts. When the cultures reached 90% confluency, the cells were detached from the flasks using a 0.05% trypsin-0.1% ethylenediaminetetra acetic acid (EDTA) solution, washed twice, and resuspended in DMEM (for the fibroblasts) or DMEH-supplemented medium (for the epithelial cells).

Example 2

Engineered Human Oral Mucosa (EHOM) Tissue

The EHOM model was produced by using the gingival fibroblasts and epithelial cells of Example 1 that were used to form a complex three-dimensional spatial cellular organization similar to that found in normal human oral mucosa. The lamina propria was produced by mixing Type I collagen (Gibco-Invitrogen, Burlington, ON, Canada) with gingival fibroblasts, followed by culture in 10% FBS-supplemented medium for four days. The lamina propria was then seeded with gingival epithelial cells to obtain the EHOM. The tissue specimens were grown under submerged conditions until the total surface of the lamina propria was covered with epithelial cells. To produce stratified epithelium, the EHOM was raised to an air-liquid interface for four more days to facilitate the organization of the epithelium into its different strata.

The lamina propria is a thin layer of loose connective tissue that lies beneath the epithelium and together with the epithelium constitutes the mucosa. FIG. 2 shows an illustration of the EHOM mucosal tissue, with an arrow pointing to its location in a schema depicting mucosa covered with the barrier-forming composition.

Examples 3-9

Examples of the barrier-forming compositions were created by adding the ingredients listed below in a 50-mL centrifuge tube, and vortexing to bring to "free-flow" consistency. The constituents of the compositions and their approximate amounts are given in Table I (the values in Table I are percentages by weight of the total composition):

TABLE II

| | Example 3 | Example 4 | Example 5 (control) | Example 6 (control) | Example 7 | Example 8 | Example 9 |
|---|---|---|---|---|---|---|---|
| Glycerin | 7 | 35 | 35 | 35 | 35 | 7 | 7 |
| Xanthan Gum | 0.01 | 0.4 | 0.4 | 0.4 | 0.4 | 0.01 | 0.01 |
| Cetyl Pyridinium Chloride | 0.05 | 0.05 | | | 0.1 | 0.06 | 0.05 |
| Preservatives | No | No | No | Yes | Yes | Yes | Yes |

*Purified water comprised the remaining portion of the composition.
**Preservatives included methylparaben (0.1%), propylparaben (0.1%), sodium benzoate (0.5%)

Based on the results below, the preservatives were found to be superfluous to the barrier formation and antimicrobial activity.

Examples 10-26

Examples 10-26 were performed to demonstrate safety of the composition on mucosal surfaces. Prior patent publication U.S. 2012/0270909, as well as the provisional applications that this application claims the benefit of priority of, include this information.

Examples 27 and 28

Determination Whether the Barrier-forming Composition Affects Mechanical Barrier Function of EHOM Against Microbial Passage Through Mucosal Tissue In Examples 27 and 28, two approaches were used to determine whether the control Examples formed a barrier that blocked the microbial passage through the mucosal tissues and also had an inherent anti-microbial effect. Growth in pass-through chamber and growth on EHOM surface was assessed by evaluating growth in agar media.

In Example 27, EHOMs of Example 2 were put in contact with 1 and 5% dilutions (diluted in serum free culture medium) of Example 4 for 2 minutes. Tissues were then washed twice with serum free culture medium then over layered with $1\times10^6$ candida microbial cells in a volume of 300 µl. Tissues were then put on air-liquid culture plates and incubated for 24 hours in 5% $CO_2$ humid atmosphere at 37° C. Next, the culture medium underneath the EHOM (ventral chamber) was collected and seeded on Sabouraud agar plate to verify whether or not the microorganisms penetrated through the tissue and reached the culture medium below. A culture was also obtained from the EHOM surface and seeded on Sabouraud agar plate. The process is graphically depicted in FIG. 3.

In Example 28, EHOMs of Example 2 that were treated with 1 and 5% dilutions of the Example 4 composition for 2 minutes were over layered with candida microbial cells for 24 hours were flipped onto Sabouraud dextrose agar plates and left in place for 5 minutes. The EHOMs were then removed and the plates were incubated for 24 hours at 30° C., after which microbial growth was ascertained macroscopically and photographed. Each experiment was repeated 5 independent times with similar results.

Figure 4:
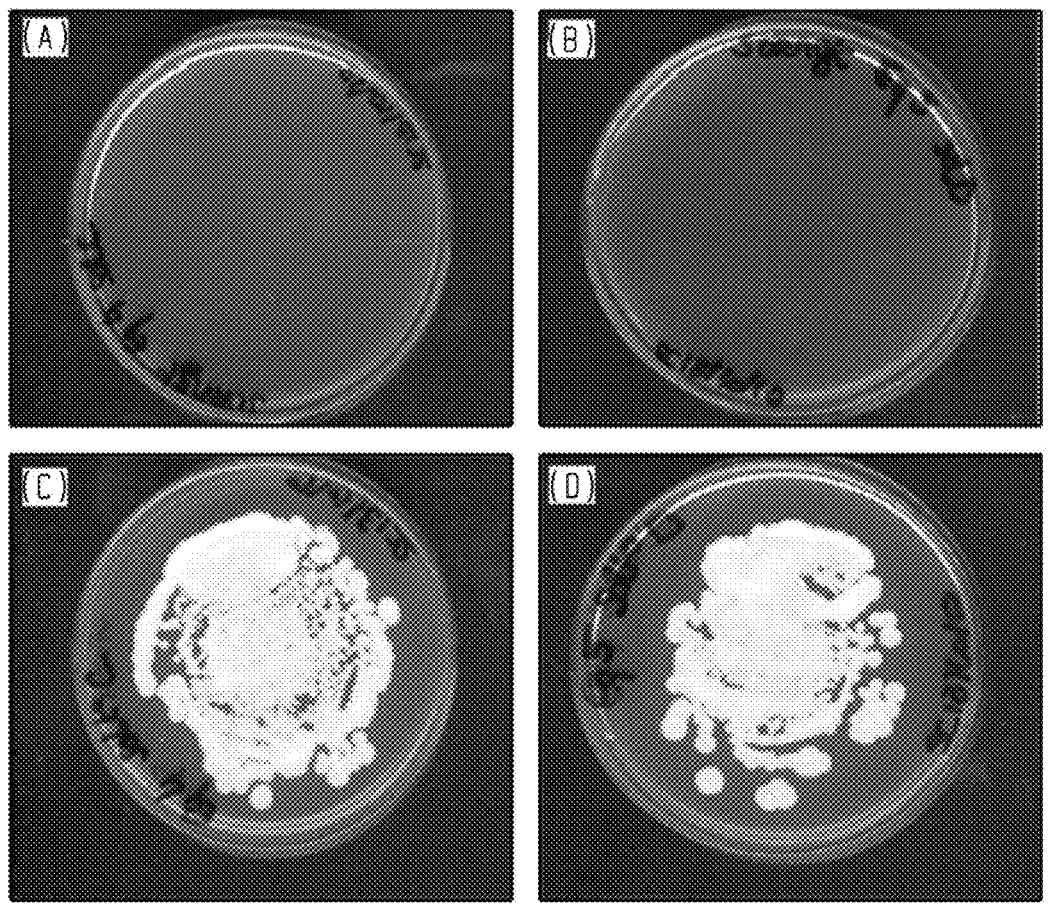
FIG. 4 show photographs of agar media plates showing microbial growth in the upper and lower chambers of an EHOM assay, as described in Examples 27-28.

FIG. 4 shows the results of the cultures of the EHOM surface (panels C and D) and the culture of the pass-through liquid from the bottom (ventral) chamber (panels A and B). The A and C panels were EHOMs treated with a 1% dilution of Example 4, and the B and D panels were EHOMS treated with a 5% dilution of Example 4. This data indicates that Example 4 composition forms a barrier that prevents passage of microbes through the EHOM tissues but does not have an inherent anti-microbial effect.

Examples 29 and 30

In Examples 29 and 30, Examples 27 and 28 were repeated, except the EHOM were infected with S. mutans. Similar results were obtained that indicated that the barrier-forming compositions formed a barrier preventing the S. mutans microbes from passing through the barrier, but did not have an antimicrobial effect.

Examples 31 and 32

Determination Whether the Barrier-forming Composition Affects Mechanical Barrier Function of EHOM Against Microbial Invasion In Example 32, a set of EHOM tissues from Example 2 was treated with the barrier-forming composition of Example 4 and then overlaid with C. albicans. In control Example 31 a control set was not treated with the barrier-forming composition prior to overlayering with C. albicans. Immediately after each contact period, biopsies were taken from each EHOM, fixed with paraformaldehyde solution, and embedded in paraffin. Thin sections (4 µm) were stained with eosin-hematoxylin. Sections were observed using an optical microscope to analyze the invasion/penetration of microbial cells into the tissue. Following microscopic observations, representative photos were taken from each condition and presented. The experiment was repeated three times with similar results. Similar results were also obtained with treatment with Example 3 (data not shown).

Figure 5:
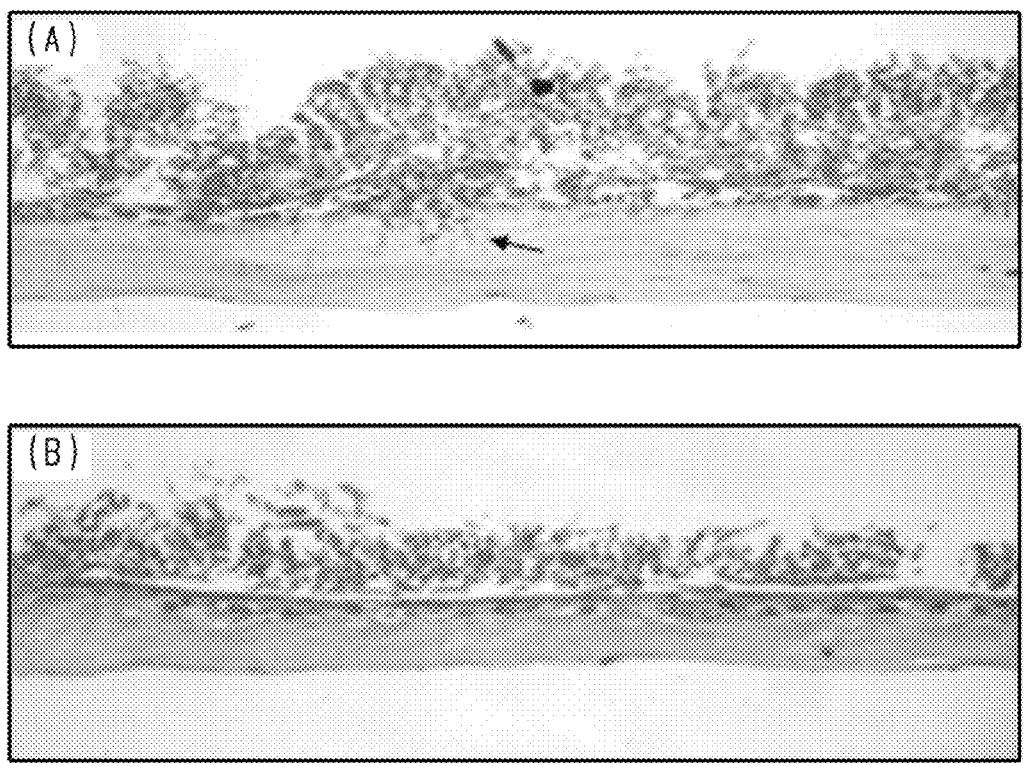
FIG. 5 shows photographs of magnified cross-sections of the barrier-forming composition-treated and untreated engineered human oral mucosa (EHOM) of Examples 31-32.

FIG. 5 shows the effect of the barrier-forming composition on microbial invasion of EHOM tissues. Panel (A) is a representative photograph of the untreated control Example 31, and panel (B) is a photograph of the treated Example 32. The arrow indicates invading fungal hyphae in the untreated control Example 31.

Examples 33-40

The EHOM model described above was also used to evaluate the ability of Examples 5-7 to form a barrier that: (a) prevents oral bacteria (S. mutans) and fungi (Candida albicans) from penetrating/invading human oral mucosa, and (b) does not cause damage to host cells (cytotoxicity assay).

Examples 33-40 were formulated according to Table III below.

TABLE III

| | Barrier-forming composition Pre-Treatment | Microbe Overlay | Figure reference |
|---|---|---|---|
| Example 33 | None | C. albicans | FIG. 6(A) |
| Example 34 | Example 5 | C. albicans | FIG. 6(B) |
| Example 35 | Example 6 | C. albicans | FIG. 6(C) |
| Example 36 | Example 7 | C. albicans | FIG. 6(D) |
| Example 37 | None | S. mutans | FIG. 7(A) |
| Example 38 | Example 5 | S. mutans | FIG. 7(B) |
| Example 39 | Example 6 | S. mutans | FIG. 7(C) |
| Example 40 | Example 7 | S. mutans | FIG. 7(D) |

In Examples 33-40, after pre-treatment and incubation according to the procedures of Examples 27 and 28: (1) the flow-through medium was collected from the lower chamber; and (2) tissues were flipped and placed onto the surface of Sabouraud dextrose agar Petri dishes, and incubated for 24 hours. Collected flow-through media were spread onto agar media plates, and incubated for 24 hours also as described in Examples 27 and 28. Table III also indicates the figure in which a photo of each Example was taken showing the microbial growth on each flipped Example culture.

Figure 6:
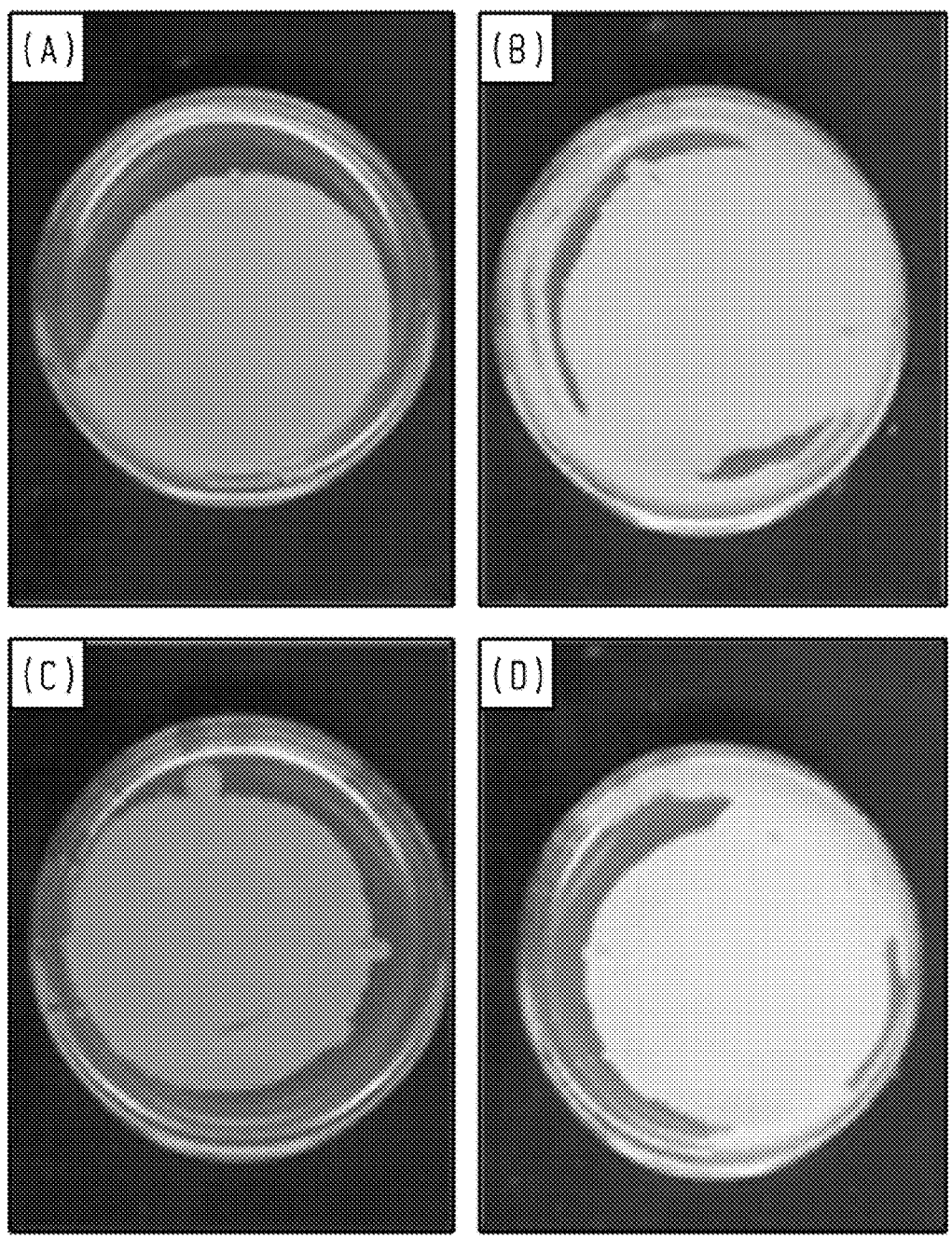
FIG. 6 shows photographs of microbial growth on untreated EHOM or EHOM treated with an example barrier-forming composition, followed by infection with *C. albicans*, as described in Examples 33-40.
Figure 7:
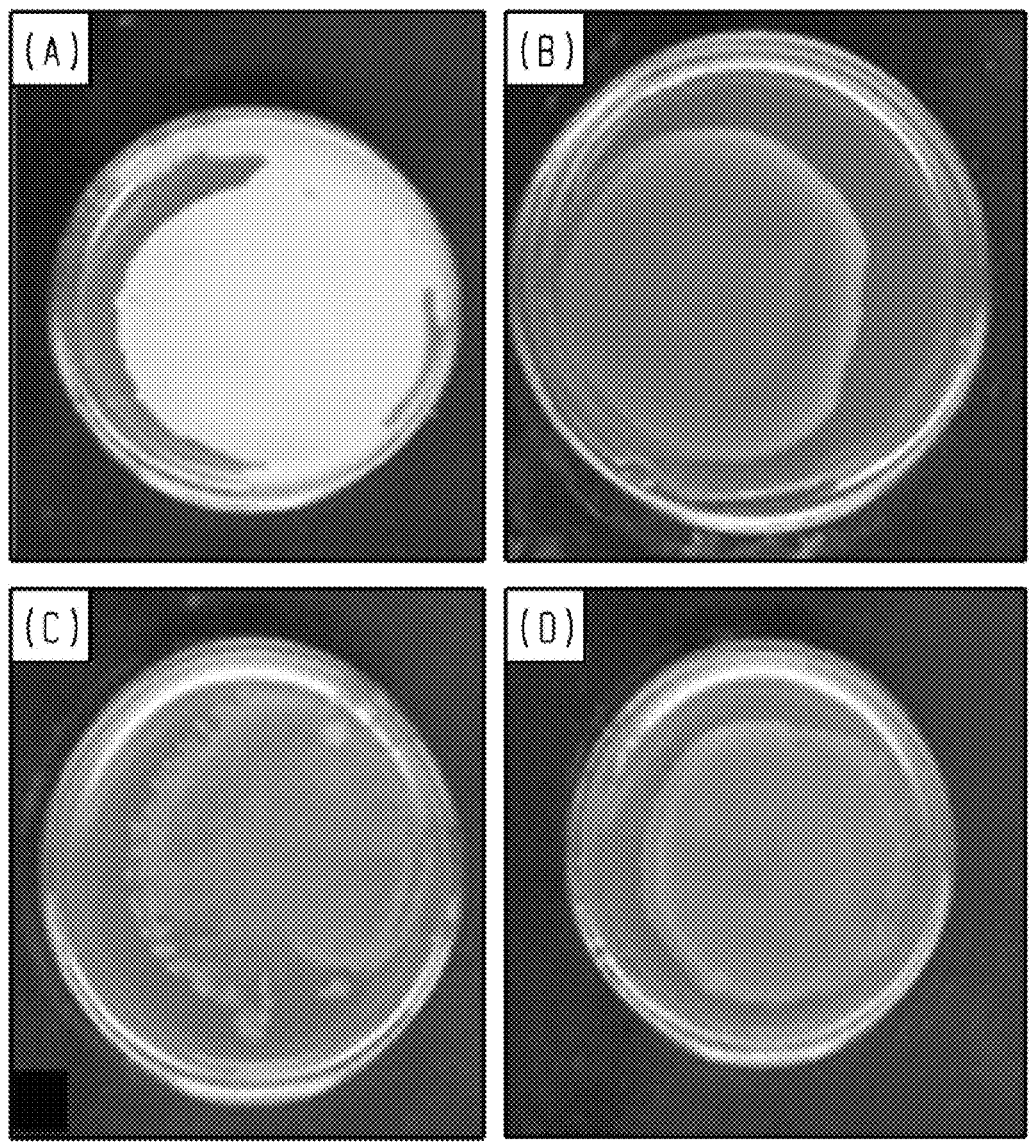
FIG. 7 shows photographs of microbial growth on untreated EHOM or EHOM treated with formulations followed by infection with *S. mutans*, as described in Examples 33-40.
Figure 8:
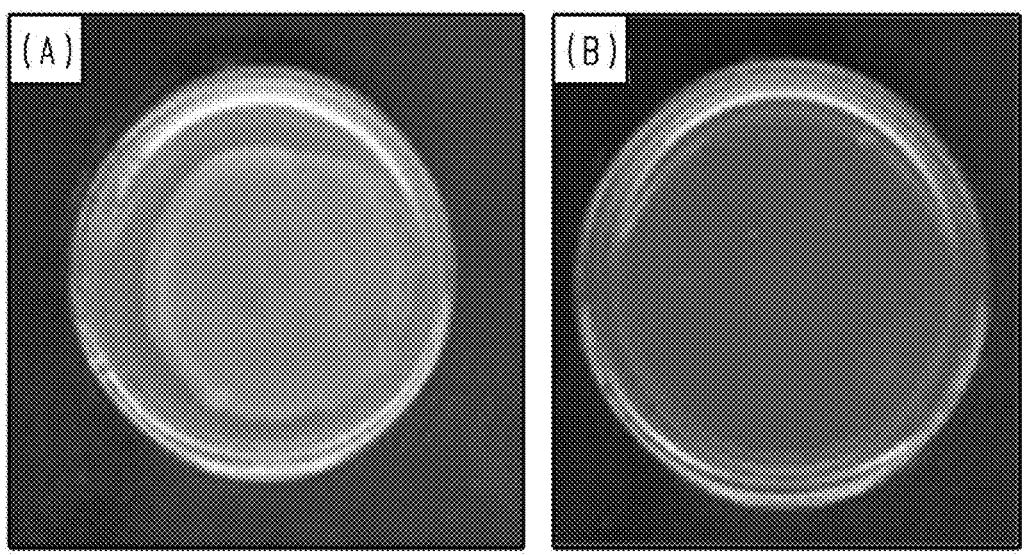
FIG. 8 shows photographs of microbial growth from "flow-through" media (collected from the lower chamber) of EHOM treated with an example barrier-forming composition, as described in Example 33-40.

FIGS. 6 and 7 show that both Candida and Streptococcus were able to grow on the surface of EHOM treated with the compositions of Examples 5-6. In contrast, as shown in FIG. 8, no microbial growth was observed when the "flow-through" medium collected from the lower chambers of EHOMs of Examples 36 or 40, i.e. those treated with the Example 7 composition. This indicates that treatment of the EHOMs with the Example 7 composition did not cause damage to the surface of the mucosal tissues and organisms were unable to penetrate the treated EHOM. Similar results were obtained with EHOM treated with the compositions of Examples 5 and 6 (data not shown). These data indicate that the combination of glycerine and xanthan gum is capable of forming a protective barrier on mucosal tissues.

Examples 41-47

Tested Formulations are not Toxic and do not Cause Damage to the Cells/Tissues

In Examples 41-47, the EHOM model was used to assess the toxicity of the composition. Examples 41-47 were formulated as stated in Table IV.

TABLE IV

|  | Barrier-forming composition Pre-Treatment | Microbe Overlay | Figure Reference |
|---|---|---|---|
| Example 41 | None | C. albicans | FIG. 9(A) |
| Example 42 | Example 5 | C. albicans | FIG. 9(A) |
| Example 43 | Example 6 | C. albicans | FIG. 9(A) |
| Example 44 | Example 7 | C. albicans | FIG. 9(A) |
| Example 41A | None | S. mutans | FIG. 9(B) |
| Example 45 | Example 5 | S. mutans | FIG. 9(B) |
| Example 46 | Example 6 | S. mutans | FIG. 9(B) |
| Example 47 | Example 7 | S. mutans | FIG. 9(B) |

After pre-treatment and incubation according to the procedures of Examples 27 and 28, culture supernatant was collected from the Example 41-48 EHOM tissues and used to measure LDH activity.

Figure 9:
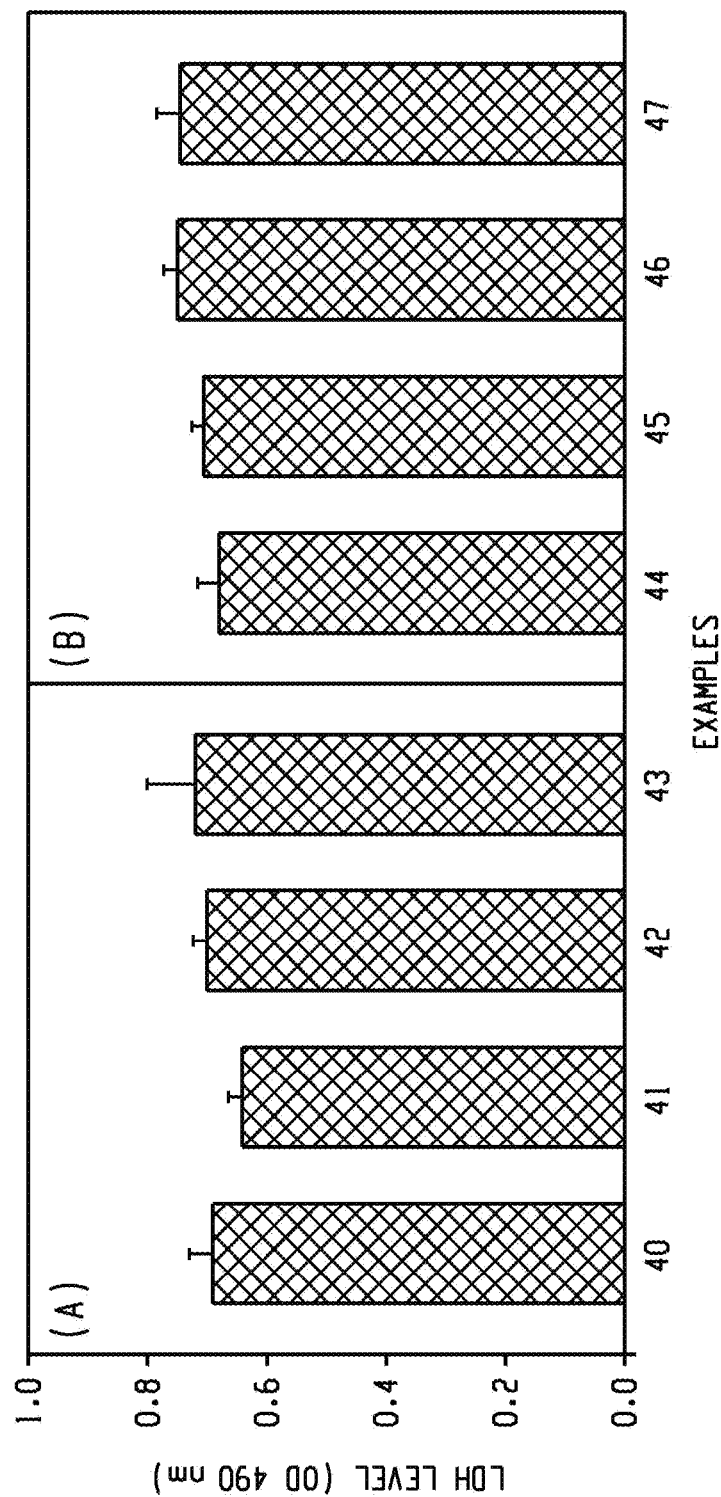
FIG. 9 presents graphs showing LDH release by EHOM treated with saline (control) or example barrier-forming compositions, followed by infection with (A) *C. albicans* or (B) *S. mutans*, as described in Examples 40-47.

As shown in FIG. 9, no significant increase in LDH levels was observed in Examples 41-48 irrespective of whether the formulations contained cetylpyridinium chloride with or without preservatives and infected with either *Candida albicans* or *S. mutans*, respectively. These data confirmed the non-toxic effect of the Example barrier-forming compositions and that these formulations maintained the integrity of the host mucosal tissues.

Data are mean±SD. No significant difference between untreated and treated tissues was noted.

Taken together, the data indicates that the example compositions represent an effective and a safe barrier that can prevent microorganisms from penetrating and invading human mucosal tissues.

Examples 48-61

Preclinical evaluation of the barrier-forming composition showed that the composition was effective against many bacteria and yeasts. The antimicrobial activities of the Example 7 barrier-forming composition were evaluated against a number of clinical isolates obtained from patients, including *S. salivarius, P. gingivalis, S. pyogenes, S. pneumonia, Fusobacterium nucleatum, S. mutans, S. aureus, Y. enterocolitica, S. oxalis, S. mitis, C. albicans, C. krusei, C. tropicalis*, and *C. glabrata*. Activity of the Example 7 barrier-forming composition was evaluated by determining its minimum inhibitory concentration (MIC) using reference methods described in the Clinical and Laboratory Standards Institute (CLSI) documents M07-A8, M11-A7, and M27-A3.

A standardized inoculum of several types of aerobic or anaerobic bacteria ($1 \times 10^4$ cells/ml) was incubated with serially diluted solutions of Example 7 (containing 0.1% CPC, or 1 µg/ml) or 2% chlorhexidine gluconate (CHX, 20 µg/mL) as a comparative example. Cells were allowed to grow in the presence or absence (growth control) of the test agents for 24 hours. The MIC for each agent was defined as the concentration that induced a 100% growth inhibition (compared to no-drug control).

A similar microdilution-based CLSI method (M27-A2) was used to evaluate the activity of Example 7 against albicans and non-albicans *Candida* species.

TABLE V

|  | Organism | Example 7 MIC (µg/mL CPC) | Chlorhexidine MIC (µg/mL chlorhexidine) |
|---|---|---|---|
| Example 48 | S. salivarius | 0.98 | 19.6 |
| Example 49 | P. gingivalis | 0.98 | 19.6 |
| Example 50 | S. pyogenes | 0.98 | 19.6 |
| Example 51 | S. pneumonia | 0.98 | 19.6 |
| Example 52 | F. nucleatum | 1.95 | 19.6 |
| Example 53 | S. mutans | 1.95 | 19.6 |
| Example 54 | S. aureus | 3.91 | 19.6 |
| Example 55 | Y. enterocolitica | 3.91 | 19.6 |
| Example 56 | S. oralis | 500 | 19.6 |
| Example 57 | S. mitis | 500 | 19.6 |
| Example 58 | C. albicans | 0.25 | 19.6 |
| Example 59 | C. krusei | 0.06 | 19.6 |
| Example 60 | C. tropicalis | 0.06 | 19.6 |
| Example 61 | C. glabrata | 0.125 | 19.6 |

The barrier-forming composition was also found to have potent antimicrobial activity against: MRSA, *Acinetobacter baumannii, Streptococcus sanguis, S. gordonii*, and *Aggregatibacter actinomycetemcomitans*.

As can be seen in Table V, the Example 7 composition exhibited potent activity against many aerobic and anaerobic bacteria, as well as the fungi.

The MIC of the Example 7 barrier-forming composition against *S. oralis* and *S. mitis* was noticeably elevated (500 µg/mL) compared to other organisms. It is interesting to note that *S. oralis* and *S. mitis* are normal commensals of the oral cavity. Activity of the commonly used antimicrobial chlorhexidine (2% solution) was also determined by the same method. Table V shows the MIC of the Example 7 barrier-forming composition and chlorhexidine (2% solution) as a comparative example against various microorganisms.

Taken together, these results demonstrate that Example 7 possesses potent activity against pathogenic bacteria and fungi commonly isolated from the oral cavity. This activity was more potent than that observed for chlorhexidine.

A similar activity profile was observed for the barrier-forming compositions of Examples 10 and 11.

Example 62

As a further comparison, published data shows that the tested barrier-forming composition has a better or at least equivalent MIC compared to CPC alone (i.e. not in a composition according to the barrier formulation disclosed herein). See Frank-Albert Pitten and Axel Kramer, "Efficacy of Cetylpyridinium Chloride Used as Oropharyngeal Antiseptic," Arzneim.-Forsch./Drug Res. 51 (II), pp 588-595 (2001), which is incorporated herein by reference. The data varies based on the microorganism tested, but, for example, CPC (alone) against *S. mutans* has an MIC of 5.0-6.25 µg/mL, which is much less effective than the 1.95 µg/mL reported in Example 53. This was an unexpected result since CPC has the risk of losing its activity when mixed with other excipient chemicals in a formulation. See Department of Health and Human Services (Food and Drug Administration) (1994) Oral Health Care Drug Products for Over-the-Counter Human Use; Tentative Final Monograph for Oral Antiseptic Drug Products. Proposed Rules (21 CFR Part 356. Federal Register 59:6084-124.

Examples 63-69

Duration of Antimicrobial Activity of Barrier-Forming Compositions In Vitro: Determination of Post-Antimicrobial Effect (PAE)

The PAE of Example 8 against several microorganisms was evaluated in Examples 63-68. Control Example 69 was also provided. Several microorganisms were exposed to Example 8 (at a concentration equal to the MIC) for 1 min followed by three washes to remove residual formulation. The treated cells were then spread on agar medium plates, which were incubated at 37° C., and the time taken for the cells to regrow was determined. PAE was expressed as the time (in hours) for which growth inhibition (%) was maintained by the Examples 63-68, compared to the untreated control Example 69.

Figure 10:
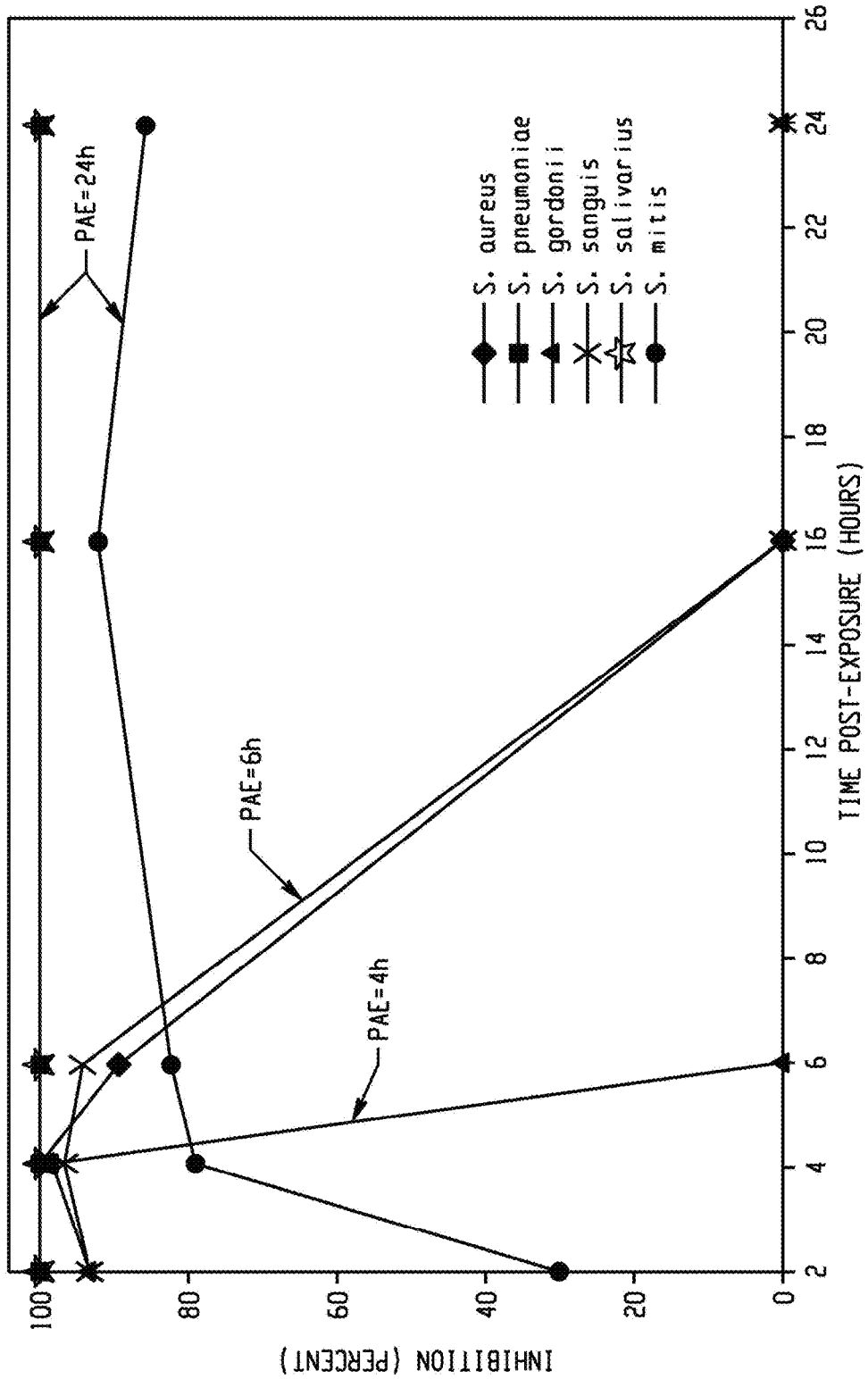
FIG. 10 is a graph showing post-antimicrobial effect of barrier-forming compositions against bacteria, as described in Examples 63-69.

As shown in FIG. 10, Example 8 exhibited a PAE ranging between 4 hours to 24 hours, depending on the organism tested (S. aureus, S. pneumonia, S. gordonii, S. sanguis, S. salivarius, and S. mitis). Similar activity of Example 8 was observed against Candida (data not shown). Other Example barrier-forming compositions exhibited similar PAE against microorganisms.

Example 70

Testing of PAE for the Example 7 barrier-forming composition against S. mutans compared to a similar comparative Example with lower CPC content of 0.7% showed that the PAE of Example 7 was 24 hours, while that of Comparative Example 70 was 6 hours. Thus demonstrating that Example 7 exhibits greater prolonged antimicrobial activity than comparative Example 70, and that additional amounts of CPC have more than a simple additive effect on antimicrobial activity.

Examples 71-76

Scanning electron microscopy was also used to show that treatment of S. sanguis, (Example 71), S. oxalis, (Example 72), and C. albicans (Example 73) with the composition of Example 3 resulted in destruction of cellular integrity.

In Examples 71-73, cells were grown in the presence of Example 3 for 24 hours. Next, the cells were washed to remove residual formulation, dehydrated by passing through a series of alcohol solutions (10% to 100%, v/v) and processed for SEM analysis. Control Examples 74-76 differed from Examples 71-73 in that they were not grown in the presence of Example 3.

Figure 11:
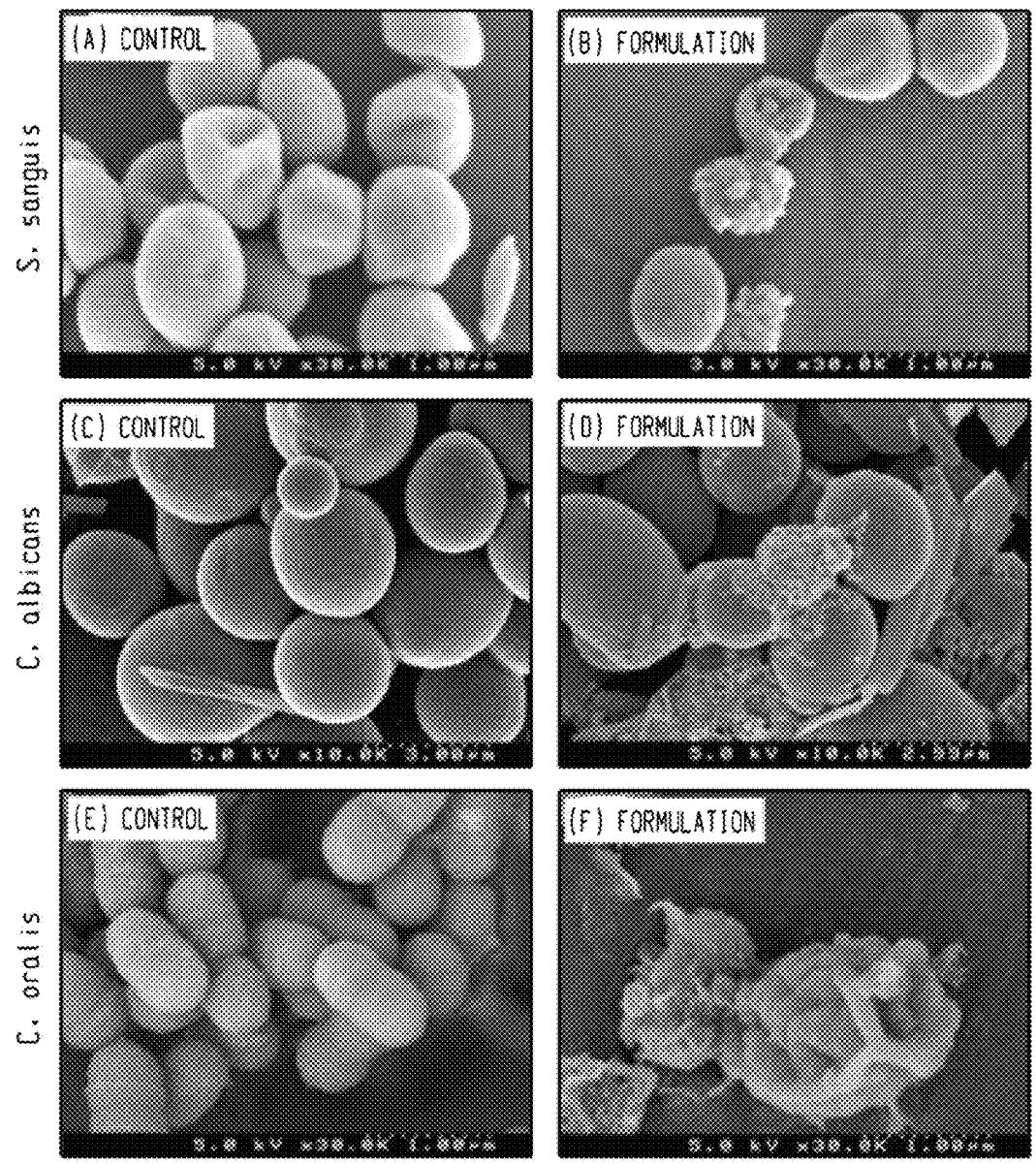
FIG. 11 shows scanning electron micrographs of *S. sanguis*, *C. albicans*, and *S. mutans*, untreated or treated with barrier-forming composition, as described in Examples 71-76.

The SEM photos showed that unlike untreated control Examples 74-76, which demonstrated healthy intact cells (FIG. 11 A, C, E), microbes exposed to the Example 3 barrier-forming composition were deformed, collapsed, and exhibited total destruction of cellular integrity with clear evidence of leakage of cytoplasmic material. (FIG. 11, B, D, F).

Examples 77-79

Since biofilms are precursors to certain infectious diseases, in Examples 77-79, experiments were performed to determine whether the barrier-forming compositions can prevent formation of biofilms by bacteria and yeasts. Biofilms were formed using an in vitro model. See Chandra et al. "In vitro Growth and Analysis of Candida Biofilms" Nature Protocols 3(12): 1909-1924 (2008).

In Examples 77-79 a standard biofilm model was employed to determine whether the Example 3 barrier-forming composition exhibits activity against bacterial and fungal biofilms. In Examples 77-79, three different microorganisms (C. albicans, S. oralis, and S. salivarius) were adhered on substrate for 90 minutes to allow biofilms to form to adhesion phase. Next, discs containing the adherent bacteria were incubated for 15, 30 or 60 minutes with 50% concentration of Example 3 (1:1 dilution with appropriate medium). Following incubation, biofilms were scraped, spread on culture media, incubated and colony forming units (CFUs) were determined. Media diluted with phosphate buffered saline (PBS, 1:1) were used as a control. Table VI reports data at 0 (Control), 15, 30, and 60 minutes.

TABLE VI

Effect of Barrier-forming composition on Early Phase Biofilms (log CFU)

| Exposure time | Example 77 C. albicans | Example 78 S. oralis | Example 79 S. salivarius |
| --- | --- | --- | --- |
| Control | 5.44 | 3.25 | 3.16 |
| 15 min | 0 | 0 | 0 |
| 30 min | 0 | 0 | 0 |
| 60 min | 0 | 0 | 0 |

Figure 12:
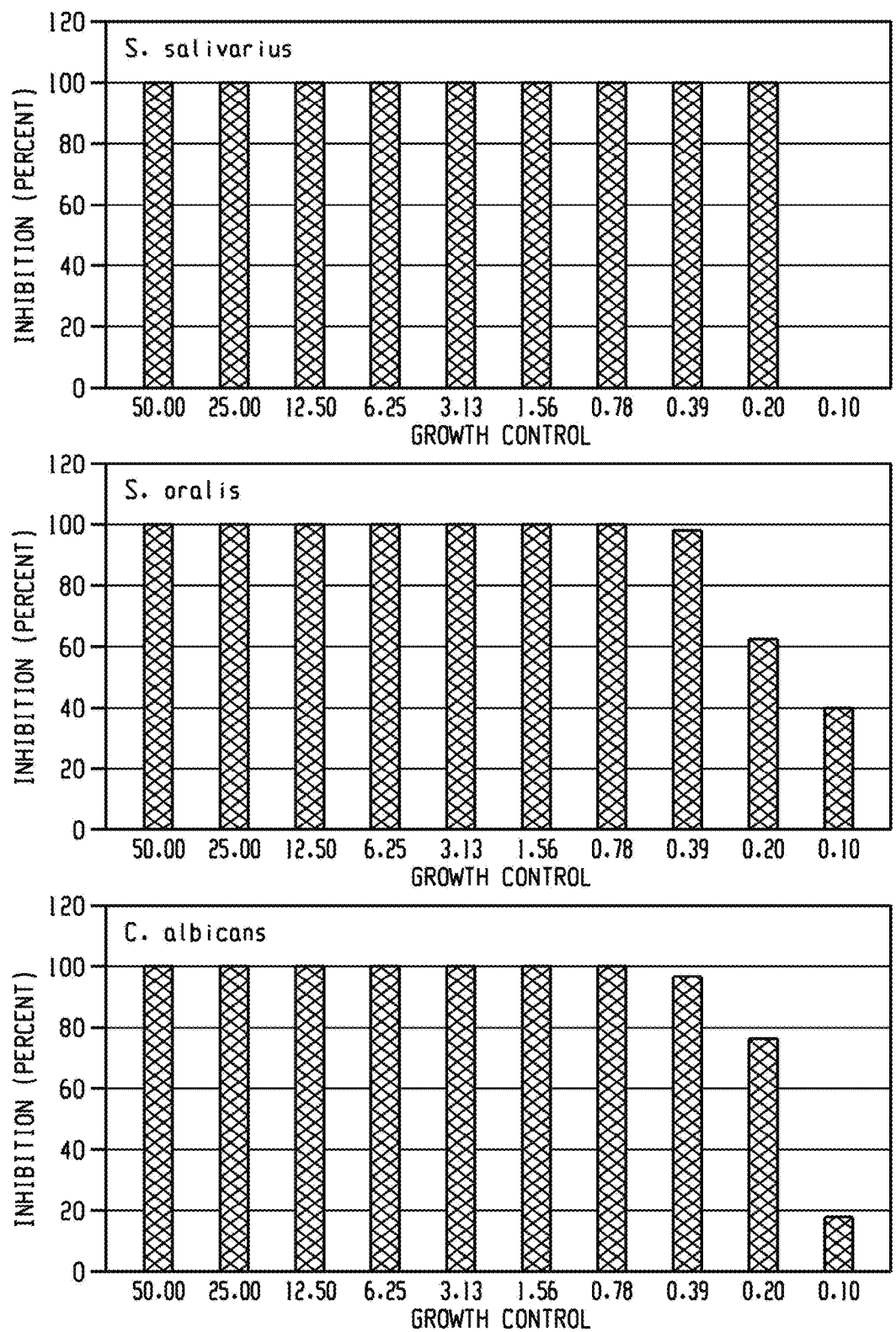
FIG. 12 presents graphs depicting activity of an example barrier-forming composition against biofilms formed by bacteria and fungi, as described in Examples 77-79.

FIG. 12 also reports data on Examples 77-79 as a graph of % inhibition versus growth control. These results showed that Example 3 barrier-forming composition inhibited bacterial and fungal microbes with an MIC of 0.2% against biofilms formed by S. salivarius, S. oralis, or C. albicans.

Examples 80 and 81

Figure 13:
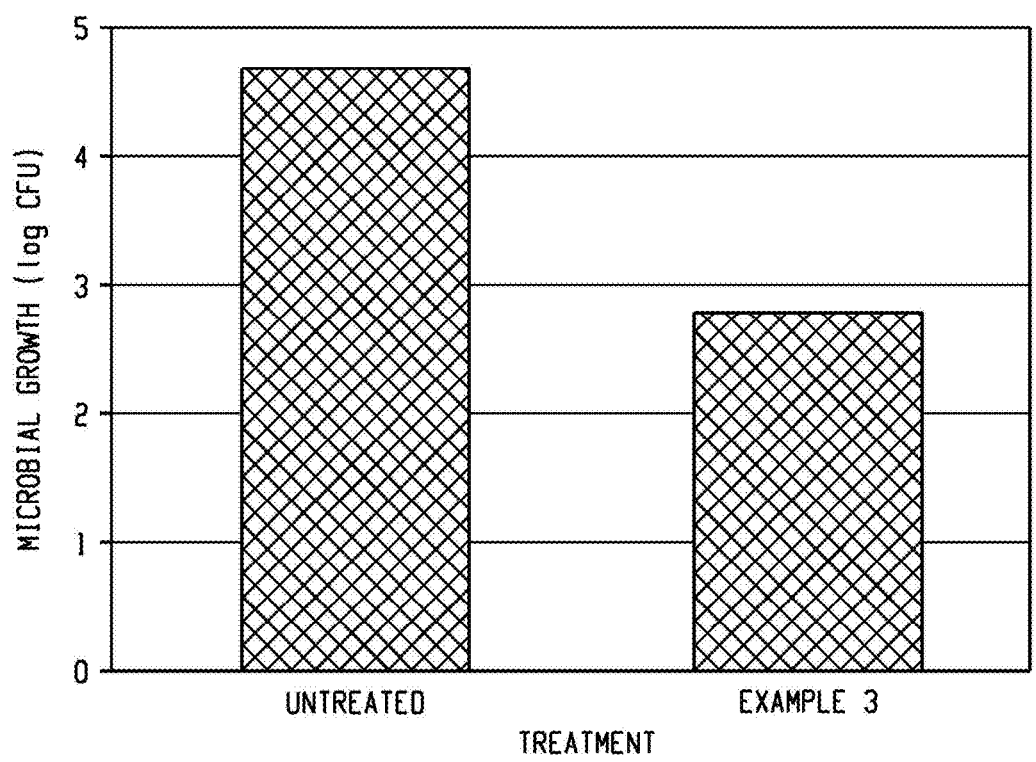
FIG. 13 is a graph showing activity of an example barrier-forming composition on microbial biofilms after a 1-min exposure, as described in Examples 80-81.

In Example 80 we evaluated the effect of 1 minute exposure of C. albicans early phase biofilms to Example 3, and found that even with an exposure for as short a time as 1 minute, it was able to inhibit biofilm formation (FIG. 13). Example 81 was an untreated control sample.

Examples 82-84

Ability of Barrier-Forming Composition to Treat Mature Biofilms

To determine whether the barrier-forming composition can treat biofilms, we evaluated its activity against fully formed mature biofilms. Biofilms were grown to mature phase, and then exposed to Example 7 for 2 or 4 hours, and the resulting CFUs were determined. A composition that causes at least 2-log reduction in microbial CFUs compared to untreated cells is considered to be effective against microbial biofilms.

As shown in Table VII, exposure to Example 7 resulted in complete eradication of biofilms formed by C. albicans and S. oxalis, and a 3.4-log reduction in CFUs for biofilms formed by S. salivarius compared to the untreated control (log CFU=3.95 vs. 7.36, respectively).

TABLE VII

Effect of Example 7 on mature biofilms (log CFU)

| Exposure time | Example 82 C. albicans | Example 83 S. oxalis | Example 84 S. salivarius |
|---|---|---|---|
| Control | 5.60 | 7.40 | 7.36 |
| 2 h | 0 | 0 | 4.00 |
| 4 h | 0 | 0 | 3.95 |

In summary, the results indicate that Example 7 possesses potent activity against biofilms formed by bacteria and fungi.

Examples 85-86

The Barrier-Forming Composition is Also Active Against Viruses

The activity of barrier-forming composition against viruses, including respiratory viruses (influenza virus H1N1, strain 2009/H1N1/infA) and the human immunodeficiency virus (HIV) was determined.

The Barrier-Forming Composition Inhibits the Infectivity of Influenza A

To evaluate the effect of the barrier-forming composition on the infectivity of influenza virus, Madin Darby canine kidney (MDCK) cells were grown to ≥90% confluence at 37° C. prior to infection. MDCK cells are used routinely for assays involving influenza viruses.

In Example 85 cell monolayers were exposed to the Example 7 barrier-forming composition. In control Example 86 the cell layers were exposed to optiMEM (+P/S,+Lglu) tissue culture media for different times: (1) T1: 30 min exposure, (2) T2: 1 h exposure, (3) T3: 2 h exposure. Next, the formulation was removed and the cell monolayers were infected with influenza virus (multiplicity of infection (MOI)=0.1). Cells that were untreated or infected immediately after exposure (T0) were used as baseline controls. Infected cells were then centrifuged, resuspended in 500 µL of growth medium, and incubated at 32.5° C. for 48 hours. Immunofluorescence microscopy (using FITC labeled anti-influenza antibody) was also used to evaluate the effect of the Example 7 barrier-forming composition on the ability of influenza virus to infect mammalian cells.

Figure 14:
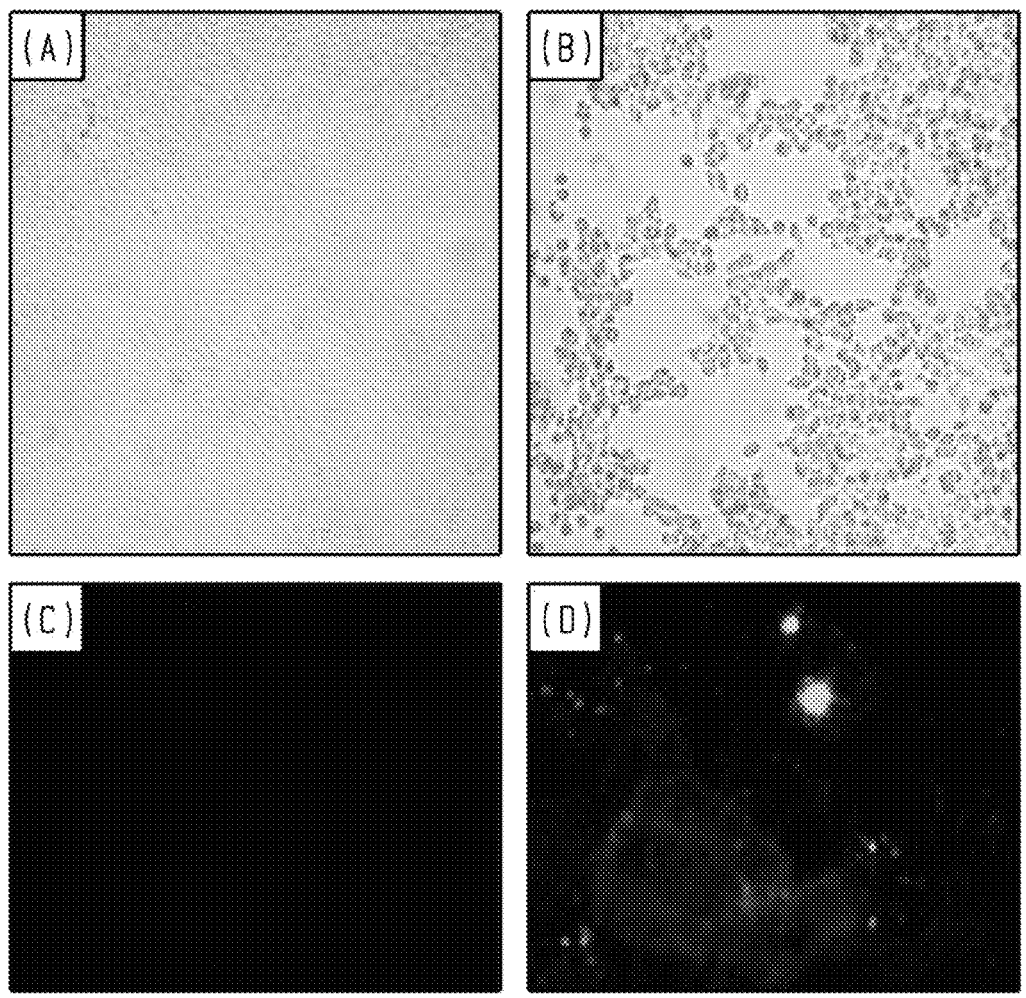
FIG. 14 presents fluorescent microscopy photographs showing the effect of an example barrier-forming composition on cytopathic effects (CPE) of influenza (H1N1)-infected MDCK cells, as described in Examples 85-86.

FIG. 14 shows the effect of Example 7 on cytopathic effects of influenza-infected MDCK cells (Example 85) (panels A and C), and control Example 86 (panels B and D). Images were obtained from: phase contrast (A-B), and immunofluorescence microscopy (C-D). No identifying cytopathic effect (CPE) was observed in formulation-treated cells. Untreated cells displayed typical CPE including focal rounding and degenerative changes.

The data showed that exposure of cell monolayers to Example 7 for 30 minutes, 1 hour, or 2 hours remained confluent and healthy (Example 85). In contrast, in the untreated cells and cells treated immediately prior to infection (T0) (control Example 86) demonstrated substantial cytopathic effect. As seen in FIG. 14 panel C, no fluorescence was observed in the barrier-forming composition treated cells of Example 85, while the untreated cells of Example 86 exhibited fluorescence (FIG. 14 panel D).

Figure 15:
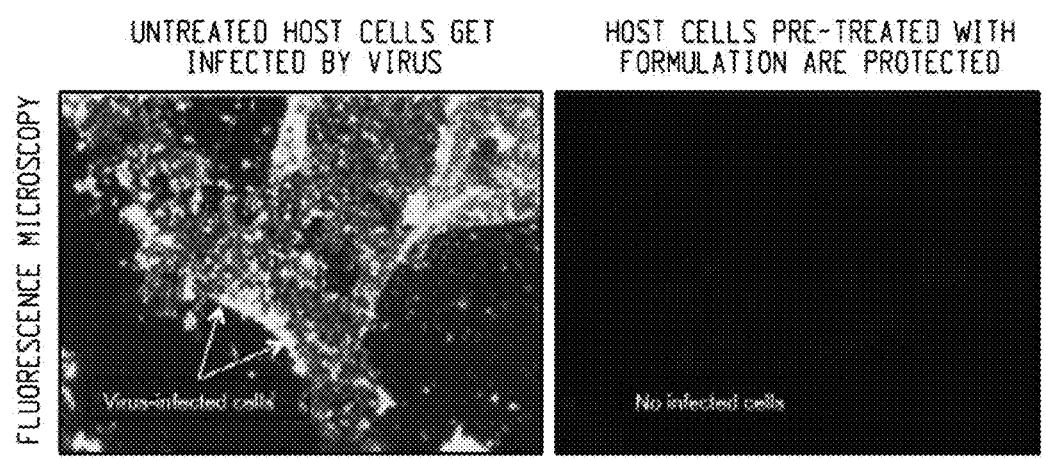
FIG. 15 presents fluorescent microscopy photographs showing the effect of an example barrier-forming composition on against H1N1 virus, as described in Examples 85-86.

Further fluorescence microscopy images corresponding to Examples 85 and 86 are presented in FIG. 15.

Examples 87 and 88

Activity of Barrier-Forming Composition on Viral Load Using Quantitative PCR

Figure 16:
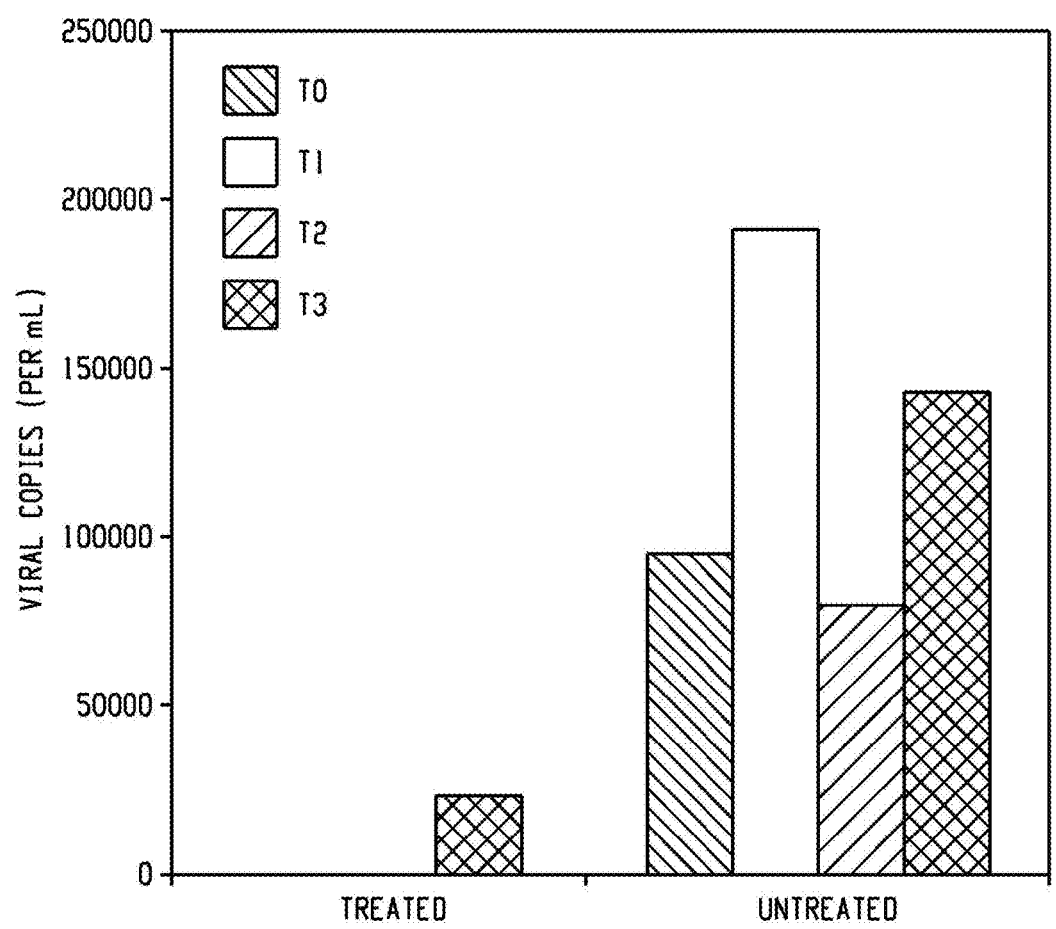
FIG. 16 is a graph showing levels of influenza virus in infected barrier-forming composition treated and -untreated cells, as determined by quantitative PCR, as described in Examples 87-88.

FIG. 16 shows levels of influenza virus in infected treated cells (Example 87) and untreated cells (Example 88), as determined by quantitative PCR. In Example 87, cells were treated with Example 7 and in control Example 88 the cells were left untreated. Later the supernatants were collected and analyzed for the presence of virus.

Cell culture supernatants from the same assay as in Examples 87 and 88 were collected and nucleic acid extracted using QIAamp Viral RNA Kit (QIAGEN, Valencia, Calif.). Random hexamer primers (Invitrogen Carlsbad, Calif.) were used to create a cDNA library for each specimen. Reverse transcription reactions were performed with M-MLV RT (Invitrogen, Carlsbad, Calif.) according to the manufacturer's specifications. Quantitative analysis was performed on a StepOne Plus Taqman Real Time PCR (Applied Biosystems, Branchburg, N.J.) using TaqMan Universal PCR Master Mix (Applied Biosystems, Branchburg, N.J.), 2 µl of cDNA sample, and primers/probes targeting the influenza matrix gene. A reference standard was prepared using a cDNA fragment of the H1N1 matrix gene and human RNAse P amplified by conventional RT-PCR, gel purified (QIAquick, Qiagen, Valencia, Calif.), and quantified using a spectrophotometer (Beckman Coulter, Brea, Calif.).

As shown in FIG. 16 and Table IV, the Example 87 cells treated Example 7 for 30 min or 60 min did not have detectable influenza at 48 hours post infection. Moreover, treatment with Example 7 for 2 hours resulted in a 6-fold decrease in viral load, compared to the untreated control or those treated immediately prior to infection (Example 88).

TABLE VIII

| | Example 87 | Example 88 (control) |
|---|---|---|
| 30 min | 0 | 192000 |
| 60 min | 0 | 79800 |
| 120 min | 23400 | 143000 |

Examples 89-91

Barrier-Forming Composition has Direct Antiviral Effect Against Influenza Virus To determine whether the barrier-forming composition has direct antiviral activity against influenza virus, we infected African Green Monkey Kidney (CV-1) cells (grown in 24-well plates to 90% confluence) with influenza virus that was pre-treated with Example 7. CV-1 cells are routinely used a highly susceptible substrate for diagnosis and study of viruses.

In Examples 89-91, a standardized amount of influenza (0.1 MOI) was pretreated for 5 minutes at room temperature with: (1) Example 7 (to form Example 89), (2) control Example 6, a compound without CPC but with preservatives (to form Example 90), and (3) control Example 5 placebo alone (a compound without CPC and preservatives) (to form Example 91). After the 5 minute incubation virus/drug mix was diluted by an additional equal volume with optiMEM (+P/S,+Lglu) to dilute out the treatment compositions.

In Examples 89-91, CV-1 cells were prepared as described in above. The Example 89-91 treated and untreated viruses were then inoculated onto the cells as described above.

Figure 17:
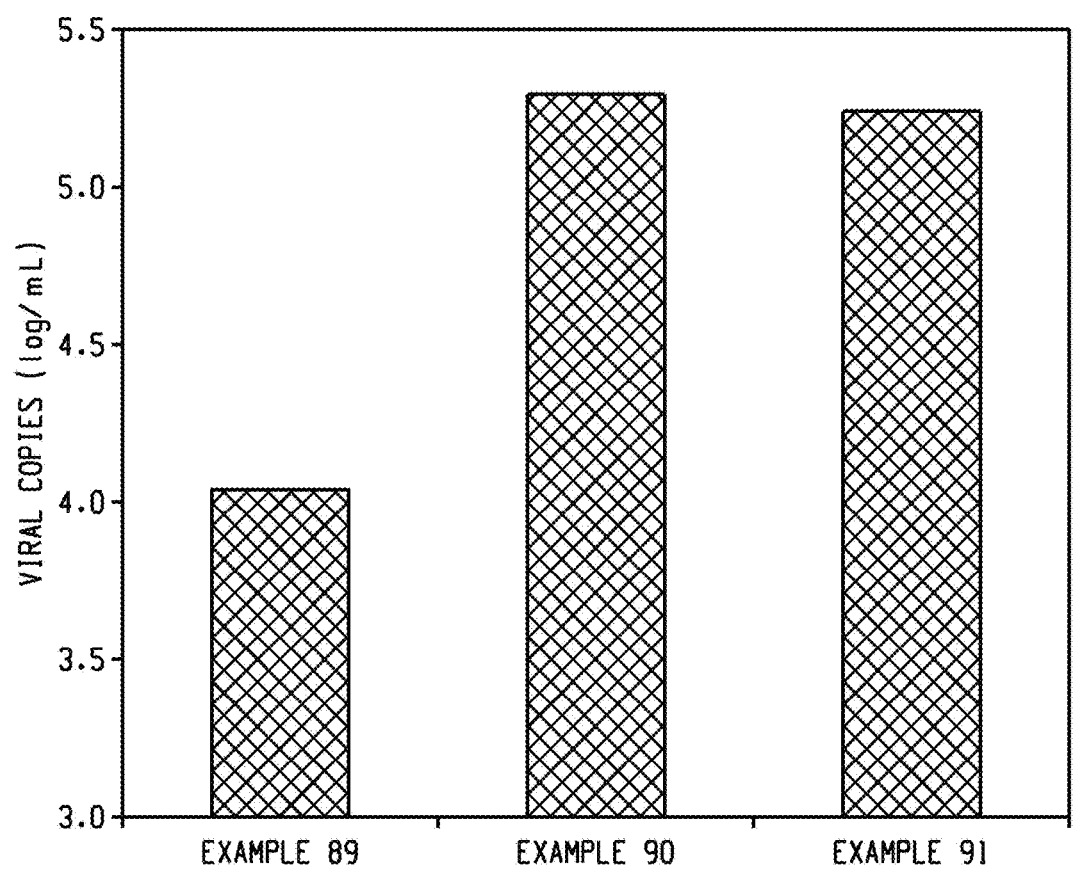
FIG. 17 is a graph showing direct antiviral activity of example barrier-forming compositions prepared with or without preservatives and antimicrobial agent (CPC) against influenza virus, determined using quantitative PCR, as described in Examples 89-91.

Influenza viral load was determined by real time PCR as described above. The data as shown in FIG. 17 showed significant decrease in viral load for influenza virus pretreated with the Example 7 barrier-forming composition containing the antimicrobial agent CPC (Example 89), compared to those containing only the barrier-forming composition and/or preservative but no CPC (Examples 90 and 91). Pre-treatment of virus with Example 7 exhibited significant decrease in viral copies, compared to formulations with no CPC.

These results demonstrate that the Example 7 barrier-forming composition possesses direct antiviral activity against influenza virus that is not inherent in Examples 5 and 6.

Examples 92 and 93

In Examples 92 and 93, the barrier-forming composition's ability to inhibit the infectivity of influenza A (2009/H1N1/infA) was tested. African Green Monkey Kidney (CV-1) cells were grown in 24-well plates to 90% confluence. Next, the barrier-forming composition, Example 7, was applied to the cells (20% Example 7, 80% OptiMeM, working CPC concentration of 0.02%.) in Example 92. Each time point matched with control Example 93 (No barrier-forming composition applied, 100% OptiMeM). The barrier-forming composition was allowed to dwell on the surface for 30 minutes, and then removed from the ceil monolayer. Cells were thoroughly washed twice with sterile optiMEM (+PfS,+Lglu). Influenza was inoculated at MOi=0.1 at 30 minute intervals from TO through T+6 hours. Following infection, cells were then centrifuged @2200 rpm×30 minutes and 500 µl of optiMEM (+P/S, +Lglu, 2 µg/ml trypsin (sigma-Aldrich, St Louis, Mo.)) was applied. Infected cells were grown at 32.5° C. for 96 hours at 5% $CO_2$. The influenza viral load was determined by real time PCR.

Figure 18:
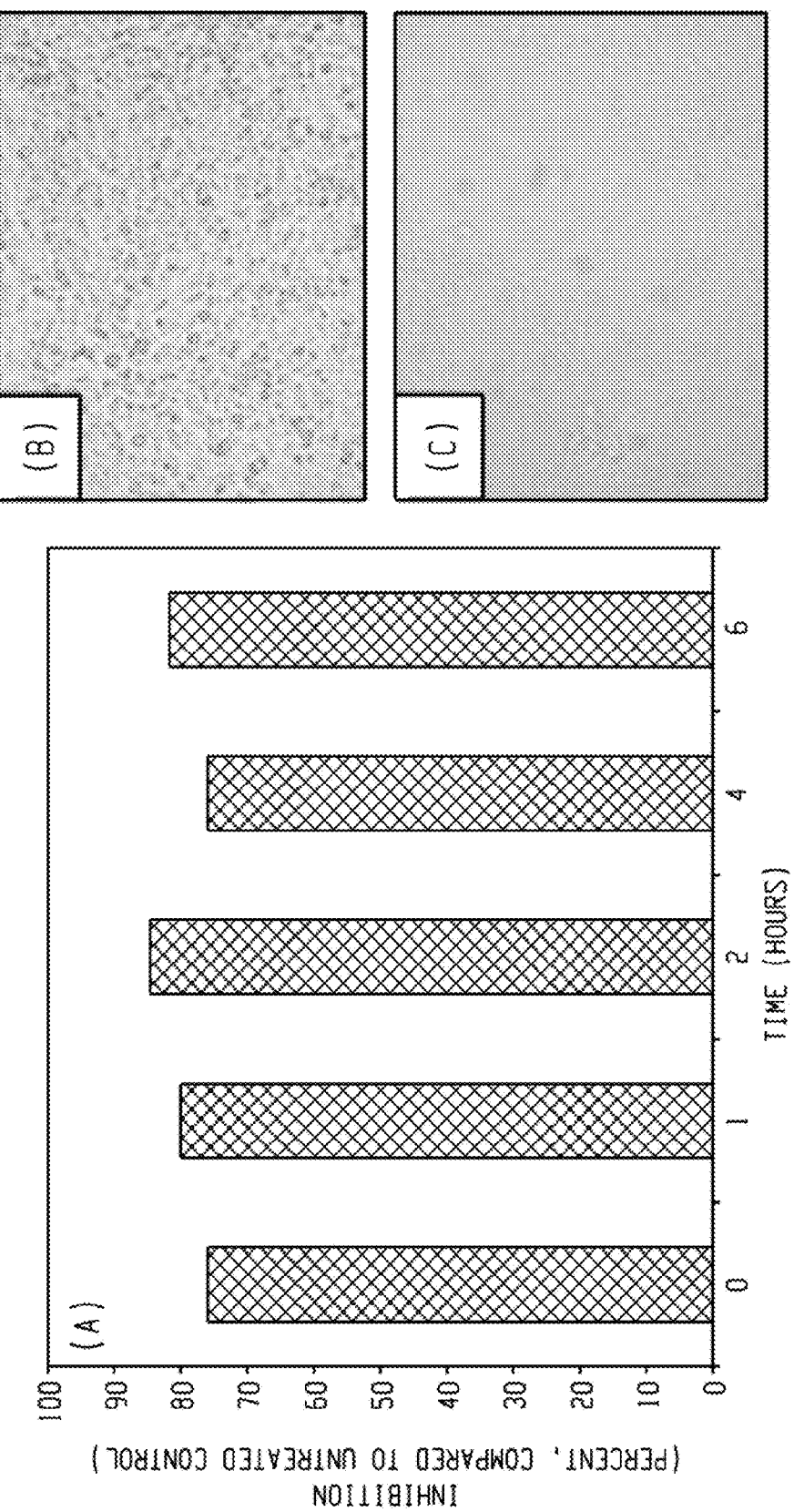
FIG. 18 shows the activity of an example barrier-forming composition against H1N1 virus over a 6 hour time period. Panel (A) is a graph showing a percent inhibition in viral growth compared to an untreated control. Panels (B) and (C) are micrographs of (B) untreated and (C) barrier-forming composition treated cells.

As shown in FIG. 18, pre-treatment of host monolayers with glycerine-xanthan gum formulation results in inhibition of viral infection by up to 84.93% compare to untreated controls. The fact that inhibition of viral infection was observed in host cells despite removal of the barrier-forming composition demonstrates that the barrier-forming composition formed a protective barrier on host cells, which prevented viral invasion for at least 6 hours.

FIG. 1 may be referred to as a possible mechanism accounting for the inhibition of infection.

Examples 94-96

Barrier-Forming Composition Exhibits Activity Against HIV

Figure 19:
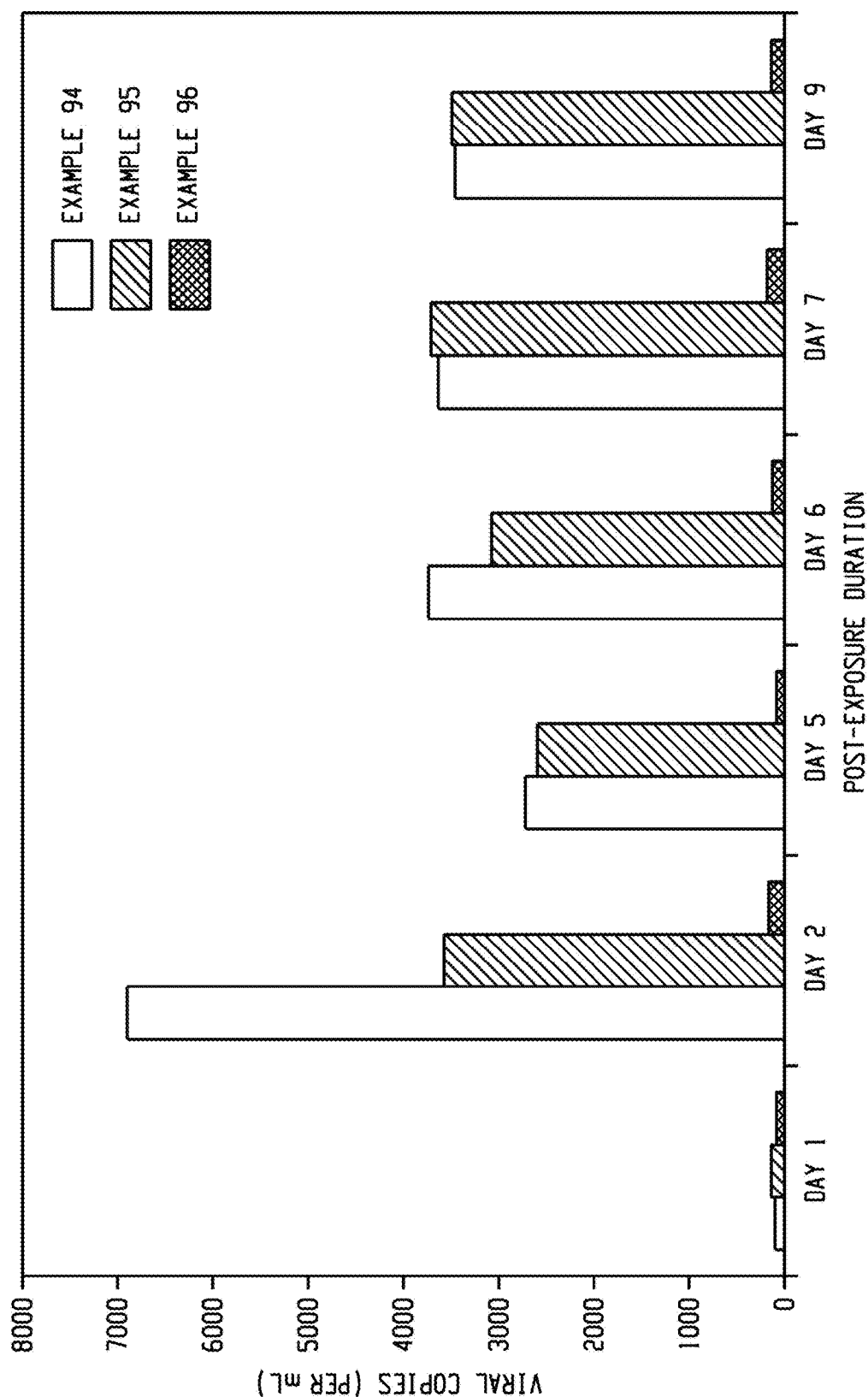
FIG. 19 is a graph showing the activity of formulations against HIV, as described in Examples 94-96.

Examples 94-96 determined whether the barrier-forming composition possessed activity against HIV. Host MT mammalian cells were plated into 96-well round bottom plates at a density of 15,000 cells/well in RPMI/10% FBS/PS. The next day (Day 2), virus was pretreated with control Example 5 (to form Example 94), control Example 6 (to form Example 95), or Example 7 (to form Example 96) for 5 minutes and added to cells. After 24 hours of exposure to formulation, the MT (macaque) mammalian cells were washed 3 times with phosphate buffered saline (PBS) and fresh media was replaced. Supernatant (10 µL) was collected post-treatment on Days 1, 2, 5, 6, 7, and 9, and the viral load was determined by reverse transcriptase (RT) activity. FIG. 19 shows a graph of the viral copies per mL for each of Examples 72-74 over a 9 day span.

The results showed that Example 7 in Example 96 exhibited anti-HIV activity at all time points monitored post-treatment.

The control Example 5 or control Example 6 without CPC and/or preservative in Examples 94 and 95 exhibited only minimal anti-HIV activity.

In summary, our findings demonstrate that the barrier-forming composition Example 7 containing CPC exhibits long-lasting antiviral activity against HIV.

Example 97

Representative organisms viral lesions are important infections in different mucosal tissues. In Example 97 an experiment was performed to determine whether the barrier-forming composition exhibits activity against the common oral Epstein-Barr virus (EBV). Western blotting was used to evaluate the ability of the Example 8 barrier-forming composition to degrade lytic viral protein EAD (indicating inhibition of viral replication).

Figure 20:
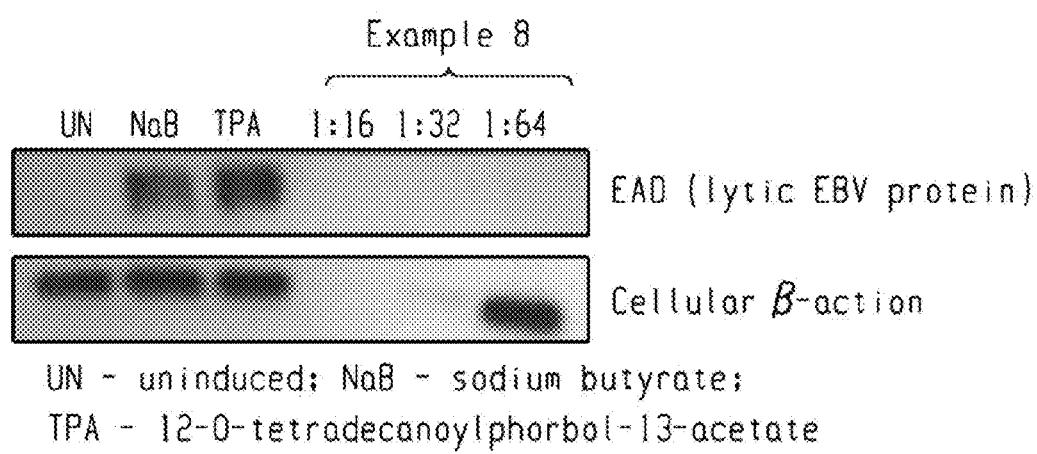
FIG. 20 is a Western blot showing activity of Example 8 against Epstein-Barr Virus (EBV), as described in Example 97.

In Examples 97, EBV-infected gastric epithelial cells were exposed to different dilutions (1:16, 1:32 and 1:64) of Example 8, and the presence of EAD protein was detected using specific antibodies. Presence of cellular β-actin was used as an indicator of epithelial cell integrity. As shown in FIG. 20, 1:64 dilution of Example 8 degraded EAD without affecting cellular actin. These results demonstrate that Example 8 specifically inhibits viral replication, and as such, is an effective anti-viral and useful for prevention of viral infection.

Examples 98-100

Duration of Anti-Microbial Barrier Versus Commercial Mouthwash Product

Figure 3:
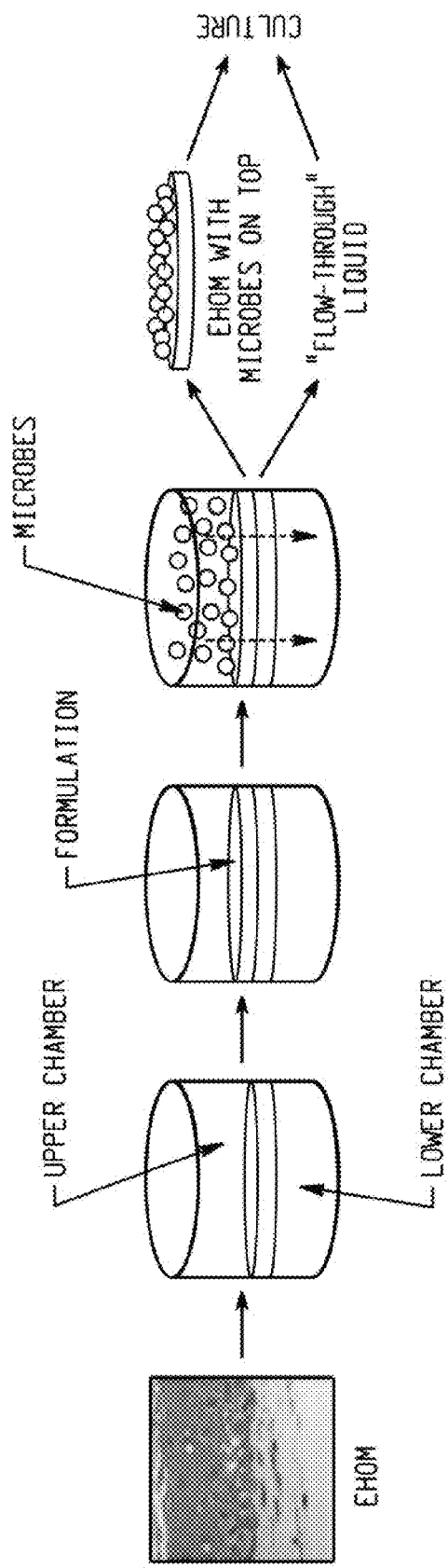
FIG. 3 is a schema showing the method of evaluation of microbial growth in the upper and lower chambers of an EHOM assay, as described in Examples 27-28.

To determine the duration for which the barrier-forming composition can maintain the antimicrobial activity, bacteria and fungi were exposed to an EHOM of Example 2 that was treated with the barrier-forming composition of Example 7 in a well and an EHOM of Example 2 that was treated with a comparative commercial product in a well for 2 minutes. The bacterial and fungal microbes were overlaid on top of the control untreated EHOM (Example 98) and the treated EHOMs (Example 99 and Comparative Example 100). Next the residual (flow-through) solution was removed from the bottom well (lower chamber of the EHOM model) and spread onto agar medium plates. FIG. 3 depicts this test method for further clarity. These plates were then incubated at 37° C., and the number of microbial cells (colony forming units, CFUs) growing after 24 hours were counted.

In control Example 98 an untreated EHOM was tested. In Example 99 *S. mitis* bacteria was overlaid on the barrier-forming composition as described above. Example 100 is a comparative example showing the activity of commercially available LISTERINE (containing ethanol (26.9%), menthol, thymol, methyl salicylate, and eucalyptol) against *S. mitis* bacteria. Table IX shows the results.

TABLE IX

| | CFUs of *S. mitis* bacteria in flow through liquid from EHOM | | |
|---|---|---|---|
| Time post-exposure | Example 98 (control) | Example 99 | Example 100 (comparative) |
| 2 hours | 1150000 | 5820 | 780000 |
| 4 hours | 1400000 | 5500 | 800000 |
| 6 hours | 1600000 | 6000 | 840000 |

Examples 101-103

In Examples 101-103, the same procedure of Examples 98-100 was performed except *Candida albicans* fungus was tested on the barrier-forming composition as described above. Table X shows the results. Example 103 is comparative, showing the activity of commercially available LISTERINE.

TABLE X

| | CFUs of *Candida albicans* in flow through liquid from EHOM | | |
|---|---|---|---|
| Time post-exposure | Example 101 (control) | Example 102 | Example 103 (comparative) |
| 2 hours | 1150000 | 12000 | 124000 |
| 4 hours | 2900000 | 12000 | 252000 |
| 6 hours | 3900000 | 13000 | 350000 |

The data further showed that Example 7 barrier-forming composition maintained activity for up to and including 24 hours. Taken together, these results showed that unlike LISTERINE, the Example 7 barrier-forming composition continued to maintain an intact barrier on EHOM tissues for up to and including 24 hours.

Examples 104-153

Figure 27:
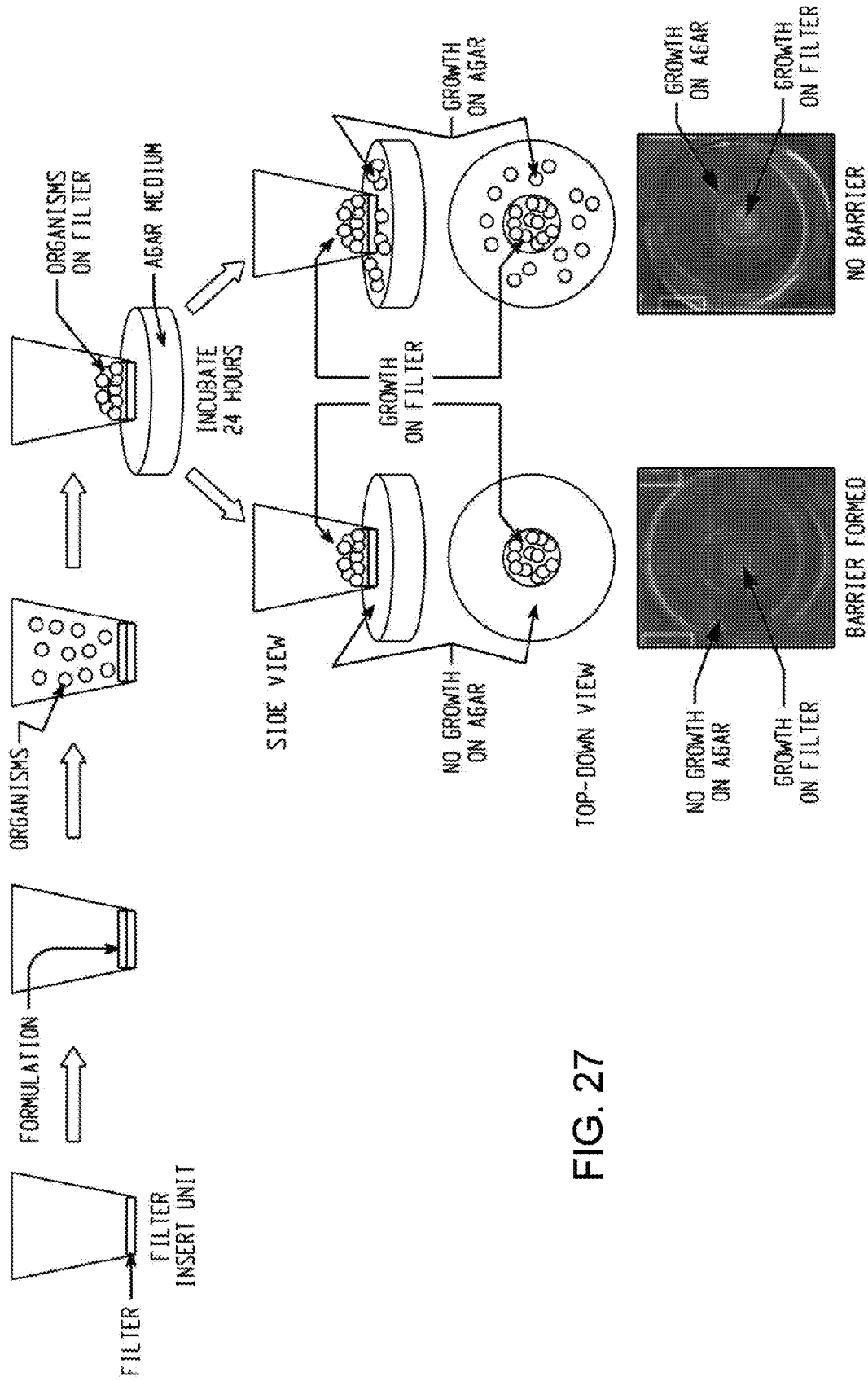
FIG. 27 shows is a schema describing the in vitro filter insert-based model to evaluate penetration of microbes across the barrier formed by example barrier-forming compositions, as described in Examples 199-205.

To identify further examples of concentrations of glycerin and xanthan gum that can form a barrier effective in preventing the passage of microorganisms, different concentrations of the gum xanthan gum and humectant glycerin were tested (5%-95% glycerin; 0.005%-0.5% xanthan gum) singly and in combination using an in vitro filter insert-based barrier model. FIG. 27 shows the general test method used for Examples 104-153.

Filter inserts of 3 μm and 8 μm diameter pore size were used for testing the passage of bacteria (*Streptococcus salivarius*) and fungi (*Candida albicans*), respectively. Glycerin or xanthan gum or their combinations (100 μL aliquots) were overlaid on the surface of the filter to form a barrier. The filter had a diameter of 24 mm. Thus, the film had a thickness of approximately 0.01 mm on the filter, mimicking a value in the range of thicknesses of the composition film when applied in a therapeutically effective amount to the mouth. Next, $5 \times 10^4$ cells of either bacteria or fungi were applied on top of the formed barrier in the filter inserts. Next, we placed these filter inserts on the surface of agar medium (Brain Heart Infusion (BHI) medium for bacteria, Sabouraud Dextrose (SD) medium for fungi) in 6-well plates. The plates along with the filter inserts were incubated overnight for 24 hours at 37° C.

The plates were monitored for the presence of bacterial or fungal growth CFUs (colony forming units) in the agar medium as well as in the filter insert. Microbial growth in the filter insert only, but not in the agar medium, demonstrated that an effective barrier was formed on the filter, which prevented passage of microorganisms. Conversely, growth in the agar medium around the filter insert suggested that the tested agents failed to form an effective barrier, allowing the organisms to go through the filter.

The results reported in Table XI showed that glycerin was able to form a barrier at concentrations greater than or equal to 55%, when tested alone. In contrast, xanthan gum alone did not form a barrier at any of the concentrations tested (ranging from 0.005% to 0.4%). However, it was observed that when combined with 0.01% xanthan gum, a barrier was formed at glycerin concentrations 7%, 45%, 55%, and 65%. Furthermore, combination of 0.4% xanthan gum with glycerin concentrations of 7%, 15%, 25%, 35%, 45%, 55%, and 65% also formed a barrier. Therefore, specific combinations of glycerin and xanthan gum were identified that can form a barrier that prevents passage of microorganisms in an in vitro filter insert-based model.

TABLE XI

| | | Examples 104-112 | Example 113 | Examples 114-121 | Examples 122-129 | Examples 130-137 | Examples 138-145 | Examples 146-153 |
|---|---|---|---|---|---|---|---|---|
| | | Xanthan Gum (%) | | | | | | |
| | | 0 | 0.005 | 0.01 | 0.05 | 0.1 | 0.2 | 0.4 |
| Glycerine (%) | 0 | No | No | No | No | No | No | No |
| | 5 | No | | No | No | No | Yes | No |
| | 7 | No | | Yes | | | | Yes |
| | 15 | No | | No | No | No | Yes | Yes |
| | 25 | No | | No | No | No | Yes | Yes |
| | 35 | No | | No | No | No | Yes | Yes |
| | 45 | No | | Yes | No | No | Yes | Yes |
| | 55 | Yes | | Yes | No | No | Yes | Yes |
| | 65 | Yes | | Yes | No | No | Yes | Yes |

'No': no barrier formed;
'Yes': barrier formed

Microbial cells retained by the compositions of Examples 104-153 formed on filter inserts were trapped by the barrier, and were viable, thus demonstrating that the formed barrier does not have an inherent antimicrobial property without an antimicrobial agent. In other words, the microbes retained in the barrier were still active and could pose a threat to infection; for example, if they are freed from the barrier by abrasion or after the barrier loses its integrity.

It should be noted that an effective barrier or coating may be formed at lower concentrations of glycerine and/or xanthan gum when an effective antimicrobial is added. This is because the antimicrobial and barrier act in tandem to stop and/or kill the harmful microbes.

Examples 154-160

Examples 154-160 were performed to demonstrate safety of the composition on mucosal surfaces. Patent publication U.S. 2012/0270909 as well as the provisional applications that this application claims the benefit of priority to include this information.

Example 161

Glycerine-Xanthan Gum Formulations Form a Coating on the Human Oral Mucosa

Figure 21:
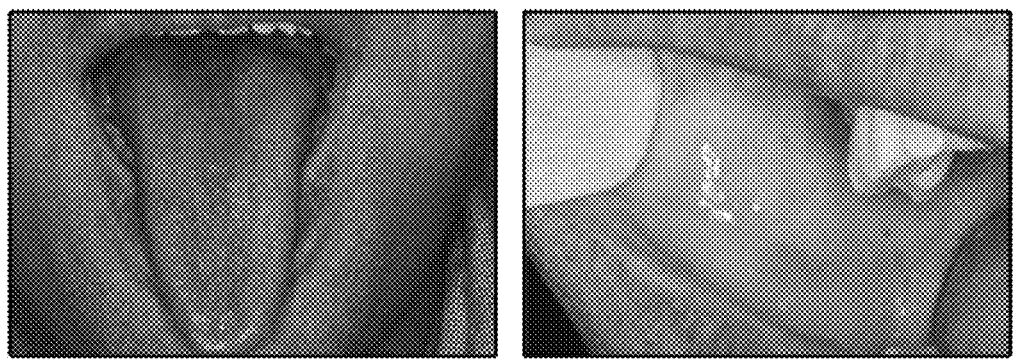
FIG. 21 are photographs demonstrating the ability of an example barrier-forming composition to coat the oral mucosal surface.

To determine whether glycerine-xanthan gum formulation can form a coating on the human oral mucosa, we spiked the Example 7 formulation with Gentian Violet (GV) as a marker dye. The spiked product (750 µL) was sprayed onto the oral cavity of human volunteers. Post-application, the oral cavity was inspected for staining, and the images were captured using a digital camera. As shown in FIG. 21, the formulation stained both cheeks and the dorsal/ventral surface of the tongue.

Examples 162 and 163

Exposure of Microbes to Barrier-Forming Composition Inhibits Cell Growth: Time-Lapse Microscopy To determine the inhibitory activity and duration for which barrier-forming compositions exhibit activity against microbes, time-lapse analysis was performed on cells exposed to the barrier-forming composition, compared to untreated bacteria and fungi.

In Example 162, *S. mutans* microbial cells were exposed to Example 7 for one minute, washed to remove any residual agent, and allowed to grow in a petri-dish containing fresh growth medium. Growth of organisms at 37° C. was monitored for a 6 hour period, and photomicrographs were taken every 20 minutes over the 6 hour incubation period using a camera connected to the microscope.

In control Example 163 the same procedure was followed with untreated cells.

Figure 22:
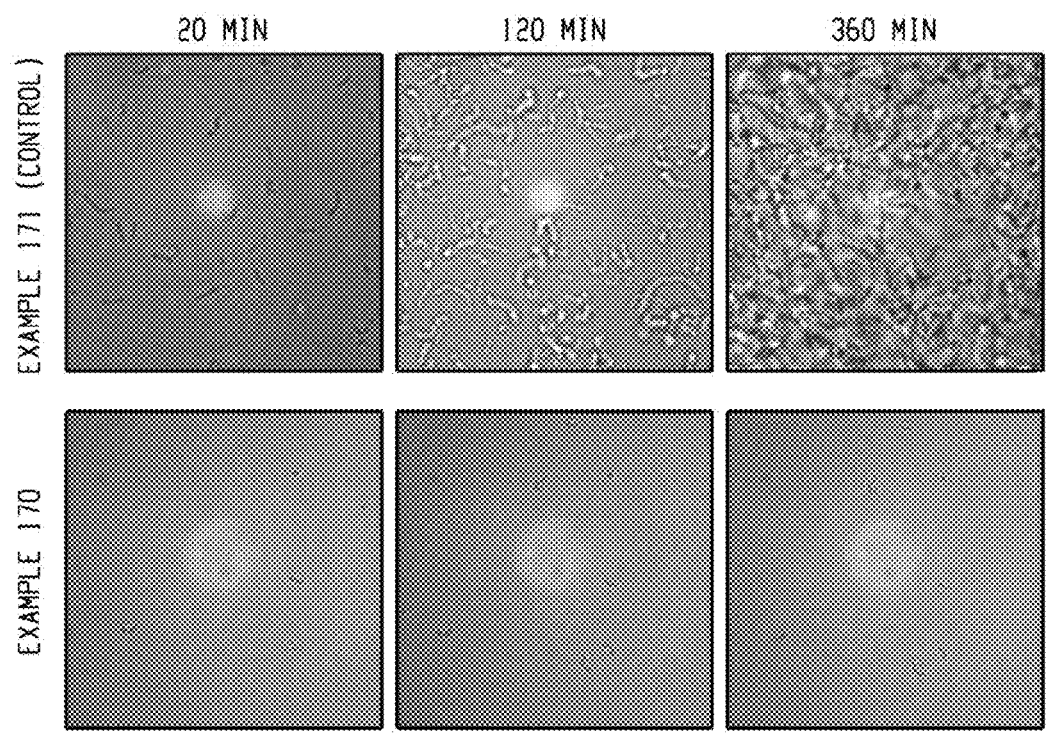
FIG. 22 are photographs showing time-lapse microscopy of bacterial growth after a 1 minute exposure to an example barrier-forming composition, as described in Examples 162-163. Images represent bacterial growth after 20 min, 120 min, or 360 min post-exposure.

As shown in FIG. 22, in contrast to the untreated bacteria, where cells reached confluence by 6 hours, microbes treated with the Example 7 barrier-forming composition failed to regrow during the same time period post-exposure. Similarly, exposure of *Candida* cells to the Example 7 barrier-forming composition completely inhibited growth during the incubation period (data not shown).

These results further confirmed that the barrier-forming composition possesses prolonged antimicrobial activity.

Examples 164-166

In Vivo Study: Barrier-Forming Composition (Example 7) Lowers the Oral Microbial Load in Humans: Short- and Long-Term Activity Short-Term Activity The duration of activity of Example 7 was determined in healthy individuals by evaluating the effect of a single application on microbial burden of the oral cavity. In Examples 164-166, three healthy individuals (over 18 years of age, healthy mouth) were enrolled with informed consent, and asked to apply a single application of the composition of Example 7 on their cheeks. A single application was defined as three sprays of 0.25 ml each in volume. Next, swabs were collected from these individuals at baseline (pre-treatment), 1 hour, 2 hours, and 6 hours post-treatment. Swabs were cultured on agar media plates specific for aerobic or anaerobic organisms, incubated for 24-28 hours at 37° C., and the number of CFUs were counted. Effect of Example 7 on microbial burden was determined (CFUs), and percentage inhibition was calculated for each post-exposure time point relative to the baseline (0 minutes) CFUs.

Figure 23:
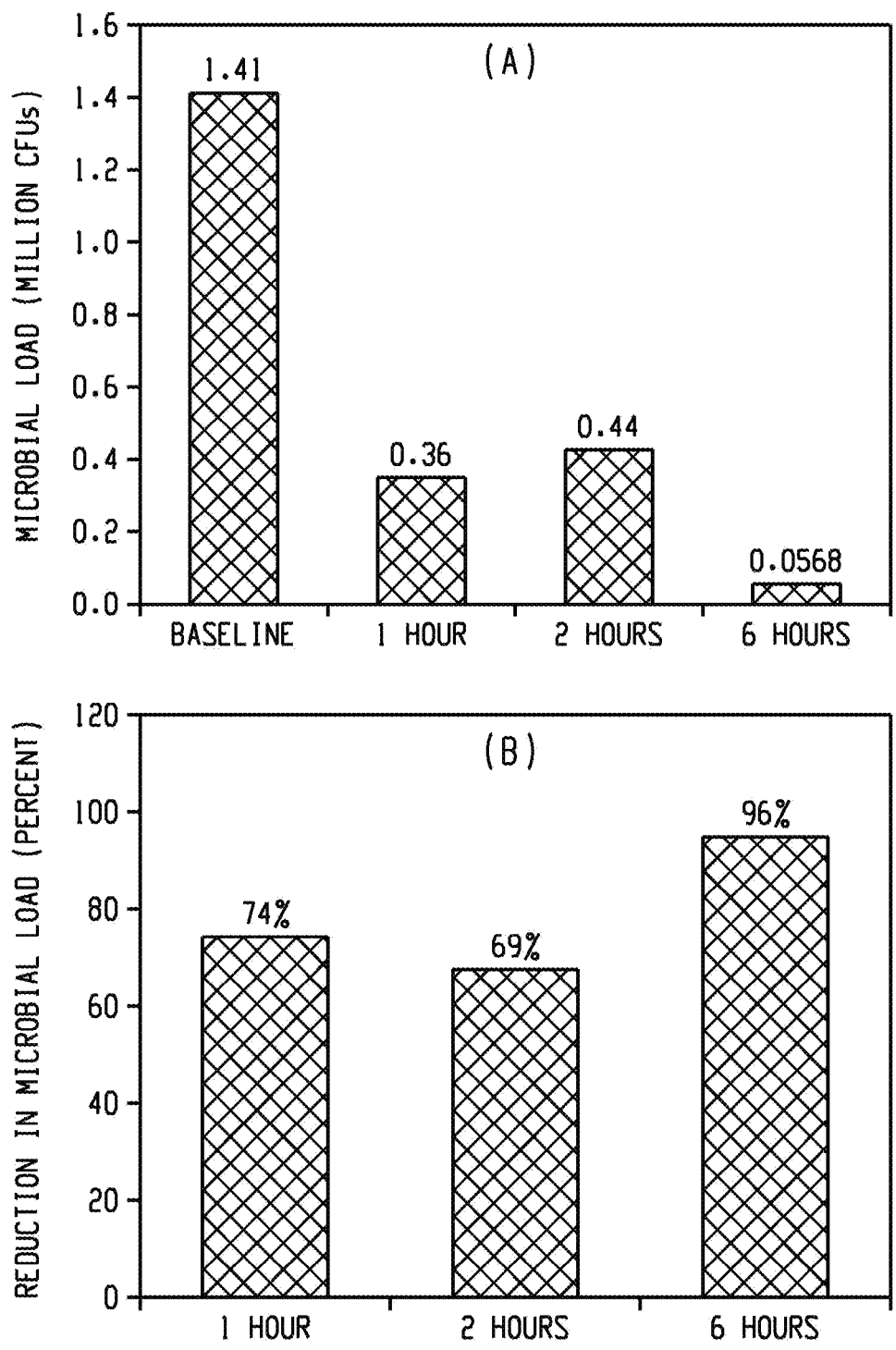
FIG. 23 is a graph showing the effect of a single dose of an example barrier-forming composition on oral microbial burden of a healthy individual, as described in Example 164-166. (A)—Microbial load in CFUs, (B) reduction in microbial load (%) compared to baseline.

The results showed that application of Example 7 led to consistent reduction in microbial load for up to 6 hours (See FIG. 23A, which shows CFUs of a representative tested individual. Treatment with the barrier-forming composition resulted in 69% to 96% reduction of the microbial burden in the oral cavity (See FIG. 23B, which shows a representative individual's reduction in microbial load.)

Examples 167-169

The activity of the barrier-forming composition over a 5-day period against oral microbes was evaluated. In Examples 167-169, three healthy individuals were enrolled, and asked to apply a single dosage (three sprays 0.75 mLs total) of Example 7 three times daily (approximately 9 AM, noon, and 3 PM) for a 5-day period (representing a typical 5-day work-week). Swabs were collected from these individuals at baseline (before application on day 1) and at the end of the day on each day during the 5-day period. Collected swabs were cultured on agar media plates, incubated for 24-28 hours at 37° C. and at 5% $CO_2$ humidity, and the number of CFUs were counted.

Figure 24:
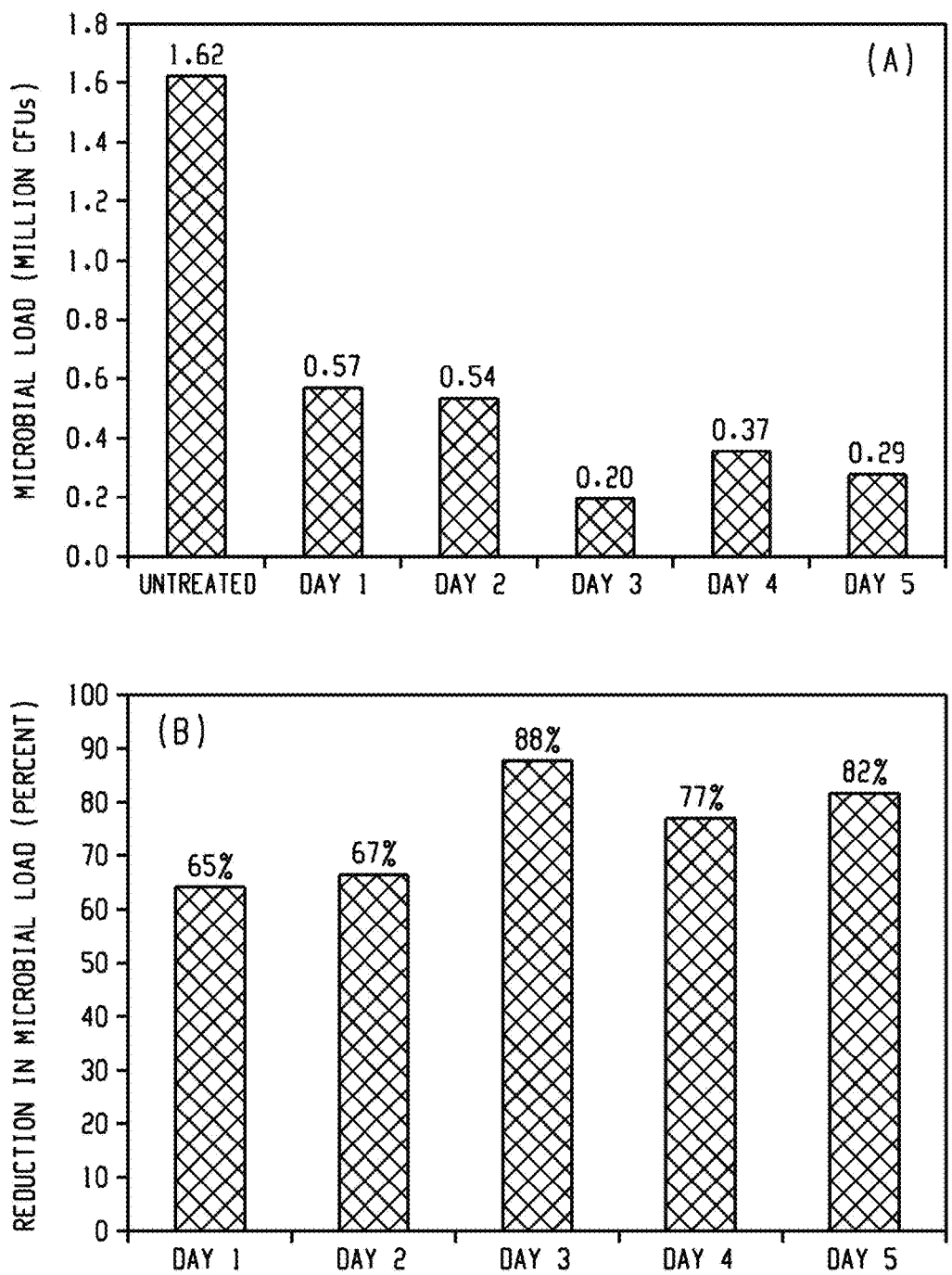
FIG. 24 is a graph showing the effect of an example barrier-forming composition on levels of oral microbes over a 5-day period in three healthy adults, as described in Examples 167-169.

The effect of the Example 7 barrier-forming composition on microbial burden was determined (as median CFUs for the three subjects), and percentage inhibition was calculated for each post-exposure time point relative to the baseline (0 min) CFUs. FIG. 24 shows these results in a graph of CFUs versus time (FIG. 24A) and reduction in microbial load versus time (FIG. 24B). Examples 167-169 demonstrate that application of Example 7 over 5 days led to consistent reduction in microbial load over the 5-day test period (FIG. 24A). Treatment with the Example 7 barrier-forming composition resulted in 65%-88% reduction of the median microbial burden in the oral cavity of the study participants (FIG. 24B).

Examples 170-198

Figure 25:
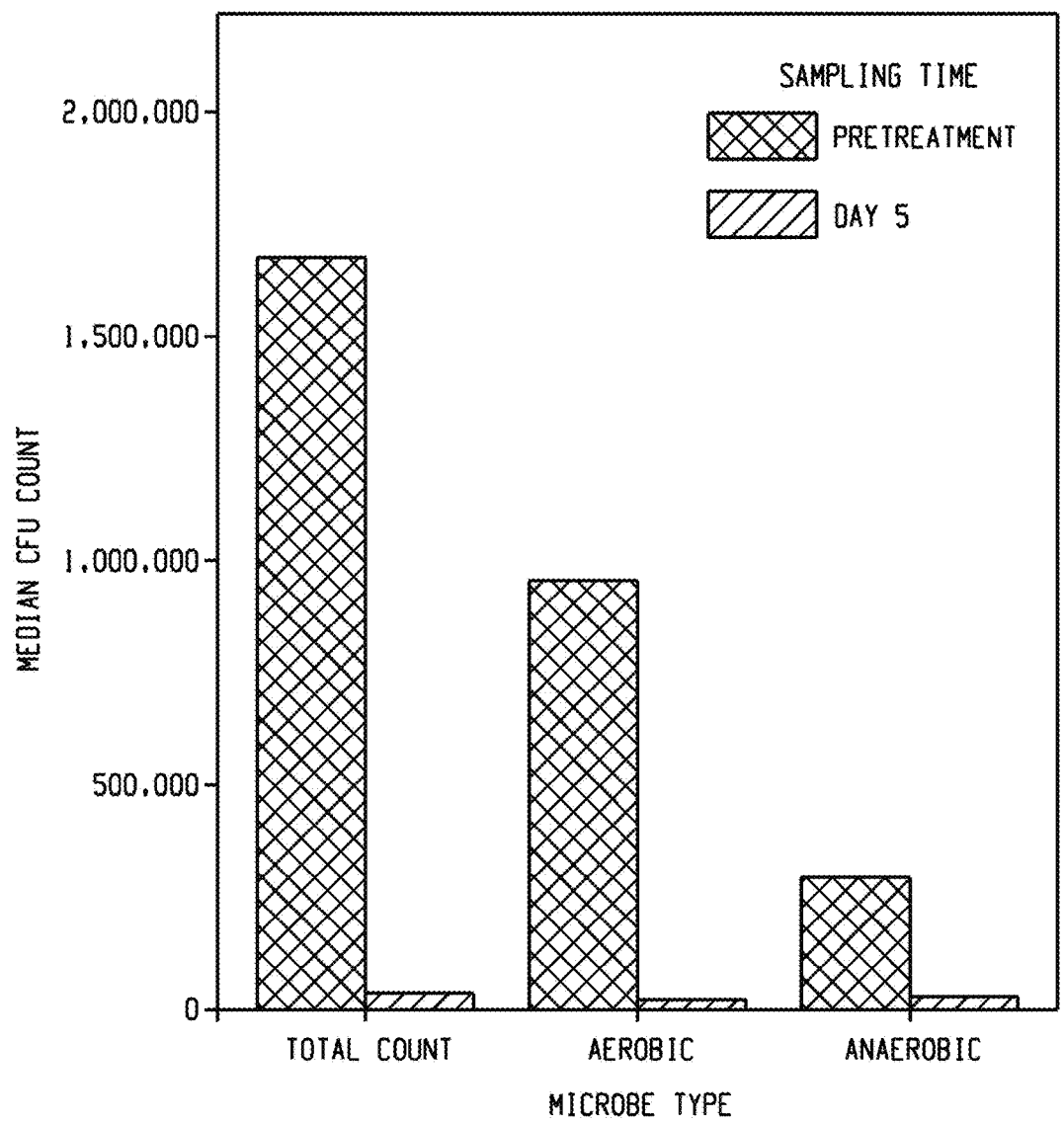
FIG. 25 is a graph showing the effect of an example barrier-forming composition on microbial burden of the oral cavity after 5-day usage in 31 healthy subjects, as described in Examples 170-198.
Figure 26:
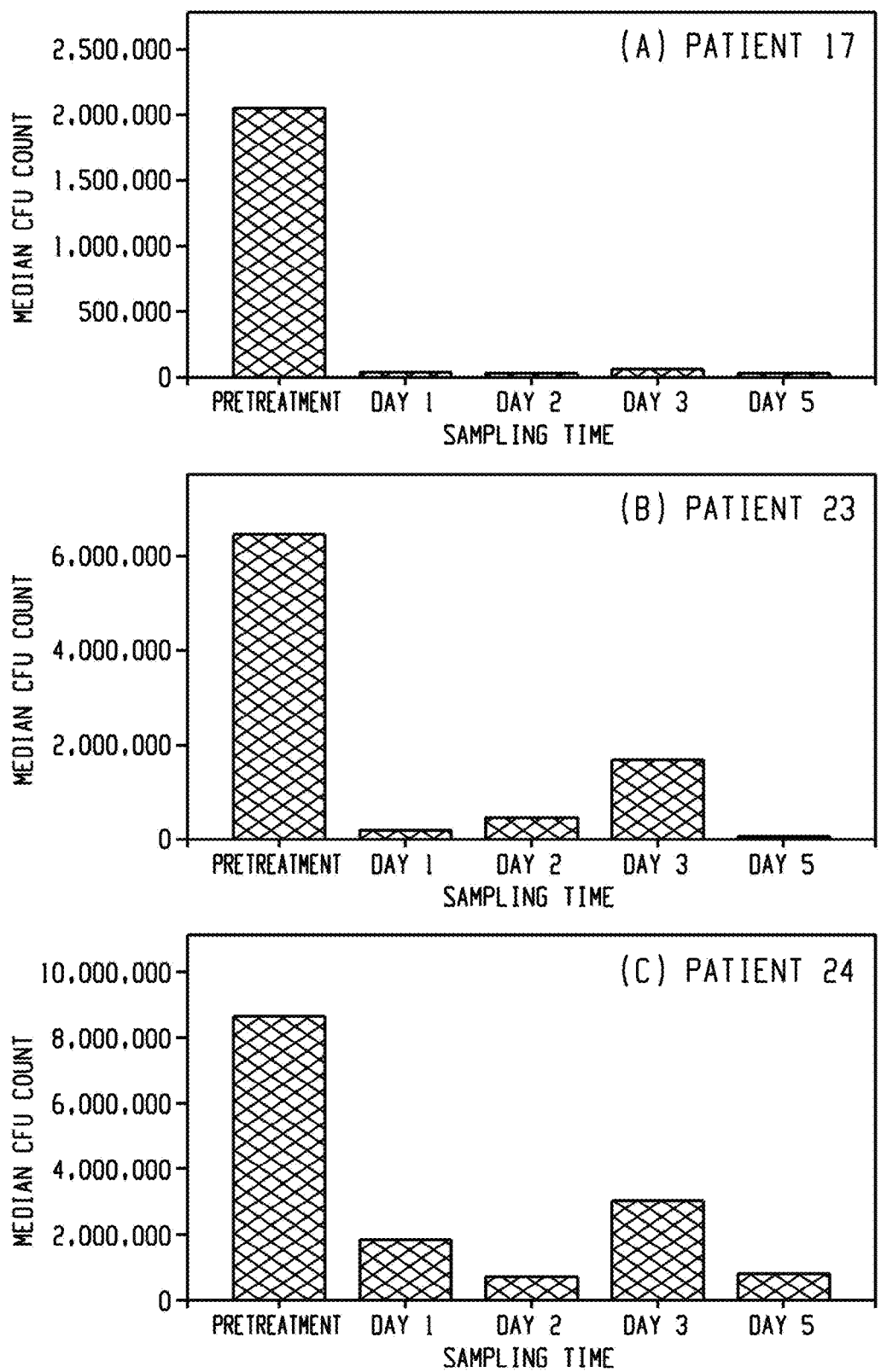
FIG. 26 is a graph showing the microbial load in oral samples obtained from three representative study participants, as described in Examples 170-198.

In a clinical study, twenty-nine healthy individuals were enrolled after informed consent. Baseline information was recorded (age in years, gender, ethnicity, and date of enrolment). Oral examination of the mouth was undertaken, and the inside of the mouth (cheek) was swabbed with a sterile culture swab. Baseline oral swab samples were cultured to determine bacterial load prior to study. In Examples 170-198, each of the twenty-nine participants were given a spray bottle containing the barrier-forming composition of Example 7 and instructed to spray the inside of their mouth for a total volume of 0.75 ml, then swish for 30 seconds and swallow. Two groups of approximately equal number of participants were tested. One group used the example barrier-forming composition every two hours, three times a day, for five days (a typical work week). The other group used the example barrier-forming composition every two hours, four times a day, for five days (a typical work week). No substantial difference was noted in the two groups. Swabs were collected on days 1, 2, 3, and 5 at the end of the day (8 hours after the first administration of the barrier-forming composition) and cultured on media specific for aerobic and anaerobic bacteria. Data were presented as number of microbes: total, aerobic and anaerobic. FIG. 25 shows a graph of total microbial load and breaks down the total into aerobic and anaerobic counts from just prior to treatment and on day 5 of treatment. FIG. 26 shows graphs of microbial load over the 5 day period in oral samples obtained from three representative study participants.

Overall, the in vivo testing showed that the barrier-forming composition exhibits antimicrobial activity against oral microbes, as measured by reduction in the levels of these organisms, over both short- and long-term duration.

The data showed that treatment with the barrier-forming composition over a 5-day period resulted in reduction in the oral microbial load, for total microbes, aerobic and anaerobic organisms.

Example 199-205

Identification of Additional Humectants for Forming a Barrier to Prevent Microbial Penetration In Example 199 an in vitro filter insert-based model (see FIG. 27) was used to test different humectants at different concentrations.

Six compositions were prepared according to Table XII based on the mixing procedures used for Examples 3-8.

TABLE XII

|  | Ex. 199 | Ex. 200 | Ex. 201 | Ex. 202 | Ex. 203 | Ex. 204 | Ex. 205 |
|---|---|---|---|---|---|---|---|
| Xanthan Gum | 0.4 | 0.4 | 0.4 | 0.4 | 0.4 | 0.4 |  |
| Glycerin | 4.5 | 4.5 | 4.5 |  |  |  | 4.5 |
| Sorbitol |  | 4.5 | 4.5 | 4.5 |  | 4.5 |  |
| Xylitol |  |  | 4.5 | 4.5 | 4.5 |  | 4.5 |

Next, 100 μL of Examples 199-205 were placed into filter inserts (pore size 0.8 μm diameter, that allows both bacteria and fungi to pass through) and allowed to form a layer. Next, organisms were overlaid on the layer formed by the test solutions. The filter inserts containing the layer of test solutions and microorganisms were then placed on the surface of agar media plates and incubated for 24 hours at 37° C. After the incubation period, the agar media plates were evaluated for growth on filter insert and in the agar media. Growth on filter insert but no growth in agar media indicated that the test solution formed a barrier, which prevented the microbes from passing through. In contrast, microbial growth in the filter insert as well as the agar media indicated that no such barrier was formed.

The results showed that each of the xanthan gum-based solutions containing the tested humectants (singly or in combination) formed intact barriers on the filter insert that prevented the passage of microorganisms into underlying agar medium.

Example 206-213

Determination of the Solubility Limits of Xanthan Gum

To determine the solubility of xanthan gum, it was mixed at different concentrations in water and the solubility observed by monitoring the presence or absence of clumps and free flow of the mixture. Table XIII reports the results and concentrations.

TABLE XIII

| Example | Xanthan Gum Concentration | Solubility |
|---|---|---|
| 206 | 0.40% | free flowing viscous solution |
| 207 | 0.45% | some clumps, viscous solution |
| 208 | 0.5% | more clumps, viscous solution |
| 209 | 0.6% | clumps, more viscous than above |
| 210 | 0.7% | clumps, more viscous than above |
| 211 | 0.8% | Extensive clumps, highly viscous solution, no free flow |
| 212 | 0.9% | Extensive clumps, highly viscous solution, no free flow |
| 213 | 1.00% | Extensive clumps, highly viscous jelly, no free flow |

We found that when mixed at 0.4%, xanthan gum formed a free-flowing solution (Table XIII). In contrast, mixtures containing 0.45% or 0.5% xanthan gum formed a viscous fluid but contained small clumps. The extent of clumps increased with increasing concentration of xanthan gum (0.6% and 0.7%). At concentrations ≥0.8%, xanthan gum mixture contained extensive clumps, with a jelly-like consistency and no free flow.

Example 214

Comparison of Cationic CPC in Barrier-Forming Composition with Neutral Antimicrobial Agent in Barrier-Forming Composition In Example 214, the formulation of Example 7 was made, except the neutral agent Citral was used instead of CPC. The antimicrobial activity of formulations containing CPC (0.1%) or Citral (0.5%) against Streptococcus was ascertained. The assay described above in Examples 48-61 was used to perform these studies.

The results showed that the formulation containing citral exhibited antimicrobial activity (MIC=12.5%). However, activity of formulation containing citral was significantly less potent than that containing CPC (MIC=0.098%).

Example 215

Physico-Chemical Testing of Hydrophobicity and Comparison

In Example 215 thin layer chromatography analysis was used to compare the hydrophobicity of Example 7 with a hydrophobic composition. The hydrophobic composition was comprised of the components in Table XIV.

TABLE XIV

|  | Wt % |
|---|---|
| Glycerin | 7 |
| Sorbitol | 5 |
| Poloxamer 338 | 1 |
| PEG 60 Hydrogenated castor oil | 1 |
| VP/VA copolymer | 0.75 |
| Sodium benzoate | 0.5 |
| Cellulose Gum | 0.2 |
| CPC | 0.05 |
| Methyl Paraben | 0.05 |
| Propyl paraben | 0.05 |
| Sodium Saccharin | 0.05 |
| Xanthan Gum | 0.01 |

TABLE XIV-continued

| | Wt % |
|---|---|
| Disodium Phosphate | 0.006 |
| Flavoring and coloring agents | 0.121 |

*the remainder of the composition was purified water

10 μL of Example 7 and the hydrophobic composition were deposited on pre-made TLC plates (at a distance of 2 cm from the bottom edge). The spots were air-dried for 5 minutes, and the plates were placed in a TLC chromatography jar containing water as a solvent. The TLC system was allowed to run until the solvent front reached the top edge of the plate. Plates were removed and the solvent and sample fronts were marked. The Relative Front (Rf) values were calculated for the two samples using the formula I:

$$Rf = \text{Distance Traveled by Spot/Distance Traveled by Solvent Front} \qquad \text{I}$$

The results showed that the Rf value for the hydrophobic composition and Example 7 were 0.33 and 0, respectively, indicating that the hydrophobic composition was highly miscible in water. In contrast, Example 7 did not exhibit any mobility in the aqueous solvent, demonstrating that this formulation is hydrophobic or not hydrophilic.

Example 216

A barrier-forming composition was made by mixing the components according to Table XV below in water to form a solution. A eucalyptol component was also included in an amount of 5× per the Homeopathic Pharmacopeia, but also did not affect the test results, other than demonstrating that the composition still works with this component added into it. All percentages are by weight.

TABLE XV

| | Antimicrobial (CPC) | Humectant (Glycerin) | Gum (Xanthan Gum) |
|---|---|---|---|
| Example 216 | 0.01% | 35% | 0.4% |

Examples 217-219

The barrier-forming composition was also shown to have effectiveness in killing allergy causing molds. MIC tests were performed on a polystyrene plastic surface.

In Example 217 the barrier-forming composition of Example 216 was tested to determine its MIC against *Stachybotrys* MRL 9740. The Example 7 composition had an MIC of 0.06 micrograms/ml.

In Example 218 the barrier-forming composition of Example 216 was tested to determine its MIC against *Aspergillus fumigatus* 18748. The Example 7 composition had an MIC of 0.49 micrograms/ml.

In Example 219 the barrier-forming composition of Example 216 was tested to determine its MIC against *Cladosporium*. The Example 7 composition had an MIC of 0.39 micrograms/ml.

Because *Stachybotrys* and *Aspergillus fumigatus* are mold-causing organisms, these examples further support the embodiment wherein the barrier-forming composition is applied to surfaces to prevent or treat mold growth or discoloration.

Examples 219-224

In Examples 219-224 the effect of barrier-forming composition on MRSA biofilm formation on a silicone elastomer disc surface was evaluated.

In Examples 219-221, three silicone elastomer discs with a 1 cm diameter were pre-sprayed with 0.25 mL with the Example 7 barrier-forming composition for 60 min and incubated at 37° C. In Examples 222-224 a control example was performed by treating a silicone elastomer disc with an equivalent amount of a phosphate-buffered saline (PBS) for 60 minutes and incubated at 37° C.

The Example 219-224 pretreated discs were each submerged in 4 mL MRSA suspension ($1 \times 10^7$ cells/mL), and incubated at 37° C. for 90 min ("Adhesion Phase"). Next, the discs with adherent cells were removed and transferred to wells containing 4 mL of Brain Heart Infusion (BHI). The wells were incubated at 37° C. on a rocker for 24 hours. Biofilm formation on the discs was evaluated by quantitative culturing on BHI agar plates. Scanned images of the wells were recorded using a scanner.

Figure 28:
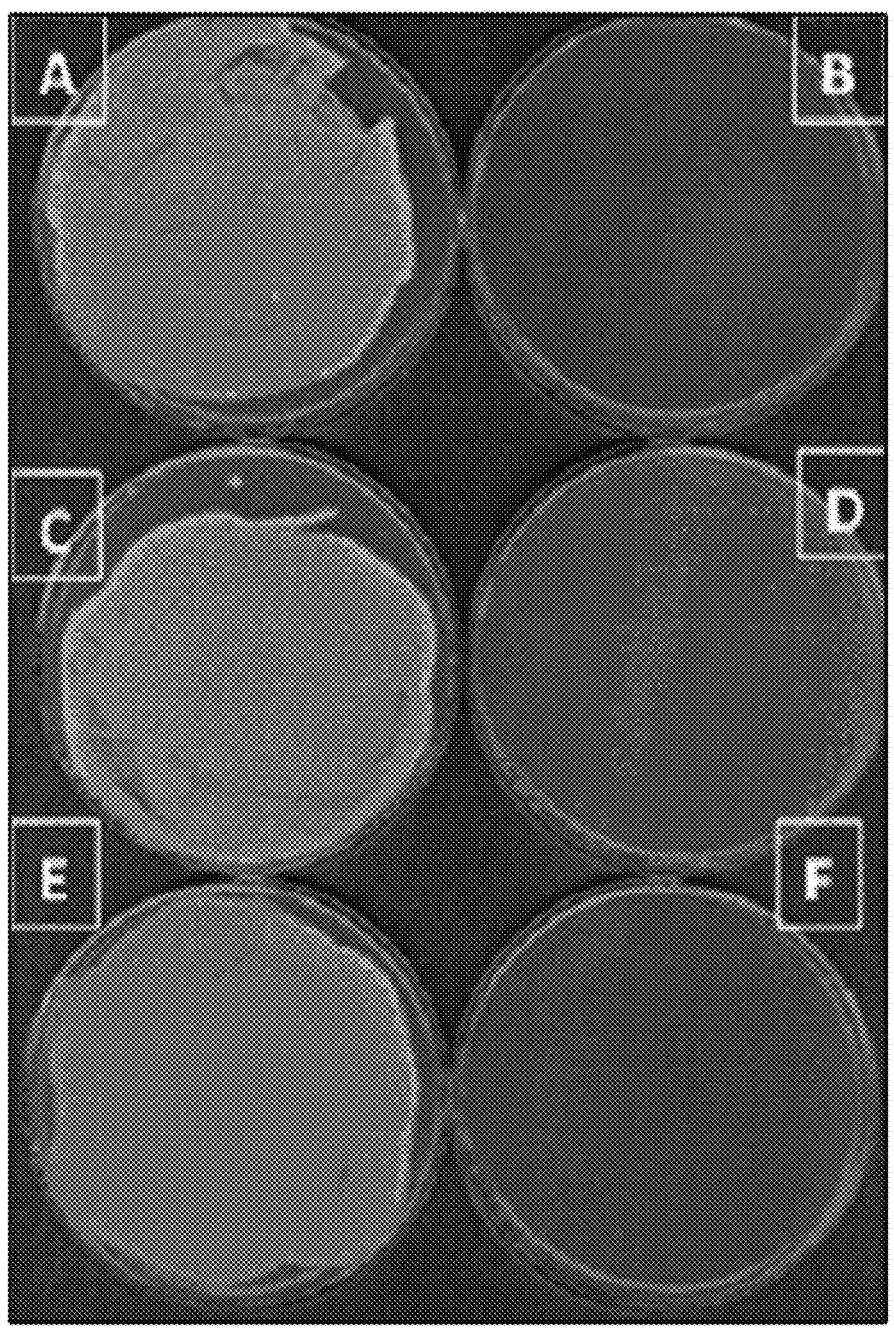
FIG. 28 is a set of photographs showing growth of MRSA biofilms on the surface of silicone elastomer discs treated with PBS (control, A, C, E) and Example 7 barrier forming composition (B, D, F), as described in Examples 219-224.

As shown in Table XVI, pre-treatment with Example 7 barrier-forming composition prevented formation of biofilms on the disc surface. FIG. 28 shows images of colony burden in biofilms formed by MRSA on the PBS treated (A, C, E) and Example 7 treated (B, D, F) discs.

TABLE XVI

| Treatment | Example | MRSA CFUs/mL |
|---|---|---|
| Example 7 barrier-forming composition | 219 | 0 |
| | 220 | 0 |
| | 221 | 0 |
| PBS | 222 | $1.58 \times 10^8$ |
| | 223 | $1.72 \times 10^8$ |
| | 224 | $1.53 \times 10^8$ |

Examples 225-246

The Example 7 barrier-forming composition was tested to determine its efficacy against several strains of *Bordetella pertussis*. In test Examples 225-235, agar-based assays were constructed in which Example 7 barrier-forming compositoin was incorporated in Regan-Lowe Charcoal agar BBL #297883 plates as a 64 microgram/mL dilution in water. Control Examples 236-246 were agar plates containing no Example 7 barrier-forming composition. In each of Examples 225-246 $5 \times 10^4$ cells (50 uL) of *Bordetella pertussis* were spotted on the test surface and plates were incubated at 37 degrees C. for 24 hours. As shown in Table XVII, confluent growth was observed in control Examples 236 to 246, while no growth was observed in test Examples 236-246. The designation 4+ means luxurious growth.

TABLE XVII

| Example | *Bordetella pertussis* Strain # | Microbial Growth |
|---|---|---|
| 225 | J11E | None |
| 226 | J11F | None |
| 227 | J14B | None |
| 228 | J14C | None |
| 229 | J14D | None |
| 230 | J14G | None |
| 231 | J32B | None |
| 232 | J32C | None |

TABLE XVII-continued

| Example | Bordetella pertussis Strain # | Microbial Growth |
|---|---|---|
| 233 | J32D | None |
| 234 | J36E | None |
| 235 | J36F | None |
| 236 | J11E | 4+ |
| 237 | J11F | 4+ |
| 238 | J14B | 4+ |
| 239 | J14C | 4+ |
| 240 | J14D | 4+ |
| 241 | J14G | 4+ |
| 242 | J32B | 4+ |
| 243 | J32C | 4+ |
| 244 | J32D | 4+ |
| 245 | J36E | 4+ |
| 246 | J36F | 4+ |

Examples 247-252

The antiviral activity of the barrier-forming composition, Example 7 (in various diluted concentrations) was evaluated against the ATCC VR-1200 strain of rhinovirus.

Human Hepatoma (HUH-7) Cells were prepared in 24-well plates with Dulbecco's Modified Eagle Medium (DMEM) with 10% heat inactivated fetal calf serum and supplemented with L-glutamine (Lglu) and penicillin/streptomycin (P/S) (unless specified, all reagents produced by Gibco, N.Y., USA). All culture cells were grown to 90-100% confluence at 37° at 5% $CO_2$ and then washed with OptiMEM +P/S+Lglu once prior to infection.

In Examples 247-251, the Example 7 composition was applied to cell monolayers at varying concentrations (5%, 10%, 15%, 20%, 50% diluted in 400 microliter optiMEM (+P/S, +Lglu)) for a working CPC concentration of 0.005%, 0.01%, 0.015%, 0.02% and 0.05% respectively, and was allowed to dwell for 1 hour prior to inoculation. In control Example 252 400 microliter optiMEM (+P/S,+Lglu) was applied to the cells and allowed to dwell for 1 hour prior to inoculation.

The cell monolayers were then removed from the Example 7 dilutions or control optiMEM and rhinovirus was applied at a multiplicity of infection (MOI) of 0.1. Cells were incubated with virus at 32.5° C. for 1 hour. After which the inoculum was removed and 500 ul OptiMEM +P/S+Lglu was placed on the cells. Cells were then grown at 32.5° C. at 5% CO2. After 5 days incubation, cell culture supernatants were collected for rhinovirus viral load quantification.

Rhinovirus viral titer of the Example 247-251 cell culture supernatants were measured by real time PCR. In comparison to Control Example 252 significantly decreased rhinovirus viral load was demonstrated in Example 251, which was a 50% concentration of Example 7. See Table XVIII below.

TABLE XVIII

| Example | Wt. % Example 7 | Amount | Viral load/mL |
|---|---|---|---|
| 247 | 5% | 303354.64 | 12141854.69 |
| 248 | 10% | 5628.209 | 2251283.75 |
| 249 | 15% | 92717.83 | 37087131.25 |
| 250 | 20% | 8776.60 | 3510638.67 |
| 251 | 50% | 0 | 0 |
| 252 | 0 (control) | 95307.36 | 38122943.75 |

Examples 253 and 254

A test Example 253 was formulated with a 50% Example 7 diluted suspension (0.05 CPC concentration) in 500 microliter optiMEM (+P/S,+Lglu). A control Example 254 was formulated as a control solution with no Example 7 (500 microliter optiMEM (+P/S,+Lglu)). Examples 253 and 254 were applied the cells disclosed in Examples 246-252, but at defined intervals: T—1 hour, T—30 min, and T—0 (Immediate) prior to infection.

The cell monolayers were then removed from the Example 253 suspension and the Example 254 control solution. The rhinovirus viral particles were applied to the treated cell monolayers at a multiplicity of infection (MOI) of 0.1. Cells were incubated with virus at 32.5° C. for 1 hour. After which the inoculum was removed and 500 ul OptiMEM +P/S+Lglu was placed on the cells. Cells were then grown at 32.5° C. at 5% $CO_2$ for 5 days. The cells treated with Example 253 and 254 were viewed daily for the presence of cytopathic effect. After 5 days incubation, cell culture supernatant was gathered for immunofluorescence and rhinovirus viral load quantification.

Figure 29:
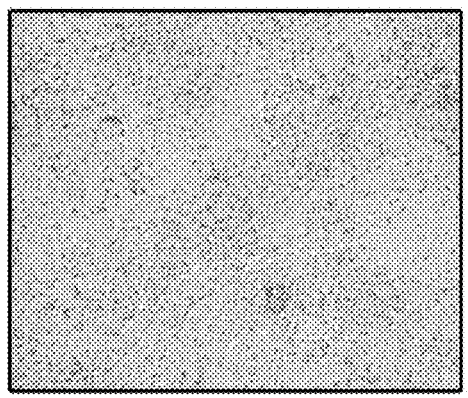
FIG. 29 is a set of photographs showing cell monolayers treated with an embodiment of the barrier-forming composition, Example 252, for varying time periods (a), (b), and (c), and a control Example 253 (d).
Figure 29:
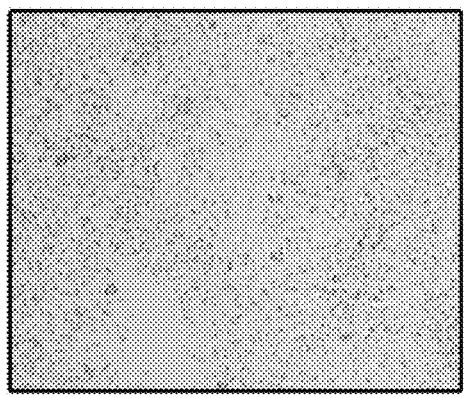
Figure 29:
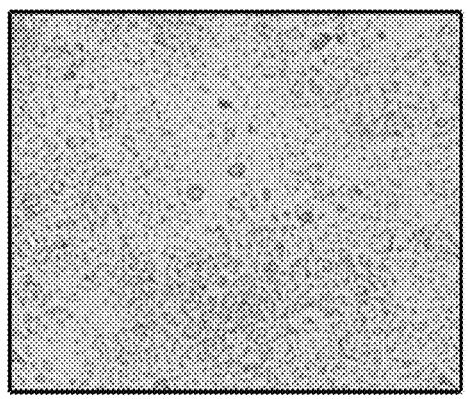
Figure 29:
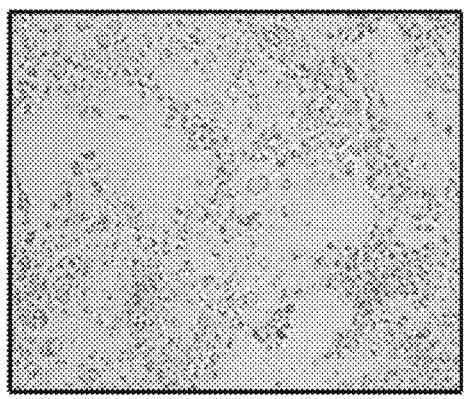

FIG. 29 discloses photos of cells treated with test Example 253 at FIG. 29(a) T—1 hr, FIG. 29(c) T—30 min and FIG. 29(b) T 0 (immediate). None of these photos demonstrated any cytopathic effect and healthy cells overgrew the plate. However, as shown in FIG. 29(d) the Example 254 untreated control cells demonstrated focal rounding, detachment and cell death. Cytopathic effect determination included the development of focal rounding, cell size enlargement or reduction, syncytial formation, development of multinucleated giant cells, and detachment.

Immunofluorescence was determined as follows: Virus infected cell monolayers and uninfected control were washed with sterile PBS. The cells were trypsinized, spotted upon wells on slides and fixed with acetone. The slides were tested by DFA employing FITC labeled monoclonal antibodies. An indirect immunofluorescence assay was performed using Light Diagnostics Pan-Enterovirus Detection Kit (Millipore). This detection kit is well described for having cross reactivity with rhinovirus infected cells. All antibody dwell steps occurred for 1 hour at 37° C. Following a final wash, cells were evaluated at a wavelength of 488 nm for the presence of fluorescence.

Figure 30:
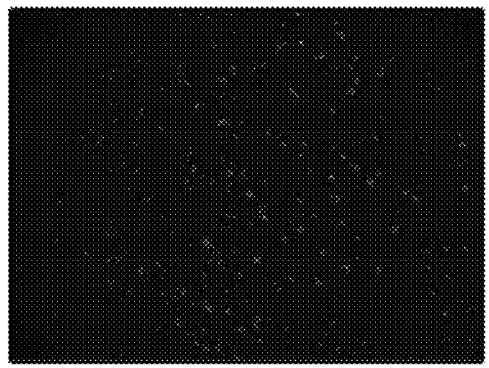
FIG. 30 is a set of immunofluorescence photographs showing cell monolayers treated with an embodiment of the barrier-forming composition, Example 252, for varying time periods (a), (b), and (c), and a control Example 253 (d).
Figure 30:
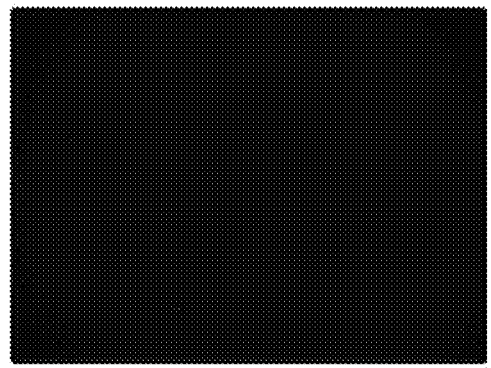
Figure 30:
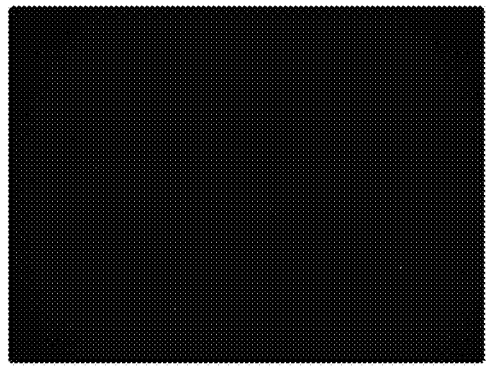
Figure 30:
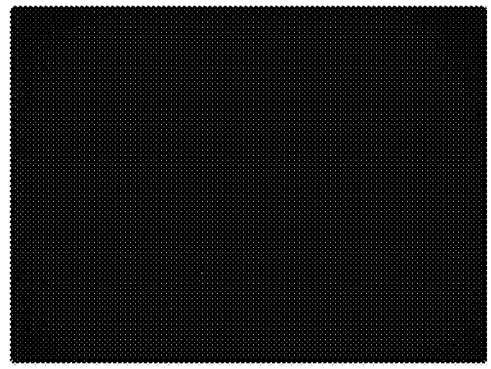

FIG. 30 discloses immunofluorescence photos of cells pretreated treated with test Example 253 at FIG. 30(d) T—1 hr, FIG. 30(b) T—30 min and FIG. 30(c) T—0 (immediate). The cells treated with Example 253 for 1 hour and 30 minutes displayed no immunofluorescence. The cells treated with Example 253 for T—0 (immediate) demonstrated scant fluorescence. However, the untreated control Example 254 showed substantial immunofluorescence suggesting profound viral infection (FIG. 30(a)).

Viral load for the samples was quantified as follows: Cell culture supernatants were collected and stored at −80° C. Nucleic acid was extracted using QIAamp Viral RNA Kit (QIAGEN, Valencia, Calif.). Random hexamer primers (Invitrogen Carlsbad, Calif.) were used to create a cDNA library for each specimen. Reverse transcription reactions were performed with M-MLV RT (Invitrogen, Carlsbad, Calif.) according to the manufacturer's specifications. Quantitative analysis was performed on a StepOne Plus Taqman Real Time PCR (Applied Biosystems, Branchburg, N.J.) using TaqMan Universal PCR Master Mix (Applied Biosystems, Branchburg, N.J.), 2 microliter of cDNA sample, and primers/probes targeting the rhinovirus polyprotein gene. A reference standard was prepared using an amplicon amplified by conventional RT-PCR, gel purified (QIAquick, Qiagen, Valencia, Calif.), and quantified using a spectrophotometer (Beckman Coulter, Brea, Calif.). The results are shown in Table XIX.

TABLE XIX

|  | Amount | Viral load/mL |
|---|---|---|
| Example 253: 1 hour pretreatment | 0 | 0 |
| Example 253: 30 minute pretreatment | 0 | 0 |
| Example 253: Immediate pretreatment | 0 | 0 |
| Example 254 (control) | 331025.2 | $1.32 \times 10^8$ |

No rhinovirus amplification was apparent at T—1 hour, T—30 min, or T—0 (immediate) timepoints at 5 day post infection. Untreated (control) cells demonstrated substantial amplification ($>10^8$ copies/ml) suggesting viral infection.

Example 255

Cetylpyridinium Chloride Composition Exhibits Antimicrobial Activity on Inanimate Surfaces In Example 255 a cetylpyridinium chloride-based spray disinfectant was evaluated for its activity against methicillin-resistant *Staphylococcus aureus* (MRSA). The antibacterial effect of pre-coating surfaces with the composition was analyzed, and the effect of a water rinse on maintaining its activity was also analyzed.

In an embodiment, the barrier-forming composition containing cetylpyridinium chloride retains a substantial amount of its cidal or static activity even on stainless steel surfaces after washing with water, such as at least about 35%, about 35% to about 50%, or about 15% to about 40% of cidal or static activity after washing with water.

The test CPC composition had the following formula: 93% to 97% water, 0.5 to 1% CPC antimicrobial, 0.5 to 1% glycerin, with the remainder of the composition comprising preservatives, such as cremophor RH 60, copovidone, parabens, and sodium benzoate, none of which were present in an amount more than about 1%.

The activity of the test CPC composition ($CPC_{sd}$) was evaluated by soaking stainless steel carriers with MRSA suspension ($1 \times 10^8$ cells) for 15 min at 37° C. Next, excess fluid was drained, the carriers sprayed with $CPC_{sd}$ (0.5 mL dosages) for 30 seconds, air dried, and incubated in Brain heart infusion medium (BHI) overnight. Aliquots of the medium were then quantitatively cultured.

To determine the effect on pre-coated carriers, discs were sprayed with $CPC_{sd}$, (0.50 mL dosages), air-dried for 2-4 minutes, and inoculated with MRSA for 15 minutes at 37° C. Excess fluid was drained and carriers incubated in BHI overnight followed by quantitative culture.

The results showed that $CPC_{sd}$ inhibited the growth of MRSA on contaminated carriers (CFU count=0). This was compared to control sample that still had a CFU count of $2.54 \times 10^8$. Moreover, pre-coating with $CPC_{sd}$ prevented bacterial contamination of carriers (CFU=0). This was compared to a control with a CFU count of $3.5 \times 10^8$.

A commercial disinfectant containing benzalkonium chloride and ethanol was used as a comparator (Bkc-EtOH), and was identically tested. The comparator also showed similar antibacterial activity.

The effect of a water rinse on sustained disinfectant activity was studied by washing precoated carriers with MILLI-Q (by transferring them into 2 mL Milli Q autoclaved water and removed in 2-3 seconds) followed by exposure to MRSA for 15 minutes and the number of colony forming units (CFUs) were determined after incubation for about 16-24 hours at 37° C. A commercial disinfectant containing benzalkonium chloride and ethanol was used as a comparator (Bkc-EtOH) and were identically tested. Cells with no disinfectant and phosphate-buffered saline treatment were used as controls.

Figure 31:
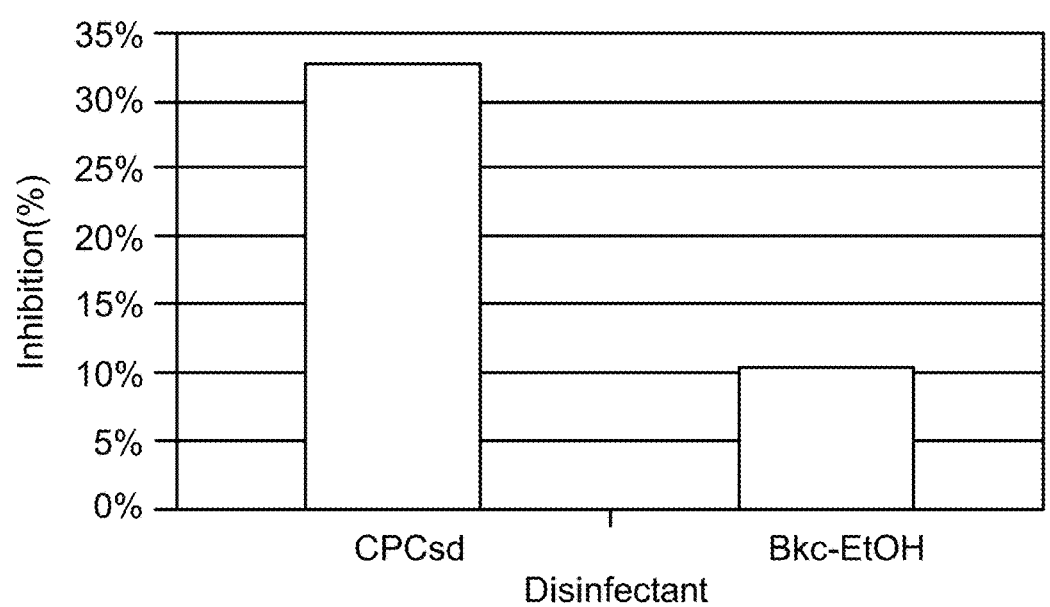
FIG. 31 is a graph showing a test composition and a comparison after a water-wash that corresponds to Example 255.

After the water rinse, and after 16-24 hours carriers treated with $CPC_{sd}$ still exhibited 33% reduction in bacterial counts, compared to a 10% reduction in carriers treated with the comparator (FIG. 31). Therefore, the test composition, $CPC_{sd}$, was able to maintain 3-fold higher activity than the comparator after a water rinse.

Example 256

In Example 256, a clinical trial was performed to evaluate the barrier-forming composition sprayed intra-orally three times daily in comparison to a placebo.

A barrier-forming composition (Test Composition) was created by adding the ingredients listed below in a 50-mL centrifuge tube, and vortexing to bring to a "free-flow" consistency. The constituents of the compositions and their approximate amounts are given in Table I (the values in Table I are percentages by weight of the total composition):

TABLE XX

|  | Test Composition |
|---|---|
| Glycerin | 35 |
| Xanthan Gum | 0.4 |
| Cetyl Pyridinium Chloride | 0.1 |
| Purified water, non-actives, such as flavorings, preservatives (methylparaben (0.1%), propylparaben (0.1%), sodium benzoate (0.5%)) | 64.5 |

A flavored composition with no antimicrobial was obtained to function as a placebo.

The clinical test was conducted primarily to establish the following: whether the active product (Test Composition) decreased the (1) frequency, (2) severity, and/or (3) duration of acute upper respiratory illness (URI). The secondary purposes of the study were to evaluate: (1) the safety, tolerability, acceptability, and adherence to the test composition, (2) the effect of the test composition on work absenteeism and medical visits due to URIs, (3) the effect of the test composition on bacterial and fungal microflora in the oropharynx, and (4) the effect of previous influenza vaccination status on study outcomes.

To test the safety and efficacy of the developed barrier-forming cetylpyridinium chloride (CPC)-based oral spray, a randomized, double-blinded, placebo-controlled pilot clinical trial was conducted. 100 healthy men and women, were randomized with equal proportions (50 each) into an "Active Group" (receiving the test composition) or a "Placebo Group." Participants in both groups were instructed to administer the test composition or placebo intra-orally by spray (three sprays at 0.25 mLs per spray) three times daily in both groups, for 75 days. Children, pregnant women, prisoners and other vulnerable individuals were not enrolled. Enrolled participants presented at the clinic for study visits at enrollment (baseline), and thereafter at 3 monthly follow-up visits, and for a final visit within 2 weeks after the completion of treatment. Of the 100 individuals who were enrolled in the program, 94 completed the study. There were 4 subjects (1 in Placebo Group, 3 in Active Group) who did not complete "Visit 3".

Table XXI summarizes the demographics of study participants. The age of study participants ranged between 18 and 43 years in both groups, with the mean age of 24.86±6.47 years in the Placebo Group and 25.14±6.73 years in the Active Group, with no significant difference observed (P=0.68). The gender distribution was also similar in the two study groups, with 24 males and 20 females in the Placebo Group (54.5% and 45.5%, respectively) and 24 males and 26 females in the Active Group (48% and 52%, respectively). The study duration (number of days from enrollment until the 3rd follow-up visit was 72.8±2.9 for the Placebo Group and 71.8±2.8 for the Active Group.

Among those who completed the study, 44 were in the Placebo Group and 50 were in the Active Group. There was no significant difference between the two groups in their demographic characteristics (age, gender distribution), study duration, and percentage of surveys completed. Demographics of the study participants are record in Table XXI

TABLE XXI

| Variable | Placebo | Active |
| --- | --- | --- |
| Total enrolled | 44 | 50 |
| Male | 24 (54.5%) | 24 (48.0%) |
| Female | 20 (45.5%) | 26 (52.0%) |
| Age (Mean ± SD) | 24.86 ± 6.47 | 25.14 ± 6.73 |
| Age range | 18-43 | 18-43 |
| Percent of surveys completed | 89.1 ± 15.6 | 86.3 ± 20.6 |

Age, gender, influenza vaccine status, and medication taken for symptom alleviation were also recorded. The study length and number of study surveys completed were used to summarize the information available from the diaries.

There were five methods used to survey the participants. (1) Diary surveys that participants were instructed fill out to record their symptoms and severity, as well as any side-effects. (2) Recordations of absenteeism from work or other responsibilities. (3) Clinic "sick visits" upon development of URI symptoms during which PCR analysis was performed to confirm the presence of URI viruses. (4) Bacterial (oral streptococci, Group A *streptococcus*) and fungal cultures performed at interim clinic visits (conducted at an initial and 3 additional visits during the study). (5) A clinic visit at two-weeks post-completion of the administering period. The participants also reported their adherence to the study guidelines.

There were a total of 5945 surveys completed in the study (2849 in the Placebo Group and 3096 in the Active Group). Moreover, percent surveys completed (number of surveys completed divided by study duration) were similar in both groups; 89.1±15.6% and 86.3±20.6% for the placebo and Active Group, respectively.

An acute upper respiratory infection (URI) was defined as a combination of three of any of the following symptoms: fever (>37.8° C.), non-productive cough, sore throat, rhinorrhea (runny nose), sinus congestion (stuffy nose), and malaise (generally not feeling well). Each of these symptoms are considered individually URI-related events (URE). As used herein, the term 3URE means a URI based on reporting of 3 concurrent URE symptoms. (A URI defined in this manner is not the same as a Confirmed URI Episode as that term is used below. A Confirmed URI Episode is confirmed by clinical and laboratory testing.)

Research electronic data capture (REDCap) methodology was used as a tool to collect, store and disseminate the clinical trial-specific clinical data. (Harris et al. 2009 J. Biomed. Informat. 42(2):377-381). Electronic diaries were created using the REDCap system, and participants recorded their symptoms and addressed study-related questionnaire using these electronic diaries. Data analysis was performed to address the primary and secondary objectives described in the study design. Frequency of URI was assessed based on: (1) visits to the clinic where the study participant had at least three URI-related symptoms; these occurrences (sick visits) were further confirmed clinically by study staff and microbiologically by collecting oral and nasal swabs for evaluation of bacterial, fungal and viral presence; (2) interviews conducted by study nurses with the study participants within two weeks of treatment completion (those reporting symptoms were categorized as "post-treatment sick visits") and (3) analysis of daily diaries electronically completed by study participants, describing the presence of at least three symptoms.

Severity of URI-related symptoms was scored on a 5-point scale [0=None, 1=Minor ("Not too bad"), 2=Mild ("A little bad"), 3=Moderate ("Pretty bad"), 4=Severe ("Really bad")], based on diary entries from study participants with at least three symptoms. Determination of duration of URI-related symptoms was performed by assessment of self-reported diaries of study participants (with at least three symptoms) to identify incidences where the symptoms were present for at least two consecutive days.

Each symptom of URI was investigated separately. For each endpoint, the total number of days for which there was an event was recorded. Then, the number of days for which there was an event per 75 days of person-time follow-up (related to the study duration per subject) was recorded in each of the active and Placebo Group. Next a logistic regression model was constructed. The data were taken at the day level, so the endpoint is yes/no for an event on that day. The data included every day for which there was a completed survey. The endpoints were assessed for each treatment group (placebo vs. active product). Because there were multiple daily observations for each individual in the study (nominally 75 repeated measures per subject, but different for each subject) an ordinary logistic regression model was inappropriate because the observations within a subject from day-to-day would be expected to be correlated. Therefore, generalized estimating equations (GEE) were used to fit the regression model. An autoregressive correlation structure (lag=1) was chosen because it would be expected that a subject's event status today would be correlated with their status yesterday (and tomorrow) but not highly correlated with days more than one day ago (or to come) above and beyond that which can be explained by the 1-day lag (lead). The raw number of events for each group is scaled to the nominal study length of 75 days.

Medical visits (an indicator of whether a subject went to an Emergency Department, an urgent care center, or a doctor's office due to URI symptoms on each day) and absenteeism (an indicator of whether a subject missed school or work or would have missed school or work if it were scheduled on each day) were analyzed the same way as the individual symptom analyses. The effect of vaccine status on the outcomes was assessed by fitting a multiple logistic regression model with treatment group and vaccine status as the explanatory variables. As above, GEE was used to account for the multiple observations per subject.

Results

The results presented below reflect the primary and secondary objectives of the study, and are presented in sections describing: (1) Frequency of Confirmed URI Episodes (from "sick visits"), (2) Frequency of URIs in "post-treatment sick visits" within 2 weeks of study completion, (3) Frequency and severity of URI-events based on electronic diary entries, (4) Duration of URI-related symptoms, (5) Safety, tolerability, acceptability and adherence to the study agent, (6) Absenteeism and medical visits (visit to physicians' offices, emergency departments and urgent care centers), (7) Effect on the oral microbial burden, and (8) Effect of previous influenza vaccination status on study outcomes.

1. Frequency of Confirmed URIs

Among the 94 enrolled individuals, there were six participants who presented to the clinic for collection of oral and nasal swabs related to the development of URI symptoms. Of the participants who presented with a Confirmed URI Episode (determined by clinical evaluation and/or laboratory testing), four belonged to the placebo and two belonged to the Active Group, indicating a 55% reduction in the active versus Placebo Group. PCR analysis performed on the oral and nasal swabs collected from these individuals showed the presence of three respiratory viruses (influenza, coronavirus, or rhinovirus) in three participants; all of these belonged to the Placebo Group (Table XXII), demonstrating the presence of viral infection. No virus was detected in the two individuals from the Active Group who came for a "sick visit".

TABLE XXII

Distribution of virus detected in individuals with Confirmed URI

|  | Placebo | Active |
| --- | --- | --- |
| Confirmed URI Episodes (sick visits) | 4 | 2 |
| Virus detected in oral/nasal swabs | 3 | 0 |
| Virus type detected | Influenza, Rhinovirus, Coronavirus* | None |

*One virus type was detected in each of the three participants in the Placebo Group.

Figure 32:
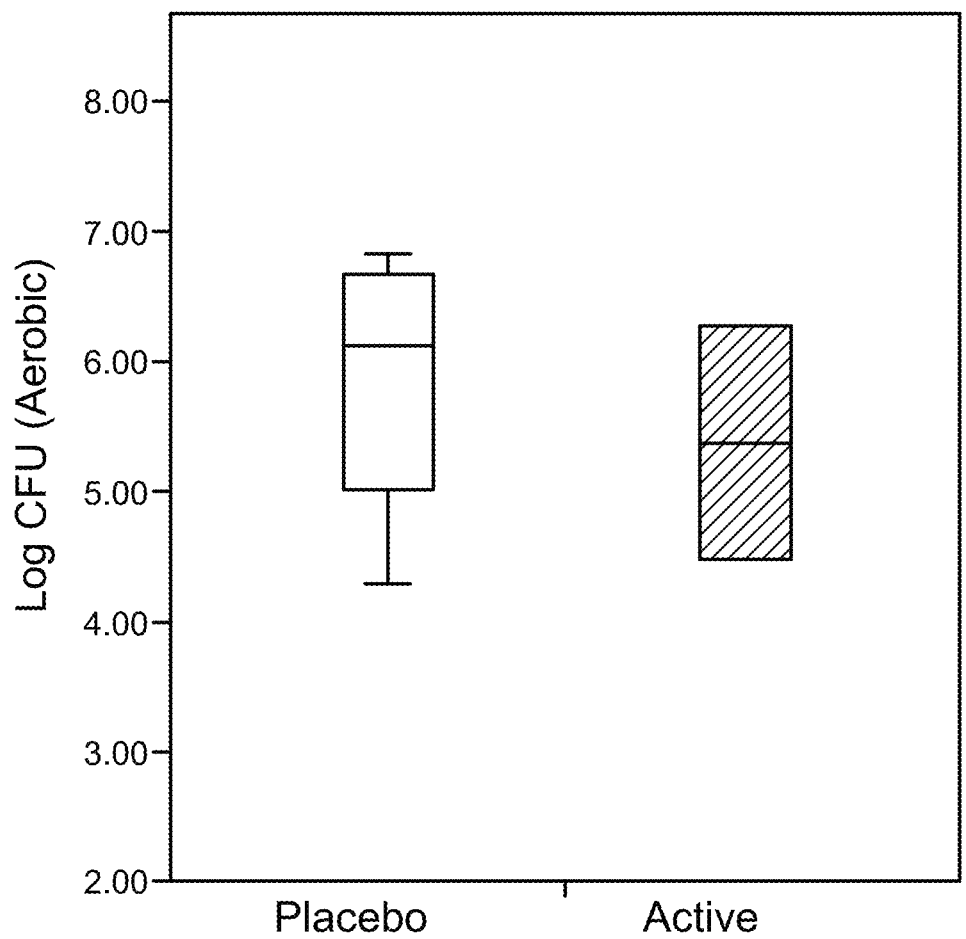
FIG. 32 is a graph corresponding to the results of Example 256, showing median microbial load (log CFUs, aerobic) was lower in individuals with Confirmed URI in the Active Group compared to those in the Placebo Group.

Moreover, analysis of bacterial culture of oral swabs obtained from the six individuals with Confirmed URI Episodes showed that the median microbial burden (log CFU aerobic) tended to be lower in the Active Group compared to the Placebo Group (FIG. 32, P>0.05).

2. Frequency of URIs in Post-Treatment Visits

It was found that six people reported URI-related Events (UREs) at their post-treatment completion of the survey (within 2 weeks of ceasing the dosage of the active product). Among these six individuals, 4 were in the Placebo Group and 2 were in the Active Group, indicating a 55% reduction in the frequency of UREs in the Active Group versus Placebo Group (Table XXIII, P=0.28).

TABLE XXIII

Post-treatment UREs reported by study participants

| Post-Treatment Symptom | Placebo | Active |
| --- | --- | --- |
| Yes | 4 | 2 |
| No | 40 | 48 |

3. Frequency and Severity of URI-Related Events Based on Diary Entries

Analyses of the symptoms reported by study participants in their daily diaries showed a total of 64 occurrences of at least 3 URI-Related Events (3UREs), observed in 20 individuals (Table XXIV). Of these 3UREs, 37 occurred in the Placebo Group (in 11 individuals) while 27 occurred in the Active Group (in 9 individuals). This indicates a 28% reduction in individuals with 3UREs in the active versus Placebo Groups, and a 36% reduction in total 3UREs in the Active Group versus placebo.

TABLE XIV

Frequency and severity of symptoms in study participants with 3UREs

| | Frequency (%)* | | Severity (Mean ± SD) (Min-Max)[§] | |
| --- | --- | --- | --- | --- |
| Symptom | PLACEBO | ACTIVE | PLACEBO | ACTIVE |
| Cough | 29 (78.4%) | 7 (25.9%) | 1.73 ± 1.36 (0-4) | 0.56 ± 1.01 (0-3) |
| Sore throat | 30 (81.1%) | 13 (48.1%) | 0.81 ± 0.39 (0-4) | 0.48 ± 0.50 (0-2) |
| Runny nose | 25 (67.6%) | 18 (66.7%) | 0.95 ± 0.88 (0-3) | 1.56 ± 1.28 (0-3) |
| Stuffy nose | 19 (51.4%) | 26 (96.3%) | 0.89 ± 1.05 (0-3) | 2.07 ± 0.87 (0-3) |
| Malaise | 22 (59.5%) | 21 (77.8%) | 1.49 ± 1.38 (0-4) | 1.67 ± 1.03 (0-3) |
| Fever | 4 (10.8%) | 0 | 100-103° F. | — |

*Percentage values are compared to the total number of events in each group (placebo and active). (The totals sum to over 100% because one day may have several reported symptoms.)

[§]Severity of URI-related symptoms was scored on a 5-point scale [0 = None, 1 = Minor ("Not too bad"), 2 = Mild ("A little bad"), 3 = Moderate ("Pretty bad"), 4 = Severe ("Really bad")], based on diary entries from study participants with at least three symptoms.

Data represent Mean ± SD (Minimum-Maximum).

Analysis of severity of 3UREs showed that fever was reported only in the Placebo Group (10.8%), and the severity of cough and sore throat was significantly reduced in the Active Group compared to the Placebo Group (P=0.062 and <0.001, respectively). Moreover, Chi-square analysis of symptoms in individuals with 3UREs showed that relative risk (RR) of cough in Placebo Group was 3-times that of people in the Active Group (P<0.001), while the RR of sore throat was 1.6-times that of people in the Active Group (Table XXV, P=0.008).

TABLE XXV

Chi-square analysis of symptoms in individuals with 3UREs, in the two arms

| Variable | Number of Events PLACEBO | Number of Events ACTIVE | Odds Ratio[1] | Relative Risk[2] | 95% Confidence Interval for RR Minimum | 95% Confidence Interval for RR Maximum | P-value[3] |
|---|---|---|---|---|---|---|---|
| Fever | 4 | 0 | | | | | |
| Cough | 29 | 7 | 0.10 | 3.02 | 1.563 | 5.847 | <.001 |
| Sore Throat | 30 | 13 | 0.22 | 1.68 | 1.105 | 2.566 | 0.008 |
| Runny Nose | 25 | 18 | 0.96 | 1.01 | 0.716 | 1.435 | 1 |
| Stuffy Nose | 19 | 26 | 24.63 | 0.53 | 0.386 | 0.736 | <.001 |
| Malaise | 22 | 21 | 2.39 | 0.76 | 0.548 | 1.067 | 0.179 |

[1]OR = Odds Ratio was calculated for Placebo/Active
[2]RR = Relative Risk was calculated for each symptom
[3]Fisher's Exact Test (2-sided)

The analysis also indicated that the number of cough, sore throat, or runny nose events per 75 person days tended to be lower in the Active Group compared to the Placebo Group (Table XXVI). This analysis also showed that the Active Group had less cough, sore throat, or rhinorrhea (odds ratio, OR<1) but did not have less nasal congestion or malaise (OR>1).

TABLE XXVI

Analyses of symptoms by person-days

| Event type | Number of Events | Events per 75 person-days PLACEBO | Events per 75 person-days ACTIVE | OR (CI) | p-value |
|---|---|---|---|---|---|
| 3UREs | 64 | 1.0 | 0.7 | 0.68 (0.25, 1.86) | 0.45 |
| Cough | 107 | 2.1 | 0.7 | 0.48 (0.14, 1.64) | 0.24 |
| Sore throat | 113 | 1.8 | 1.0 | 0.60 (0.26, 1.40) | 0.23 |
| Runny nose | 135 | 2.1 | 1.3 | 0.70 (0.23, 2.10) | 0.52 |
| Stuffy nose | 120 | 1.2 | 1.8 | 1.52 (0.62, 3.77) | 0.36 |
| Malaise | 81 | 0.9 | 1.1 | 1.14 (0.47, 2.77) | 0.77 |

Figure 33:
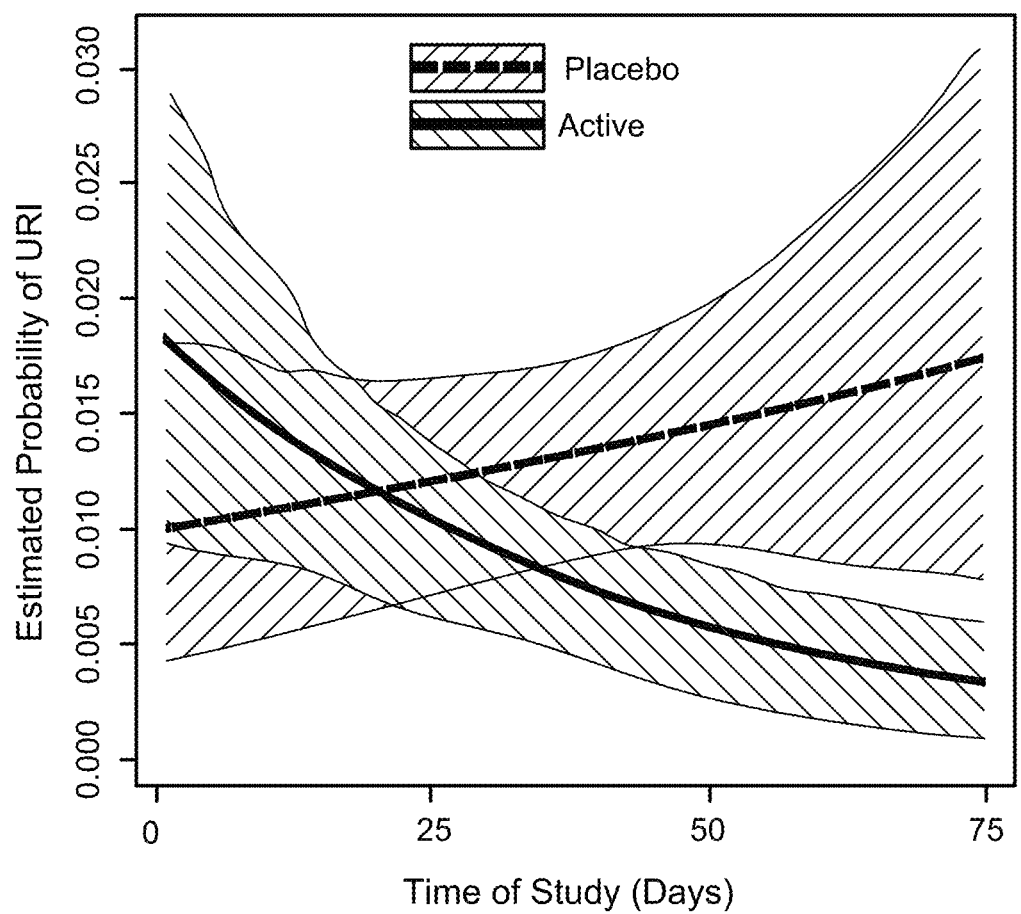
FIG. 33 is a graph corresponding to the results of Example 256, showing probability of 3UREs in the Placebo and Active Group over the duration of the Example 256 clinical trial.

The probability of 3UREs was also estimated in the Placebo Group and Active Groups using the logistic regression model (described above). As shown in FIG. 33, the confidence band for the Active Group passes over (on top of) the confidence band for the Placebo Group after Day 50 on the study. This analysis also showed that active treatment is protective relative to the Placebo Group at times 25, 50, and 75 days in the study (P=0.79, 0.26, and 0.19, respectively). These analyses indicated that protection against URI increases over time of product use. (Data from Day 1 reflects baseline, when treatment was not initiated (pre-treatment).)

4. Duration of URI-Related Symptoms

The duration of symptoms was assessed in individuals who reported 3UREs for at least two consecutive days. This analysis showed that there were eight such individuals in the Placebo Group and seven in the Active Group. As shown in Table XXVII, fever was reported in only the Placebo Group in two different individuals, and lasted for two days. The median duration of cough, sore throat or runny nose was 2.5 days for each symptom in the Placebo Group, while the median duration of these symptoms was 0, 1, or 2 days, respectively, in the Active Group. The median duration of stuffy nose and malaise was 2 days in both the study groups. The maximum duration for all the non-fever symptoms was between 5 to 9 days in the Placebo Group, while this duration was lower (3 to 5 days) in the Active Group (P=0.019 for cough, >0.05 for all other comparison).

TABLE XXVII

Duration (days) of symptoms in study participants with 3UREs

| Symptom | PLACEBO (days) Median | PLACEBO (days) Min | PLACEBO (days) Max | ACTIVE (days) Median | ACTIVE (days) Min | ACTIVE (days) Max |
|---|---|---|---|---|---|---|
| Fever | 0 | 0 | 2 | 0 | 0 | 0 |
| Cough | 2.5 | 2 | 7 | 0 | 0 | 3 |
| Sore Throat | 2.5 | 0 | 9 | 1 | 0 | 3 |
| Runny Nose | 2.5 | 0 | 7 | 2 | 0 | 5 |
| Stuffy Nose | 2 | 0 | 5 | 2 | 2 | 5 |
| Malaise | 2 | 0 | 9 | 2 | 0 | 5 |

5. Safety, Tolerability, Acceptability and Adherence

The safety, tolerability, acceptability, and adherence were evaluated by oral exams, solicited, and unsolicited adverse events (AEs), end-of-study acceptability surveys, and self-reported use of sprays.

Oral Exams: As part of the study protocol, oral exams were conducted on all study participants. Among the 94 enrolled participants, abnormal oral exams were reported for four individuals, of which three belonged to the Placebo Group (cheek biting for two, and labial mucosal injury in one participant) and one was in the Active Group (enlarged tonsils at enrollment, not noted at subsequent visits or at end of study). None of these oral events were related to the study drug.

Adverse Events: A total of nine adverse events (AEs) were reported in the study (with a 75-day duration), of which five occurred in the Placebo Group, while four occurred in the Active Group (Table 8). None of the AEs were considered to be related to the study medication.

TABLE XXVIII

Adverse events reported in the study

| Adverse Event | Overall | Placebo | Active |
|---|---|---|---|
| Headache | 4 | 2 | 2 |
| Anxiety | 2 | 1 | 1 |
| Extremity rash | 1 | 0 | 1 |
| Labial mucosal injury | 1 | 1 | 0 |
| Muscle strain | 1 | 1 | 0 |

Acceptability: Participants were asked to complete an exit questionnaire with questions related to acceptability of the active product at the end of the study. The results were favorable with majorities approving of the taste, smell of the composition and indicating a willingness to continue to use the product.

Adherence: Adherence to the study guidelines was assessed by self-reported use of the agent (three sprays a day). The analysis showed that spray was used as indicated in ≥85% of the days in the placebo and ≥86.9% in the Active Group (Table 9). These results indicate that study participants exhibited high degree of adherence to the study protocol and application of the study drug.

TABLE IXXX

Adherence to applying study medication

| Spray Event | Placebo | Active |
|---|---|---|
| First Spray | 85.9% | 88.4% |
| Second Spray | 85.3% | 86.9% |
| Third Spray | 85.0% | 87.2% |

6. Absenteeism and Medical Visits

There were a total of 5945 surveys completed in the study (2849 in placebo and 3096 in Active Group). The medical care question was left blank on 61 surveys, so data are only available for 5884 surveys (2841 in placebo and 3043 in Active Group). Among individuals with 3UREs, there were two medical visits (visits to a doctor other than the clinic), both in the Placebo Group, and 9 absentee episodes of which five (13.5%) were in the Placebo Group, and four (14.8%) in the Active Group. These results showed that medical visits occurred only in the Placebo Group while absenteeism did not significantly differ between the two arms.

7. Effect on Oral Microbial Burden

Figure 34:
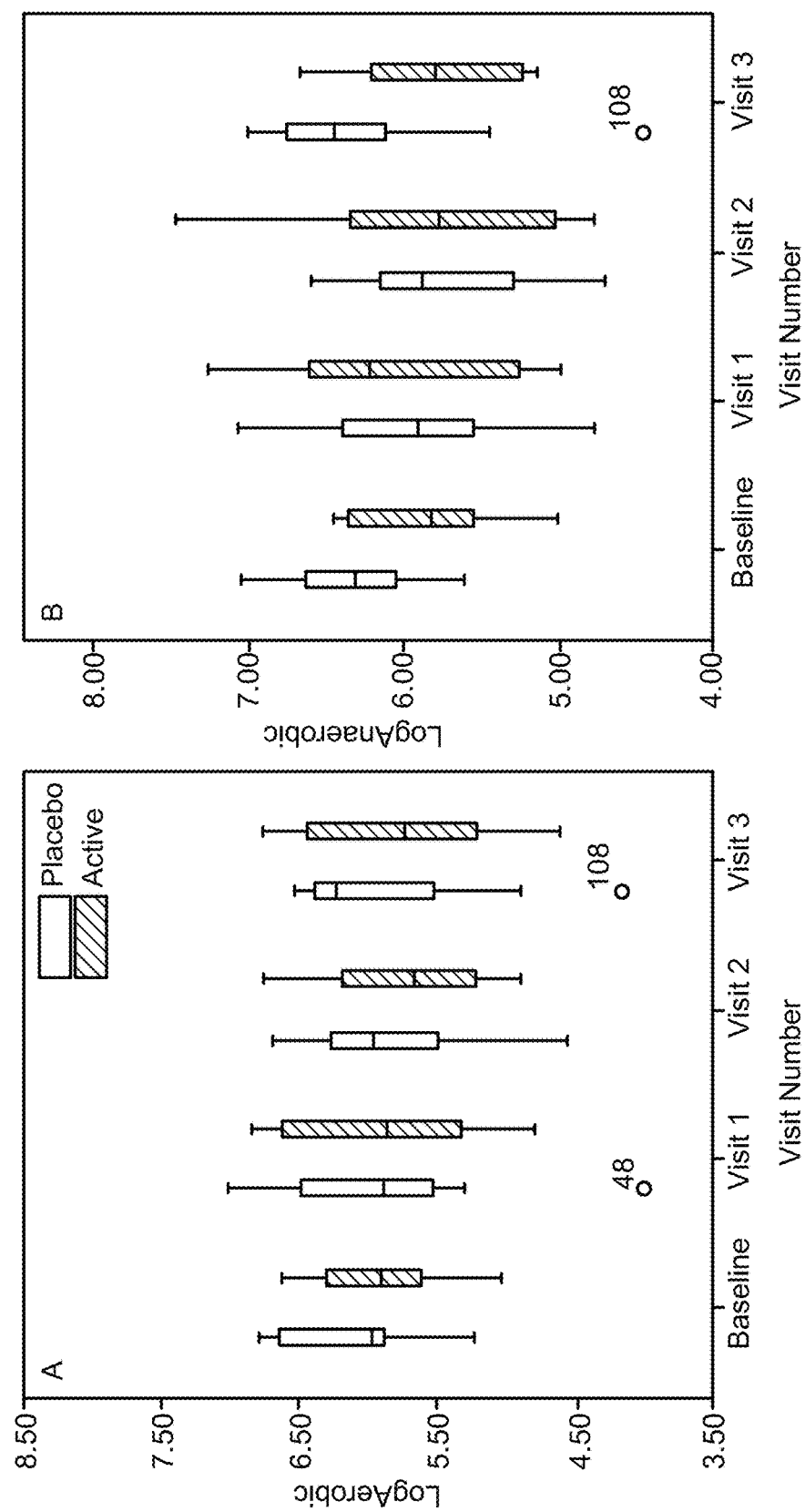
FIG. 34 is graph corresponding to Example 256 showing the distribution of oral microbial burden in the Placebo and Active Groups in participants with 3UREs, analyzed at different study visits.

Assessment of the microbiology data revealed that the oral microbial (bacterial) burden tended to be lower in the Active Group compared to the Placebo Group, as measured by the number of aerobic and anaerobic bacteria (P>0.05 for all comparisons between the two groups). Further analysis of the distribution of oral microbes in individuals with 3UREs across different visits showed that, in general, there was a trend for the median log CFUs to be lower in Active Group than in the Placebo Group, especially at visits 2 and 3 (see boxplots in FIG. 34). Panels show the log number of CFUs for: (A) aerobic and (B) anaerobic bacteria. Circles represent outliers.

Figure 35:
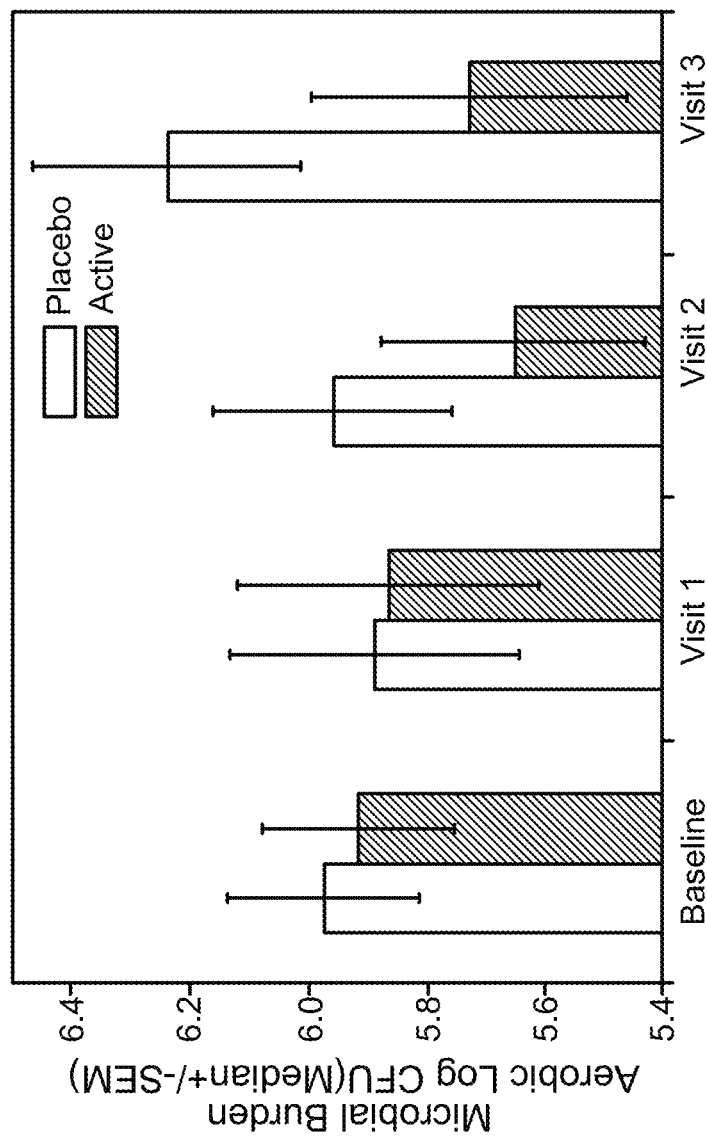
FIG. 35 is a graph corresponding to Example 256 showing the median log CFUs (+/−Std. Error of Mean) of aerobic microbes compared at different visits for individuals with 3UREs.

Next, the median log CFUs were compared at different visits for individuals with 3UREs (FIG. 35), and found that microbial burden in the Active Group continued to decrease from baseline to the last study visit (Visit 3, FIG. 35). In contrast, the microbial burden in the Placebo Group continued to increase during the same study visits. Interestingly, the difference between Placebo and Active Groups at the study visits increased from 0.02 at Visit 1 to 0.51 at Visit 3 (a difference of 22 fold at Visit 3).

In addition, it was found that one sub-group (males, between 25-34 years old) had lower bacterial burden in the Active Group than the Placebo Group at all four study visits, with the difference being statistically significant at Visit 1 (P=0.028).

Culturing of oral swabs on fungi-specific agar medium failed to show any fungal growth in all the tested swab samples for the enrolled study participants.

PCR analysis was performed on the oral swabs collected from the study participants at the regular study visits. Analyses of oral swabs collected from participants at the regular study visits (baseline, visit 1, visit 2, and visit 3) did not detect any respiratory virus, except for the presence of enterovirus in one individual in the Placebo Group. Three viruses were detected in three individuals who presented for sick visits (as described above).

8. Effect of Vaccination Status

Among the enrolled 94 individuals, 41 reported receiving influenza vaccine previously, of which 17 (38.6%) belonged to the Placebo Group while 24 (48%) belonged to the Active Group. Multivariable logistic regression analysis revealed the vaccine status had no significant effect on UREs (P=0.15). These results showed that vaccination status did not influence the UREs between the two arms.

Results from this clinical trial showed: (1) the frequency of Confirmed URI Episodes and post-treatment sick visits were reduced by 55% in the active compared to the Placebo Group, (2) the frequency and severity of UREs (based on diary entries) were reduced in the Active Group, with fever reported only in the placebo, and cough and sore throat being statistically significantly less in the Active Groups, (3) the median duration of URI-related cough and sore throat was higher in the Placebo Group (2.5 days for both) compared to the Active Group (0 and 1 day, respectively), (4) the product was safe, well-tolerated and had high acceptability among the enrolled participants, (5) adherence to the active and study protocol was high, (6) medical visits occurred only in the Placebo Group while absenteeism did not differ between the two arms, (7) the oral microbial burden was reduced in the Active Group compared to the Placebo Group, and (8) there was no effect of previous influenza vaccination status on the study outcomes.

Summary of Results

Prevention (Based on Frequency of (1.) Confirmed URIs and Post-Treatment Sick Visits and (2.) Diary Entries)

Among the 94 enrolled individuals, there were six participants who presented to the clinic for collection of oral and nasal swabs related to the development of URI symptoms (Confirmed URI Episodes). Among the six Confirmed URI Episodes, four belonged to the Placebo Group and two belonged to the Active Group, indicating a 55% reduction in URI for the Active Group, based only on evaluation of symptoms by a nurse or doctor at the sick visits. (The percentage is higher than 50%, because fewer persons in the Placebo Group completed the trial.)

PCR analysis performed on the oral and nasal swabs collected from these individuals during the sick visits showed the presence of three respiratory viruses (influenza, coronavirus, or rhinovirus) in three participants; all of these belonged to the Placebo Group. No virus was detected in the two individuals from the Active Group who came for a "sick visit". Furthermore, the frequency of post-treatment sick visits within 2 weeks of study completion, was also reduced by 55% in the Active Group compared to the Placebo Group (N=4 and 2, respectively).

Symptom Duration and Severity

Analysis of daily diaries of the study participants also revealed that the frequency and severity of "URI Events" (UREs) were reduced in the Active Group, with fever reported only in the Placebo Group. The reduction in frequency and severity of cough and sore throat symptoms were statistically significant between the two groups (P≤0.008). It was also found that the median duration of URI-related cough and sore throat was higher in the Placebo Group (2.5 days for both) compared to the Active Group (0 and 1 day, P=0.019 and 0.102, respectively).

Safety/Side Effects

Additionally, the results showed that the test composition was safe, well-tolerated, and had high acceptability among the enrolled participants, and that adherence to the active agent and study protocol was high.

Adherence to Study Guidelines

Reported adherence to the study protocol was high.

Effect on Medical Visits and Absenteeism

Medical visits (an indicator of whether a subject went to an emergency department, an urgent care center, or a doctor's office due to URI symptoms) and absenteeism (an indicator of whether a subject missed school or work or would have missed school or work if it were scheduled on each day) occurred only in the Placebo Group while absenteeism did not differ between the two groups.

Reduction in Microbial Burden

Microbiology analyses revealed that the oral microbial burden was reduced in the Active Group compared to the Placebo Group.

Non-Effect of Flu Vaccine on Study

Finally, there was no effect of previous influenza vaccination status on the study outcome.

In conclusion, this clinical trial demonstrated that the tested product was protective against URIs in the enrolled study participants, and that protection against URI increases over time of product use.

It is claimed:

1. A method for treating a viral upper respiratory infection or for treating a symptom of the viral upper respiratory infection, or a combination of both the disease being caused or aggravated by microorganisms, comprising:

treating the viral upper respiratory infection, treating the symptom of the viral upper respiratory infection, or reducing the duration of the viral upper respiratory infection, or combinations thereof, by administering a barrier-forming composition in a therapeutically effective amount to a surface, the surface comprising a mammal mucosa, the mammal being infected with the viral upper respiratory infection or experiencing symptoms of the viral upper respiratory infection;

the barrier-forming composition comprising an antimicrobial;

forming a barrier coating on the surface that is active to kill or neutralize microorganisms encountered by the barrier coating;

wherein the barrier-forming composition is effective to reduce duration, frequency, or severity of one or more of cough, sore throat, and fever;

wherein the barrier-forming composition meets the following requirements:
   about 0.0001%≤C<0.4%;
   about 0.07%≤H≤about 70%; and
   0.0005%<A wherein all percentages are by weight of the total composition;
   wherein C is a carbohydrate gum; H is a humectant; and A is the antimicrobial agent.

2. The method of claim 1, further comprising effectively reducing the microbial load on the surface.

3. The method of claim 1, wherein the viral upper respiratory infection is one or more diseases selected from the group consisting of: influenza and rhinovirus.

4. The method of claim 1, wherein the viral upper respiratory infection is influenza.

5. The method of claim 1, wherein the one or more symptoms further comprise at least one of the following: runny nose, nausea, headache, sneezing, sinus pressure, aches and pains, watery eyes, sinus congestion, chills, vomiting, malaise, fatigue, and rhinorrhea.

6. The method of claim 1, wherein multiple symptoms of the viral upper respiratory infection are treated by administering the composition.

7. The method of claim 1, further comprising administering the barrier-forming composition in the therapeutically effective amount to the surface, for one time or more, for at least two consecutive 24 hour periods.

8. The method of claim 1, further administering the barrier-forming composition in the therapeutically effective amount to the surface three or more times in a 24 hour period for at least two consecutive 24 hour periods.

9. The method of claim 1, wherein there is about 25% to about 99% reduction of the microbial burden from about one to about six hours after the administering step.

10. The method of claim 1, wherein the mucosa is one or more of an oral, nasal, or pharyngeal mucosa.

11. The method of claim 1, wherein the barrier layer has antimicrobial cidal or static activity for a duration of about six to about twenty-four hours.

12. The method of claim 1, wherein the barrier-forming composition is applied by spraying.

13. The method of claim 1, wherein the antimicrobial agent is a broad-spectrum antimicrobial.

14. The method of claim 1, wherein the microorganisms are influenza viruses.

15. The method of claim 1, wherein the microorganisms are rhinovirus.

16. The method of claim 1, wherein the antimicrobial agent is a monoquaternary ammonium compound.

17. The method of claim 1, wherein the barrier coating is active to trap, and kill or neutralize microorganisms encountered by the barrier coating for a duration of at least one hour.

18. The method of claim 1, wherein the barrier-forming composition is a solution.

19. The method of claim 1, wherein the step of administering the barrier-forming composition occurs in response to:
   a. identifying a contaminated environment that the mammal is present in or is going to be present in, wherein the contaminated environment is known or expected to be contaminated with harmful viral, fungal, or bacterial microorganisms; or
   b. observing a contamination event in an environment wherein the mammal with the elevated risk condition is present in the environment or is going to be present in the environment.

20. The method of claim 1, wherein the barrier-forming composition has a viscosity of less than 500 cps.

21. The method of claim 1, wherein the barrier-forming composition has antimicrobial cidal or static activity for a duration of about six to about twenty-four hours.

22. The method of claim 1, wherein the composition is not effective to function by killing microorganisms through nanoemulsion activity or repelling microorganisms by an anti-adherence mechanism.

23. A method for treating a viral upper respiratory infection or for treating a symptom of a viral upper respiratory infection, or a combination of both, the viral upper respiratory infection, comprising:
   treating the viral upper respiratory infection, treating the symptom of the viral upper respiratory infection, or reducing the duration of the viral upper respiratory infection, or a combination thereof, by administering a barrier-forming composition in a therapeutically effective amount to a surface, the surface comprising a mammal mucosa, the mammal being infected with the viral upper respiratory infection;
   the barrier-forming composition comprising an antimicrobial agent that acts by binding to a cell membrane of the microorganisms and disrupting the cell membrane, thereby causing cell death;
   effectively reducing the duration, frequency, or severity of the viral upper respiratory infection, or effectively reducing the duration, frequency, or severity of one or more symptoms of the viral upper respiratory infection;
   the method being safe and free of harmful side effects;
   wherein the barrier-forming composition meets the following requirements:
   about $0.0001\% \leq C < 0.4\%$;
   about $0.07\% \leq H \leq$ about $70\%$; and
   $0.0005\% < A$
   wherein all percentages are by weight of the total composition;
   wherein C is a carbohydrate gum; H is a humectant; and A is the antimicrobial agent.

24. The method of claim 23, wherein the antimicrobial agent is exclusive of fatty acid ethers or esters of polyhydric alcohols or alkoxylated derivatives thereof.

25. The method of claim 1, wherein the antimicrobial agent is cetyl pyridinium chloride.

26. The method of claim 1, wherein the mammal mucosa is an oral or pharyngeal mucosa.

27. The method of claim 1, wherein the step of treating occurs after the mammal experiences symptoms of the disease.

28. The method of claim 1, wherein the treatment step is iterated three times per day.

29. The method of claim 1, wherein the antimicrobial agent is present in an amount of about 0.0025% to about 0.1% by weight of the total composition.

30. The method of claim 1, wherein the treating step is selected from the group consisting of: treating the viral upper respiratory infection, reducing the duration of the viral upper respiratory infection, and combinations thereof.

* * * * *